United States Patent
Javitch et al.

(10) Patent No.: US 9,868,730 B2
(45) Date of Patent: Jan. 16, 2018

(54) KAPPA OPIOID RECEPTOR SELECTIVE COMPOUNDS, COMPOSITIONS, AND USES THEREOF

(71) Applicants: Jonathan Javitch, New Rochelle, NY (US); Marie-Laure Rives, Cabestany (FR); Marta Filizola, Riverdale, NY (US); Thomas E. Prisinzano, Lawrence, KS (US)

(72) Inventors: Jonathan Javitch, New Rochelle, NY (US); Marie-Laure Rives, Cabestany (FR); Marta Filizola, Riverdale, NY (US); Thomas E. Prisinzano, Lawrence, KS (US)

(73) Assignees: The Trustees of Columbia University in the City of New York, New York, NY (US); Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 14/768,434

(22) PCT Filed: Feb. 14, 2014

(86) PCT No.: PCT/US2014/016519
§ 371 (c)(1),
(2) Date: Aug. 17, 2015

(87) PCT Pub. No.: WO2014/127256
PCT Pub. Date: Aug. 21, 2014

(65) Prior Publication Data
US 2016/0002216 A1     Jan. 7, 2016

Related U.S. Application Data

(60) Provisional application No. 61/766,035, filed on Feb. 18, 2013, provisional application No. 61/768,205, filed on Feb. 22, 2013.

(51) Int. Cl.
*C07D 417/12* (2006.01)

(52) U.S. Cl.
CPC .................................. *C07D 417/12* (2013.01)

(58) Field of Classification Search
CPC .................................................... C07D 417/12
See application file for complete search history.

(56) References Cited

U.S. PATENT DOCUMENTS

| | | |
|---|---|---|
| 7,683,168 B2 | 3/2010 | Jan et al. |
| 2004/0157886 A1 | 8/2004 | Domany et al. |
| 2011/0105481 A1 | 5/2011 | Barbier et al. |
| 2011/0190347 A1 | 8/2011 | Gage et al. |
| 2011/0190348 A1 | 8/2011 | Banerjee |
| 2012/0015052 A1 | 1/2012 | Burgey et al. |
| 2012/0295853 A1 | 11/2012 | Ambron et al. |
| 2013/0005718 A1 | 1/2013 | Tibbs et al. |

FOREIGN PATENT DOCUMENTS

| | | |
|---|---|---|
| WO | 2006/138589 A2 | 12/2006 |
| WO | 2010/025272 A1 | 3/2010 |
| WO | 2012/052540 A1 | 4/2012 |

OTHER PUBLICATIONS

Chemical Abstracts Registry No. 1333852-71-3, indexed in the Registry file on STN CAS Online on Sep. 29, 2011.*
Chemical Abstracts Registry No. 1386863-41-7, indexed in the Registry file on STN CAS Online Aug. 6, 2012.*
Ukrorgsyntez Ltd. website, http://ukrorgsyntez.lookchem.com and http://uorsy.com/screening-compounds.php, accessed Wednesday, Mar. 29, 2017.*
Enamine website, https://www.enaminestore.com/catalog/T7049170 and http://www.enamine.net/index.php?option=com_content&task=view&id=22, accessed Wednesday, Mar. 29, 2017.*
Barducci A, et al. (2008) Well-tempered metadynamics: a smoothly converging and tunable free-energy method. Phys Rev Lett 100: 020603.
Branduardi D, et al. (2007) From A to B in free energy space. J Chem Phys 126: 054103.
Bruchas MR, Chavkin C (2010) Kinase cascades and ligand-directed signaling at the kappa opioid receptor. Psychopharmacology (Berl) 210: 137-147.
Carlsson, J., et al. (2010) Structure-based discovery of A2A adenosine receptor ligands. J Med Chem 53, 3748-3755.
Chavkin C (2011) The therapeutic potential of kappa-opioids for treatment of pain and addiction. Neuropsychopharmacology 36: 369-370.
Chen, Y., et al. (1993) Molecular cloning and functional expression of a mu-opioid receptor from rat brain. Mol Pharmacol 44, 8-12.
Darden T, et al. (1993) Particle mesh Ewald: an Nlog(N) method for Ewald sums in large systems. J Chem Phys 98: 10089-10092.
Delander GE, et al. (1984) Role of spinal mu opioid receptors in the development of morphine tolerance and dependence. J Pharmacol Exp Ther 231: 91-96.

(Continued)

*Primary Examiner* — Laura L. Stockton
(74) *Attorney, Agent, or Firm* — Bryan Cave LLP

(57) ABSTRACT

The present invention provides, inter alia, compounds of formula (I): (structurally represented). Also provided are pharmaceutical compositions containing such compounds and methods for treating or ameliorating the effects of a medical condition in a subject using such compounds or pharmaceutical compositions.

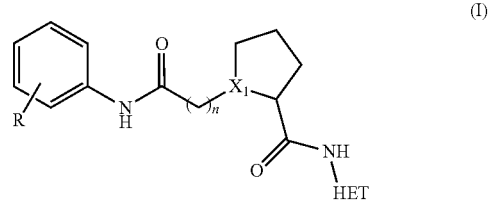

11 Claims, 48 Drawing Sheets
(22 of 48 Drawing Sheet(s) Filed in Color)

(56) References Cited

OTHER PUBLICATIONS

EMCDDA (The European Monitoring Centre for Drugs and Drug Addiction) (2010), Annual report on the state of the drugs problem in Europe. Office of the European Union, Lisbon.
Evans, C. J., et al. (1992) Cloning of a delta opioid receptor by functional expression. Science 258, 1952-1955.
Fields HL (2007) Understanding how opioids contribute to reward and analgesia. Reg Anesth Pain Med 32: 242-246.
Filizola M, Devi LA (2012) Structural biology: How opioid drugs bind to receptors. Nature 485: 314-317.
Filizola, M., and Devi, L. A. (2012b) Grand opening of structure-guided design for novel opioids. Trends in Pharmacological Sciences in press.
Fox T, Kollman PA. (1996) The application of different solvation and electrostatic models in molecular dynamics simulations of ubiquitin: how well is the X-ray structure "maintained"? Proteins. Jul;25(3):315-34.
Fribourg M, et al. (2011) Decoding the signaling of a GPCR heteromeric complex reveals a unifying mechanism of action of antipsychotic drugs. Cell 147: 1011-1023.
Gales, C., et al. (2006) Probing the activation-promoted structural rearrangements in preassembled receptor-G protein complexes. Nat Struct Mol Biol 13, 778-786.
Granier S, et al. (2012) Structure of the delta-opioid receptor bound to naltrindole. Nature 485: 400-404.
Gu SJ et al. (2010) Synthesis and biological evaluation of 1,4-diazepane derivatives as T-type calcium channel blockers. Bioorg Med Chem Lett 20: 2705-2708.
Guo, W., et al. (2008) Dopamine D2 receptors form higher order oligomers at physiological expression levels. Embo J 27, 2293-2304.
Henry, D. J., et al. (1995) Kappa-opioid receptors couple to inwardly rectifying potassium channels when coexpressed by Xenopus oocytes. Mol Pharmacol 47, 551-557.
Hess B, et al. (1997) LINCS: A linear constraint solver for molecular simulations. Journal of Computational Chemistry 18: 1463-1472.
International Search Report for PCT/US2014/016519, dated May 20, 2014.
Irwin JJ, Shoichet BK (2005) ZINC—a free database of commercially available compounds for virtual screening. J Chem lnf Model 45: 177-182.
Jiang, L. I., et al. (2007) Use of a cAMP BRET sensor to characterize a novel regulation of cAMP by the sphingosine 1-phosphate/G13 pathway. J Biol Chem 282, 10576-10584.
Kandt C, et al. (2007) Setting up and running molecular dynamics simulations of membrane proteins. Methods 41: 475-488.
Kieffer, B. L., et al. (1992) The delta-opioid receptor: isolation of a cDNA by expression cloning and pharmacological characterization. Proc Natl Acad Sci U S A 89, 12048-12052.
Klewe, I. V., et al. (2008) Recruitment of beta-arrestin2 to the dopamine D2 receptor: insights into antipsychotic and anti-parkinsonian drug receptor signaling. Neuropharmacology 54, 1215-1222.
Kuntz, I. D., et al. (1982) A geometric approach to macromolecule-ligand interactions. J. Mol. Biol. 161, 269-288.
Land BB, et al. (2009) Activation of the kappa opioid receptor in the dorsal raphe nucleus mediates the aversive effects of stress and reinstates drug seeking. Proc Natl Acad Sci U S A 106: 19168-19173.
Lorber, D. M., and Shoichet, B. K. (1998) Flexible ligand docking using conformational ensembles. Protein Sci. 7, 938-950.
Lorber, D. M., and Shoichet, B. K. (2005) Hierarchical docking of databases of multiple ligand conformations. Curr. Top. Med. Chem. 5, 739-749.
Luo QL, et al. (2005) Inhibitors of type I MetAPs containing pyridine-2-carboxylic acid thiazol-2-ylamide. Part 1: SAR studies on the determination of the key scaffold. Bioorg Med Chem Lett 15: 635-638.
Ma L, et al. (2011) Synthesis and biological evaluation of novel 5-benzylidenethiazolidine-2,4-dione derivatives for the treatment of inflammatory diseases. J Med Chem 54: 2060-2068.
Mackerell AD, Jr., et al. (2004) Extending the treatment of backbone energetics in protein force fields: limitations of gas-phase quantum mechanics in reproducing protein conformational distributions in molecular dynamics simulations. J Comput Chem 25: 1400-1415.
Mackerell Jr. AD, et al. (1998) All-atom empirical potential for molecular modeling and dynamics studies of proteins. J Phys Chem B 102: 3586-3616.
Manglik A, et al. (2012) Crystal structure of the mu-opioid receptor bound to a morphinan antagonist. Nature 485: 321-326.
Marchi M, Ballone P (1999) Adiabatic bias molecular dynamics : a method to navigate the conformational space of complex molecular systems. J Chem Phys 110: 3697-3702.
McCurdy, C. R., Prisinzano, T. E. (2010) Opioid receptor ligands. in Burger's Medicinal Chemistry, Drug Discovery, and Development, Seventh edition (Abraham, D. J., and Rotella, D. R. eds.), John Wiley & Sons, Inc. pp. 569-735.
Minami, M., et al. (1993) Cloning and expression of a cDNA for the rat kappa-opioid receptor. FEBS Lett 329, 291-295.
Miyamoto S, Kollman PA (1992) Settle: an analytical version of the SHAKE and RATTLE algorithm for rigid water models . J Comput Chem 13: 952-962.
Molinari P, et al. (2010) Morphine-like opiates selectively antagonize receptor-arrestin interactions. J Biol Chem 285: 12522-12535.
Mysinger, M. M., and Shoichet, B. K. (2010) Rapid context-dependent ligand desolvation in molecular docking. J Chem Inf Model 50, 1561-1573.
Nagase H, Fujii H (2011) Opioids in preclinical and clinical trials. Top Curr Chem 299: 29-62.
Negri A, et al. (2012) Structure-based virtual screening of small-molecule antagonists of platelet integrin alphaIIbbeta3 that do not prime the receptor to bind ligand. J Comput Aided Mol Des. Sep;26(9):1005-15.
Negri, A., et al. (2013) Discovery of a Novel Selective Kappa-Opioid Receptor Agonist Using Crystal Structure-Based Virtual Screening. Journal of Chemical Information and Modeling, 53(3), 521-526.
Office of Applied Studies (2010) Results from the 2009 National Survey on Drug Use and Health: vol. I. Summary of National Findings. Rockville, MD.
Provasi D, et al. (2011) Ligand-induced modulation of the free-energy landscape of G protein-coupled receptors explored by adaptive biasing techniques. PLoS Comput Biol. Oct;7(10):e1002193.
Rasmussen SG, et al. (2011) Crystal structure of the beta2 adrenergic receptor-Gs protein complex. Nature 477: 549-555.
Rives ML, et al. (2012) 6'-Guanidinonaltrindole (6'-GNTI) is a G protein-biased kappa-opioid receptor agonist that inhibits arrestin recruitment. J Biol Chem 287: 27050-27054.
Rogers, D., et al. (2005) Using extended-connectivity fingerprints with Laplacian-modified Bayesian analysis in high-throughput screening follow-up. J Biomol Screen 10, 682-686.
Rohl CA, et al. (2004) Modeling structurally variable regions in homologous proteins with rosetta. Proteins 55: 656-677.
Rozenfeld R, Devi LA (2010) Receptor heteromerization and drug discovery. Trends Pharmacol Sci 31: 124-130.
Sauliere, A., et al. (2012) Deciphering biased-agonism complexity reveals a new active AT1 receptor entity. Nat Chem Biol 8, 622-630.
Tallent, M., et al. (1994) The cloned kappa opioid receptor couples to an N-type calcium current in undifferentiated PC-12 cells. Neuroscience 63, 1033-1040.
Taussig, R., et al. (1993) Inhibition of adenylyl cyclase by Gi alpha. Science 261, 218-221.
Thompson, A. A., et al. (2012) Structure of the nociceptin/orphanin FQ receptor in complex with a peptide mimetic. Nature 485, 395-399.
Van Der Spoel D, et al. (2005) GROMACS: fast, flexible, and free. J Comput Chem 26: 1701-1718.
Van Rijn RM, et al. (2010) Opioid-receptor-heteromer-specific trafficking and pharmacology. Curr Opin Pharmacol 10: 73-79.
Vanderah TW (2010) Delta and kappa opioid receptors as suitable drug targets for pain. Clin J Pain 26 Suppl 10: S10-15.

(56) References Cited

OTHER PUBLICATIONS

Waldhoer M, et al. (2005) A heterodimer-selective agonist shows in vivo relevance of G protein-coupled receptor dimers. Proc Natl Acad Sci U S A 102: 9050-9055.
Wang C, et al. (2007) Protein-protein docking with backbone flexibility. J Mol Biol 373: 503-519.
Wang YH, et al. (2010) The role of kappa-opioid receptor activation in mediating antinociception and addiction. Acta Pharmacol Sin 31: 1065-1070.
Wawer, M., and Bajorath, J. (2010) Similarity-potency trees: a method to search for SAR information in compound data sets and derive SAR rules. J Chem Inf Model 50, 1395-1409.
Weiner, S. J., et al. (1984) The application of different solvation and electrostatic models in molecular dynamics simulations of ubiquitin: how well is the X-ray structure "maintained"? J. Am. Chem. Soc. 106, 765-784.
Written Opinion of the International Search Authority for PCT/US2014/016519, dated May 20, 2014.
Wu, H., et al. (2012) Structure of the human K-opioid receptor in complex with JDTic. Nature 485, 327-332.
Yu C, et al. (2011) Highly efficient bifunctional organocatalysts for the asymmetric Michael addition of ketones to nitroolefins. Tetrahedron Lett 52: 3298-3302.
Zhu J, et al. (2012) Structure-guided design of a high-affinity platelet integrin alphaIIbbeta3 receptor antagonist that disrupts $Mg(2)(+)$ binding to the MIDAS. Sci Transl Med 4: 125ra132.
Zhu J, et al. (2010) Closed headpiece of integrin alphaIIbbeta3 and its complex with an alphaIIbbeta3-specific antagonist that does not induce opening. Blood 116: 5050-5059.

\* cited by examiner

KAPPA OPIOID RECEPTOR SELECTIVE COMPOUNDS, COMPOSITIONS, AND USES THEREOF

CROSS-REFERENCE TO RELATED APPLICATIONS

This application is the National Stage of International Application No. PCT/US2014/016519, filed Feb. 14, 2014, which claims benefit to U.S. Provisional Patent Application Ser. No. 61/766,035, filed Feb. 18, 2013 and 61/768,205, filed Feb. 22, 2013. The entire contents of the above applications are incorporated by reference as if recited in full.

GOVERNMENT FUNDING

This invention was made with government support under grant Nos. DA026434, DA034049, DA022413, MH054137, DA018151 awarded by the National Institutes of Health. The government has certain rights in the invention.

FIELD OF INVENTION

The present invention provides, inter alia, compounds, including those that selectively activate a Kappa Opioid Receptor (KOP), pharmaceutical compositions containing such compounds, and methods for treating or ameliorating the effects of a medical condition in a subject using such compounds or pharmaceutical compositions.

BACKGROUND OF THE INVENTION

Opioids remain the most widely prescribed and abused class of medicines (2009 National Survey on Drug Use, 2009; Annual report, 2010). Addiction is not the only limiting factor for the effective use of these compounds as powerful painkillers, antitussives, antidepressants, or antipruritic agents. In addition to social and legal issues associated with their use for non-medical, recreational purposes, several adverse effects (e.g., dysphoria, constipation, respiratory depression, nausea, vomiting, etc.) (McCurdy et al., 2010) hinder their clinical usefulness and justify the enormous effort put forth by numerous investigators over the years to discover safer opioid therapeutics and/or non-addictive medications. Notwithstanding the continued development of many compounds with opioid activity, ranging from useful agents in the clinic to important chemical tools to study the endogenous opioid system, a safe, non-addictive and effective opioid drug is yet to be discovered (McCurdy et al., 2010).

Notable members of the superfamily of G protein-coupled receptors (GPCRs), mu-, delta-, and kappa-opioid (or MOP, DOP, and KOP) receptor subtypes (Evans et al., 1992; Kieffer et al., 1992; Minami et al., 1993; Chen et al., 1993) are natural targets for the majority of opioid ligands. The most clinically used opioid drugs act as agonists at the MOP receptor (McCurdy et al., 2010), and exert addiction liability through activity at this receptor (DeLander et al., 1984; Fields, 2007). Thus, it has been proposed that high-affinity selective ligands of the DOP and KOP receptors would provide more effective routes to discovering non-addictive analgesics (Nagase et al., 2011; Vanderah, 2010). In particular, KOP receptor agonists have been shown to be unable to activate the reward pathway (Wang et aL, 2010) while still acting as effective pain suppressors on the central nervous system (CNS) and/or the periphery (Vanderah, 2010), most likely through the $G_{i/o}$ protein-mediated inhibition of cAMP production (Taussig et al., 1993), the blockade of calcium channels (Tallen, 1994), and/or the activation of the inward rectifier potassium channels (Henry et al., 1994). Unfortunately, the KOP receptor agonists developed to date are not ideal drugs as they exert side effects such as dysphoria (Land et al., 2009). However, KOP receptor-mediated dysphoric effects have recently been attributed to the activation of the p38 MAPK pathway following arrestin recruitment to the activated KOP receptor (Land et al., 2009; Bruchas et al., 2010; Chavkin, 2011). Therefore, KOP receptor-selective G-protein biased agonists, which do not recruit arrestin, have been proposed to be more effective analgesics, without the adverse effects triggered by the arrestin pathway (Chavkin, 2011). Such a functionally selective G protein-biased KOP receptor ligand (rives et al., 2012): 6'-guanidinonaltrindole (6'-GNTI) was reported. Although this morphine-derivative ligand is a promising lead compound for non-addictive analgesics acting at the KOP receptor with reduced liability for dysphoria, its effective use as a drug is severely limited by its physicochemical properties and its inability to cross the blood brain barrier.

The lack of a detailed molecular-level understanding of the interactions between opioids and their receptors has hindered successful receptor-based drug design. By revealing how opioid ligands bind to their receptors, recent high-resolution crystal structures of all 4 opioid receptor subtypes, i.e., the MOP (Manglik et al., 2012), DOP (Granier et al., 2012), KOP (Wu et al., 2012), and nociceptin/orphanin FQ (Thompson et al., 2012) receptors, offer an unprecedented opportunity to discover novel chemotypes targeting these proteins that might eventually be developed into more efficacious therapeutics (Filizola et al., 2012a; Filizola et al., 2012b).

Accordingly, there is a need for non-addictive analgesics and other therapeutics acting at the KOP receptor, especially ones that have reduced liability for dysphoria. The present invention is directed to meeting these and other needs.

SUMMARY OF THE INVENTION

One embodiment of the present invention is a compound of formula I:

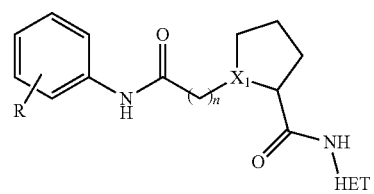

wherein $X_1$ is selected from the group consisting of N, O, and S;

n is an integer between 1 and 10;

HET is a heteroaromatic ring; and

R is a halogen atom or —$C_{1-4}$alkylhalo; or crystalline forms, hydrates, or salts thereof.

Another embodiment of the present invention is a compound of formula II:

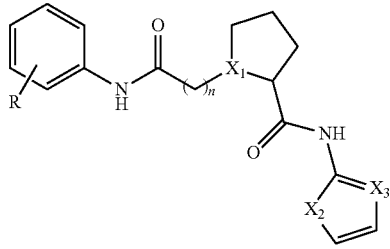

II wherein $X_1$, $X_2$, and $X_3$ are independently selected from the group consisting of N, O, and S;

n is an integer between 1 and 10; and

R is a halogen atom or —$C_{1-4}$alkylhalo; or crystalline forms, hydrates, or salts thereof.

A further embodiment of the present invention is compound of formula III:

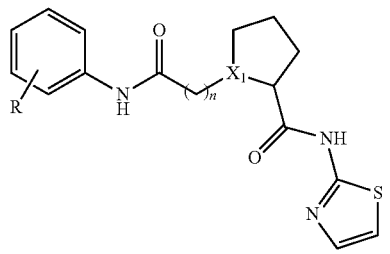

III wherein $X_1$ is selected from the group consisting of N, O, and S;

n is an integer between 1 and 10; and

R is a halogen atom or —$C_{1-4}$alkylhalo; or crystalline forms, hydrates, or salts thereof.

Another embodiment of the present invention is a compound of formula IV:

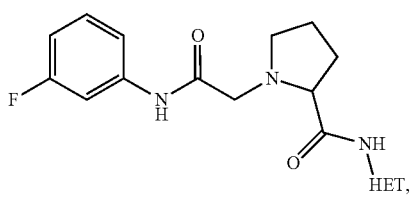

IV wherein

HET is a heteroaromatic ring; or crystalline forms, hydrates, or salts thereof.

An additional embodiment of the present invention is a compound of formula V:

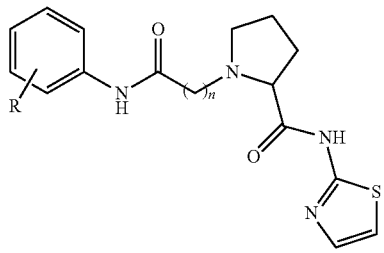

V wherein n is selected from an integer between 1 and 10; and

R is a halogen atom or —$C_{1-4}$alkylhalo; or crystalline forms, hydrates, or salts thereof.

Another embodiment of the present invention is a compound of formula VI substantially free of its R-enantiomer:

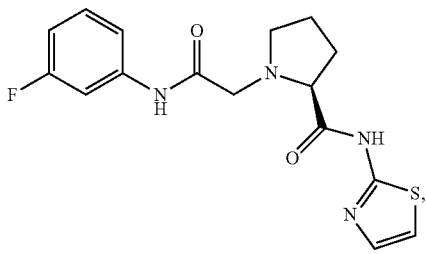

VI or crystalline forms, hydrates, or salts thereof.

An additional embodiment of the present invention is a compound of the structure

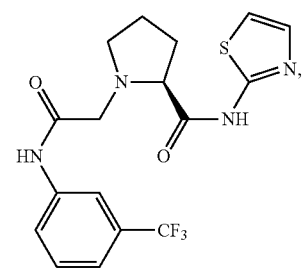 [SMILES: O=C(CN1CCC[C@H]1C(=O)Nc1nccs1)Nc1cccc(C(F)(F)F)c1]

or crystalline forms, hydrates, or salts thereof.

A further embodiment of the present invention is any compound disclosed herein, which selectively activates a Kappa Opioid Receptor (KOP) over a Delta Opioid Receptor (DOP) or over a Mu Opioid Receptor (MOP) and is biased toward G protein activation over arrestin.

Another embodiment of the present invention is a pharmaceutical composition comprising any compound disclosed herein and a pharmaceutically acceptable carrier.

A further embodiment of the present invention is a pharmaceutical composition comprising a compound of formula VI substantially free of its R-enantiomer:

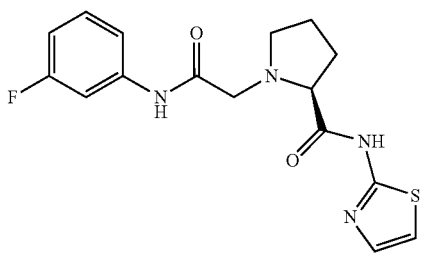

VI and a pharmaceutically acceptable carrier.

A further embodiment of the present invention is a method for treating or ameliorating the effects of a condition in a subject in need thereof. This method comprises administering to the subject an effective amount of any compound or pharmaceutical composition disclosed herein.

Another embodiment of the present invention is a method for treating or ameliorating the effects of a condition in a subject in need thereof. This method comprises administering to the subject an effective amount of a pharmaceutical composition comprising a compound of formula VI substantially free of its R-enantiomer:

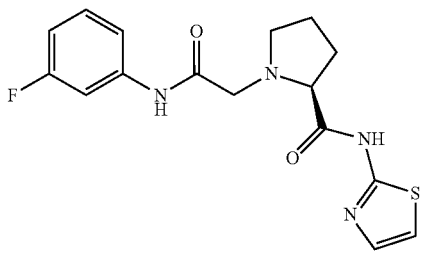

VI and a pharmaceutically acceptable carrier.

A further embodiment of the present invention is a method for treating or ameliorating pain in a human subject in need thereof. This method comprises administering to the subject an effective amount of a pharmaceutical composition comprising a compound of formula VI substantially free of its R-enantiomer, which compound is non-addictive to the subject:

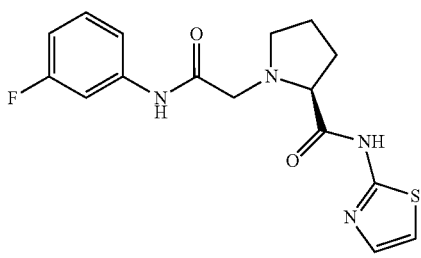

VI and a pharmaceutically acceptable carrier.

An additional embodiment of the present invention is a method for treating pain in a subject. This method comprises administering to the subject an effective amount of a non-addictive pharmaceutical composition comprising a pharmaceutically acceptable carrier and a compound of formula I:

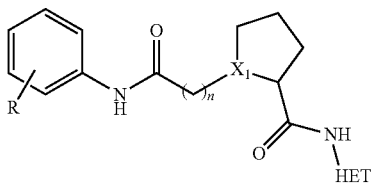

I wherein
$X_1$ is selected from the group consisting of N, O, and S;
n is an integer between 1 and 10;
HET is a heteroaromatic ring; and
R is a halogen atom or —$C_{1-4}$alkylhalo; or
crystalline forms, hydrates, or salts thereof;
further wherein the compound is biased toward G protein activation over arrestin.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows that only MCKK-17-R/S exhibited agonistic activity at the hKOP receptor, and that MCKK-17S was the more active stereoisomer. FIG. 1B shows that MCKK-17S is selective for hKOP relative to MOP and DOP receptors. In FIG. 1C, the hKOP receptor was co-expressed with a BRET-based CAMYEL sensor to assay inhibition of forskolin-stimulated cAMP accumulation. In FIG. 1D, The hKOP receptor, fused to RLuc8, was co-expressed with arrestin3 (Arr3) fused to mVenus to assay arrestin recruitment to the activated receptor. Error bars in FIG. 1 indicate standard of error (S.E.).

DETAILED DESCRIPTION OF THE INVENTION

Figure 1:
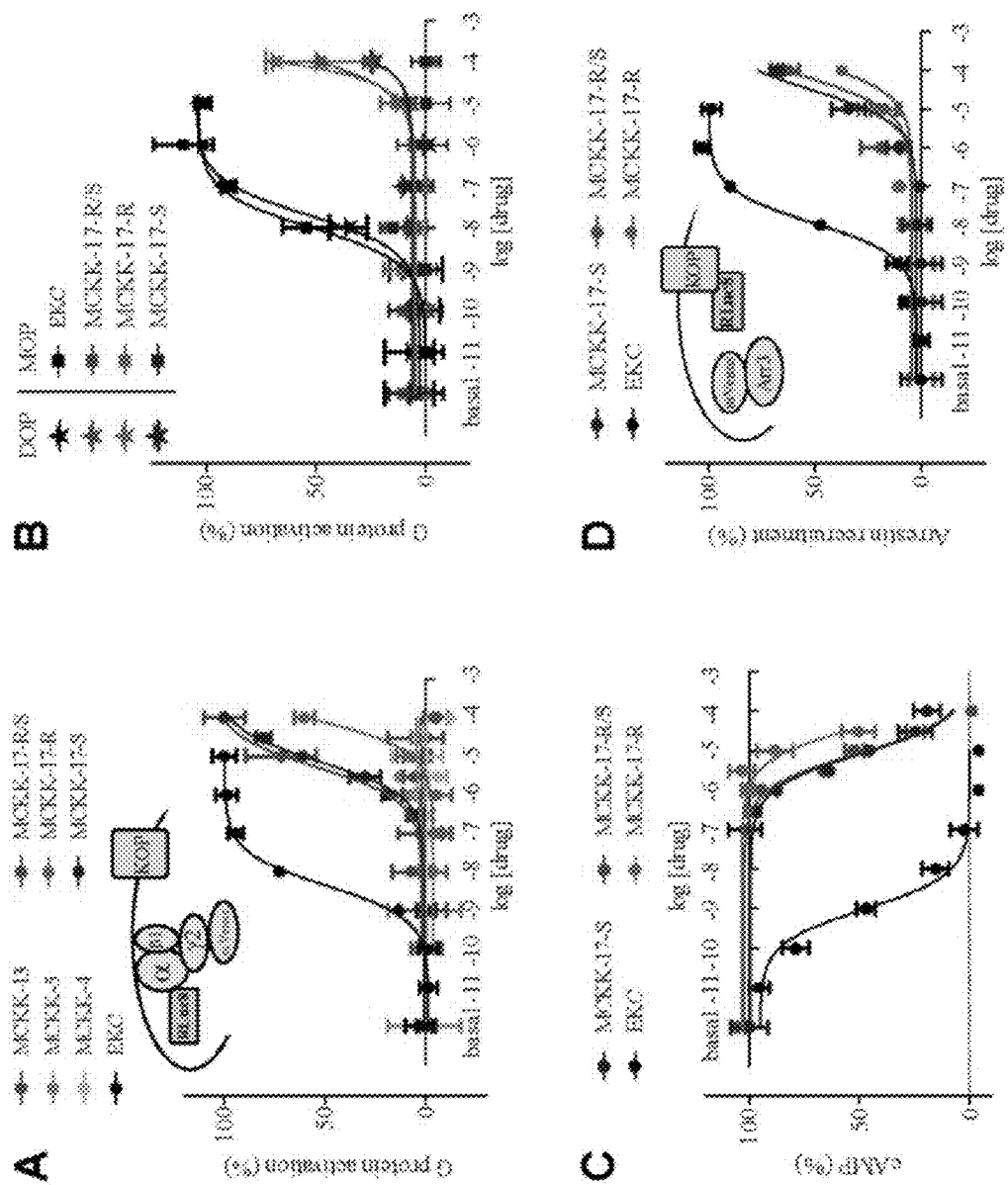
FIG. 1 shows that MCKK-17-S is a selective hKOP receptor agonist. The hKOP receptor (FIG. 1A), DOP or MOP receptors (FIG. 1B) were co-expressed with $G\alpha_{oB}$-RLuc8, β1, and mVenus-γ2 to assay G protein activation.

One embodiment of the present invention is a compound of formula I:

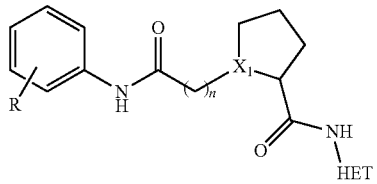

I wherein
$X_1$ is selected from the group consisting of N, O, and S;
n is an integer between 1 and 10;
HET is a heteroaromatic ring; and
R is a halogen atom or —$C_{1-4}$alkylhalo; or
crystalline forms, hydrates, or salts thereof.

As used herein, the term "heteroaromatic ring" includes substituted or unsubstituted aromatic single ring structures, preferably 3- to 8-membered rings, more preferably 5- to 7-membered rings, even more preferably 5- to 6-membered rings, whose ring structures include at least one heteroatom, preferably one to four heteroatoms, more preferably two heteroatoms. The term "heteroaromatic ring" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaromatic rings include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur. The term "aromatic" means characterized by increased chemical stability resulting from the delocalization of electrons in a ring system containing, e.g., one or more conjugated double bonds.

The terms "halo" and "halogen" are used interchangeably herein and mean halogen atoms and include chloro, fluoro, bromo, and iodo.

As used herein, the term "alkylhalo" means alkyl substituted with at least one halogen. Non-limiting examples of haloalkyl include trifluoromethyl and 2,2,2-trifluoroethyl. The term "alkyl" refers to the radical of saturated aliphatic groups, including straight-chain alkyl groups, branched-chain alkyl groups, and cycloalkyl groups. In preferred embodiments, a straight chain or branched chain alkyl has 4 or fewer carbon atoms in its backbone (e.g., $C_1$-$C_4$ for straight chains, $C_3$-$C_4$ for branched chains).

The term "$C_{x-y}$" when used in conjunction with a chemical moiety, such as, alkyl, is meant to include groups that contain from x to y carbons in the chain.

Preferably, the compound of formula I is the S enantiomer:

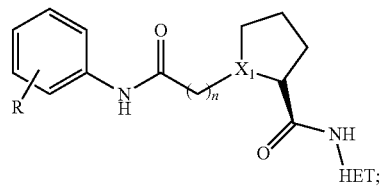

or crystalline forms, hydrates, or salts thereof. More preferably, the compound of formula I is substantially free of its R-enantiomer.

As used herein, "substantially free" means a presence of the other enantiomer in a concentration of at the most about 10%, e.g., at most about 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, or a complete absence of the other enantiomer.

Another embodiment of the present invention is a compound of formula II:

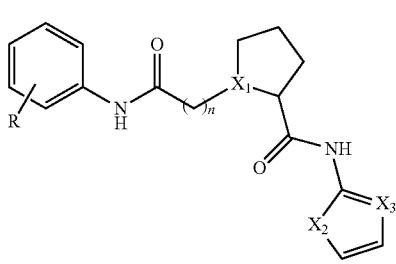

II wherein
$X_1$, $X_2$, and $X_3$ are independently selected from the group consisting of N, O, and S;
n is an integer between 1 and 10; and
R is a halogen atom or —$C_{1-4}$alkylhalo; or
crystalline forms, hydrates, or salts thereof.

Preferably, the compound of formula II is the S enantiomer:

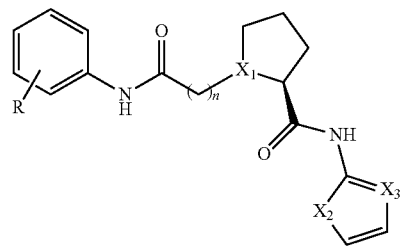

or crystalline forms, hydrates, or salts thereof. More preferably, the compound of formula II is substantially free of its R-enantiomer.

A further embodiment of the present invention is compound of formula III:

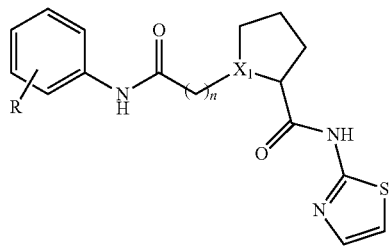

III wherein
X₁ is selected from the group consisting of N, O, and S;
n is an integer between 1 and 10; and
R is a halogen atom or —$C_{1-4}$alkylhalo; or
crystalline forms, hydrates, or salts thereof.

Preferably, the compound of formula III is the S enantiomer:

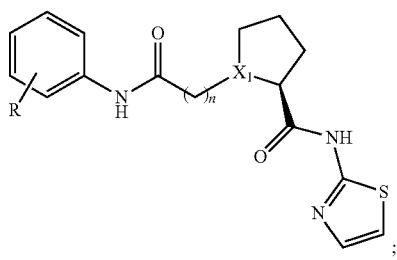

;

or crystalline forms, hydrates, or salts thereof. More preferably, the compound of formula III is substantially free of its R-enantiomer.

Another embodiment of the present invention is a compound of formula IV:

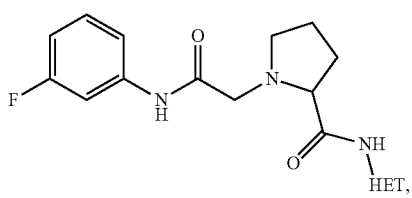

IV wherein
HET is a heteroaromatic ring, or
crystalline forms, hydrates, or salts thereof.

Preferably, the compound of formula IV is the S enantiomer:

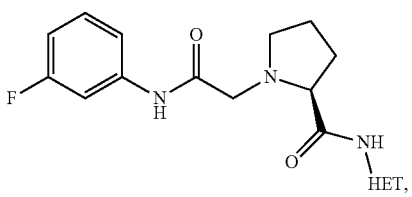

or crystalline forms, hydrates, or salts thereof. More preferably, the compound of formula IV is substantially free of its R-enantiomer.

An additional embodiment of the present invention is a compound of formula V:

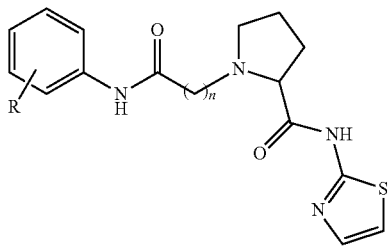

V wherein
n is selected from an integer between 1 and 10; and
R is a halogen atom or —$C_{1-4}$alkylhalo; or
crystalline forms, hydrates, or salts thereof.

Preferably, the compound of formula V is the S enantiomer:

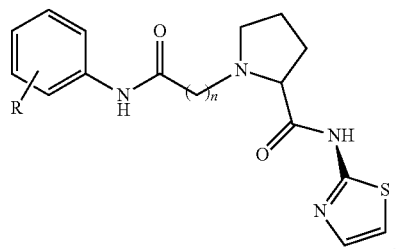

, or crystalline forms, hydrates, or salts thereof. More preferably, the compound of formula V is substantially free of its R-enantiomer.

Another embodiment of the present invention is a compound of formula VI substantially free of its R-enantiomer:

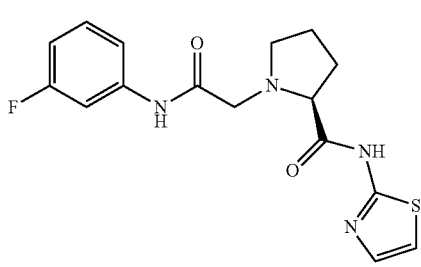

VI

., or crystalline forms, hydrates, or salts thereof.

An additional embodiment of the present invention is a compound of the structure:

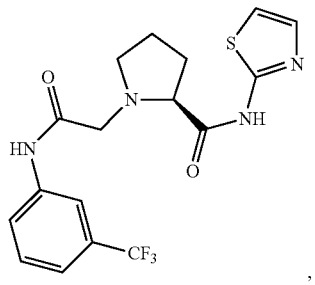 [SMILES: O=C(CN1CCC[C@H]1C(=O)Nc1nccs1)Nc1cccc(C(F)(F)F)c1]

or crystalline forms, hydrates, or salts thereof. Preferably, this compound is substantially free of its R-enantiomer.

A further embodiment of the present invention is any compound disclosed herein, which selectively activates a Kappa Opioid Receptor (KOP) over a Delta Opioid Receptor (DOP) or over a Mu Opioid Receptor (MOP) and is biased toward G protein activation over arrestin.

As used herein, to "activate", "activation", or other grammatical variations thereof, as applied to a protein, mean to turn on the protein. For example, activation of a receptor causes stimulatory changes in the cell. In another example, G proteins, when activated, bind guanosine triphosphate (GTP) rather than guanosine diphosphate (GDP) and cause a cascade of transcriptional changes.

As used herein, to "selectively" activate means preferential activation of one protein over another. For example, a compound may activate one protein, more than 1 fold, such as greater than 2 fold, 3 fold, 4 fold, 5 fold, 6 fold, 7 fold, 8 fold, 9 fold, 10 fold, 20 fold, 30 fold, 40 fold, 50 fold, 100 fold, 200 fold, 300 fold, 400 fold, 500 fold, or 1000 fold, in comparison to its activation of the other protein.

As used herein, "biased" means tending to have one outcome rather than a different one.

Another embodiment of the present invention is a pharmaceutical composition comprising any compound disclosed herein and a pharmaceutically acceptable carrier.

A further embodiment of the present invention is a pharmaceutical composition comprising a compound of formula VI substantially free of its R-enantiomer:

VI

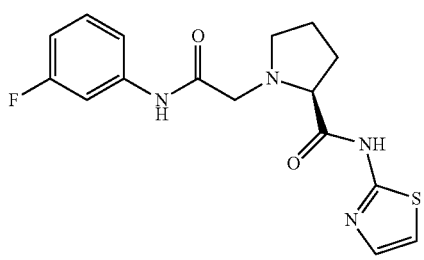

and a pharmaceutically acceptable carrier.

Another embodiment of the present invention is a pharmaceutical composition comprising compound of the structure

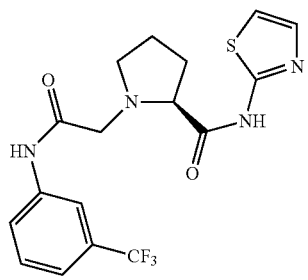 [SMILES: O=C(CN1CCC[C@H]1C(=O)Nc1nccs1)Nc1cccc(C(F)(F)F)c1]

and a pharmaceutically acceptable carrier. Preferably, the compound is substantially free from its R-enantiomer.

A further embodiment of the present invention is a method for treating or ameliorating the effects of a condition in a subject in need thereof. This method comprises administering to the subject an effective amount of any compound disclosed herein.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject, e.g., patient, population. Accordingly, a given subject or subject, e.g., patient, population may fail to respond or respond inadequately to treatment.

As used herein, the terms "ameliorate", "ameliorating" and grammatical variations thereof mean to decrease the severity of the symptoms of a disease in a subject.

As used herein, a "subject" is a mammal, preferably, a human. In addition to humans, categories of mammals within the scope of the present invention include, for example, agricultural animals, domestic animals, laboratory animals, etc. Some examples of agricultural animals include cows, pigs, horses, goats, etc. Some examples of domestic animals include dogs, cats, etc. Some examples of laboratory animals include rats, mice, rabbits, guinea pigs, etc.

In the present invention, an "effective amount" or "therapeutically effective amount" of a compound or a pharmaceutical composition is an amount of such an inhibitor that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of a compound or a pharmaceutical composition according to the invention will be that amount of the compound or the pharmaceutical composition, which is the lowest dose effective to produce the desired effect with no or minimal side effects. The effective dose of a compound or a pharmaceutical composition may be administered as two, three, four, five, six or more sub-doses, administered separately at appropriate intervals throughout the day.

A suitable, non-limiting example of a dosage of a compound or a pharmaceutical composition according to the present invention is from about 1 ng/kg to about 1000 mg/kg, such as from about 1 mg/kg to about 100 mg/kg, including from about 5 mg/kg to about 50 mg/kg. Other representative dosages of a compound or a pharmaceutical composition include about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, or 1000 mg/kg.

The condition may be pain, coughing, depression, or itching.

An additional embodiment of the present invention is a method for treating or ameliorating the effects of a condition in a subject in need thereof. This method comprises administering to the subject an effective amount of any pharmaceutical composition disclosed herein.

In this embodiment, appropriate and preferred subjects are as set forth above. The condition may be pain, coughing, depression, or itching.

Another embodiment of the present invention is a method for treating or ameliorating the effects of a condition in a subject in need thereof. This method comprises administering to the subject an effective amount of a pharmaceutical composition comprising a compound of formula VI substantially free of its R-enantiomer:

VI

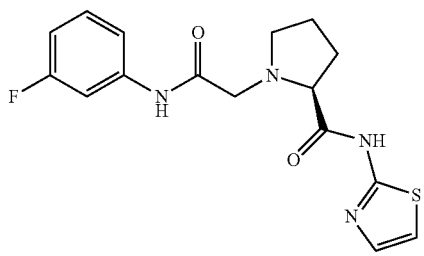

and a pharmaceutically acceptable carrier.

In this embodiment, appropriate and preferred subjects are as set forth above. The condition may be pain, coughing, depression, or itching.

A further embodiment of the present invention is a method for treating or ameliorating pain in a human subject in need thereof. This method comprises administering to the subject an effective amount of a pharmaceutical composition comprising a compound of formula VI substantially free of its R-enantiomer, which compound is non-addictive to the subject:

VI

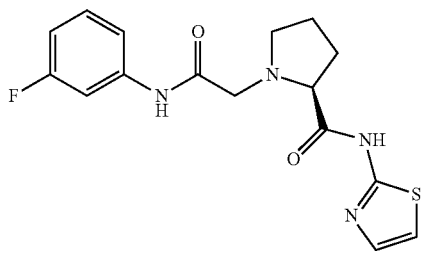

and a pharmaceutically acceptable carrier.

As used herein, "non-addictive" substances means those that do not lead to a primary, chronic disease of brain reward, motivation, memory and related circuitry, which is reflected in an individual pathologically pursuing reward and/or relief by substance use and other behaviors. Addictive substances include opioid drugs that act as agonists at the MOP receptor.

In this embodiment, appropriate and preferred subjects are as set forth above. The condition may be pain, coughing, depression, or itching.

An additional embodiment of the present invention is a method for treating pain in a subject. This method comprises administering to the subject an effective amount of a non-addictive pharmaceutical composition comprising a pharmaceutically acceptable carrier and a compound of formula I:

I

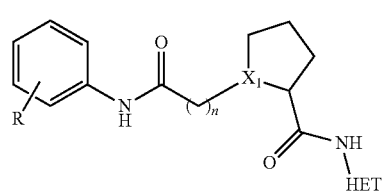

wherein
$X_1$ is selected from the group consisting of N, O, and S;
n is an integer between 1 and 10;
HET is a heteroaromatic ring; and
R is a halogen atom or —$C_{1-4}$alkylhalo; or
crystalline forms, hydrates, or salts thereof;
further wherein the compound is biased toward G protein activation over arrestin.

In this embodiment, appropriate and preferred subjects and compounds of formula I are as set forth above. The condition may be pain, coughing, depression, or itching.

It is understood that the disclosure of a compound herein encompasses all stereoisomers of that compound. As used herein, the term "stereoisomer" refers to a compound made up of the same atoms bonded by the same bonds but having different three-dimensional structures which are not interchangeable. The three-dimensional structures are called configurations. Stereoisomers include enantiomers, optical isomers, and diastereomers.

The terms "racemate" or "racemic mixture" refer to a mixture of equal parts of enantiomers. The term "chiral center" refers to a carbon atom to which four different groups are attached. The term "enantiomeric enrichment" as used herein refers to the increase in the amount of one enantiomer as compared to the other.

It is appreciated that compounds of the present invention having a chiral center may exist in and be isolated in optically active and racemic forms. Some compounds may exhibit polymorphism. It is to be understood that the present invention encompasses any racemic, optically-active, diastereomeric, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Examples of methods to obtain optically active materials are known in the art, and include at least the following:

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts as disclosed in more detail herein or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The stereoisomers may also be separated by usual techniques known to those skilled in the art including fractional crystallization of the bases or their salts or chromatographic techniques such as LC or flash chromatography. The (+) enantiomer can be separated from the (−) enantiomer using techniques and procedures well known in the art, such as that described by J. Jacques, et al., antiomers, Racemates, and Resolutions", John Wiley and Sons, Inc., 1981. For example, chiral chromatography with a suitable organic solvent, such as ethanol/acetonitrile and Chiralpak AD packing, 20 micron can also be utilized to effect separation of the enantiomers.

A pharmaceutical composition of the present invention may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, a pharmaceutical composition of the present invention may be administered in conjunction with other treatments. A pharmaceutical composition of the present invention maybe encapsulated or otherwise protected against gastric or other secretions, if desired.

The pharmaceutical compositions of the invention are pharmaceutically acceptable and comprise one or more active ingredients in admixture with one or more pharmaceutically-acceptable carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy ($21^{st}$ Edition, Lippincott Williams and Wilkins, Philadelphia, Pa.).

Salts of the compounds disclosed herein include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like. Salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

Pharmaceutically acceptable carriers are well known in the art (see, e.g., Remington, The Science and Practice of Pharmacy (21$^{st}$ Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable carrier used in a pharmaceutical composition of the invention must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

The pharmaceutical compositions of the invention may, optionally, contain additional ingredients and/or materials commonly used in such pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Pharmaceutical compositions suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type maybe employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Pharmaceutical compositions for rectal or vaginal administration may be presented as a suppository, which maybe prepared by mixing one or more active ingredient(s) with one or more suitable nonirritating carriers which are solid at room temperature, but liquid at body temperature and, therefore, will melt in the rectum or vaginal cavity and release the active compound. Pharmaceutical compositions which are suitable for vaginal administration also include pessaries, tampons, creams, gels, pastes, foams or spray formulations containing such pharmaceutically-acceptable carriers as are known in the art to be appropriate.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable carrier. The ointments, pastes, creams and gels may contain excipients. Powders and sprays may contain excipients and propellants.

Pharmaceutical compositions suitable for parenteral administrations comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation), it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multidose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

The following examples are provided to further illustrate the methods of the present invention. These examples are illustrative only and are not intended to limit the scope of the invention in any way.

EXAMPLES

Example 1

Materials and Methods

Small-Molecule Subset, Docking, Selection, and Novelty

Figure 4:
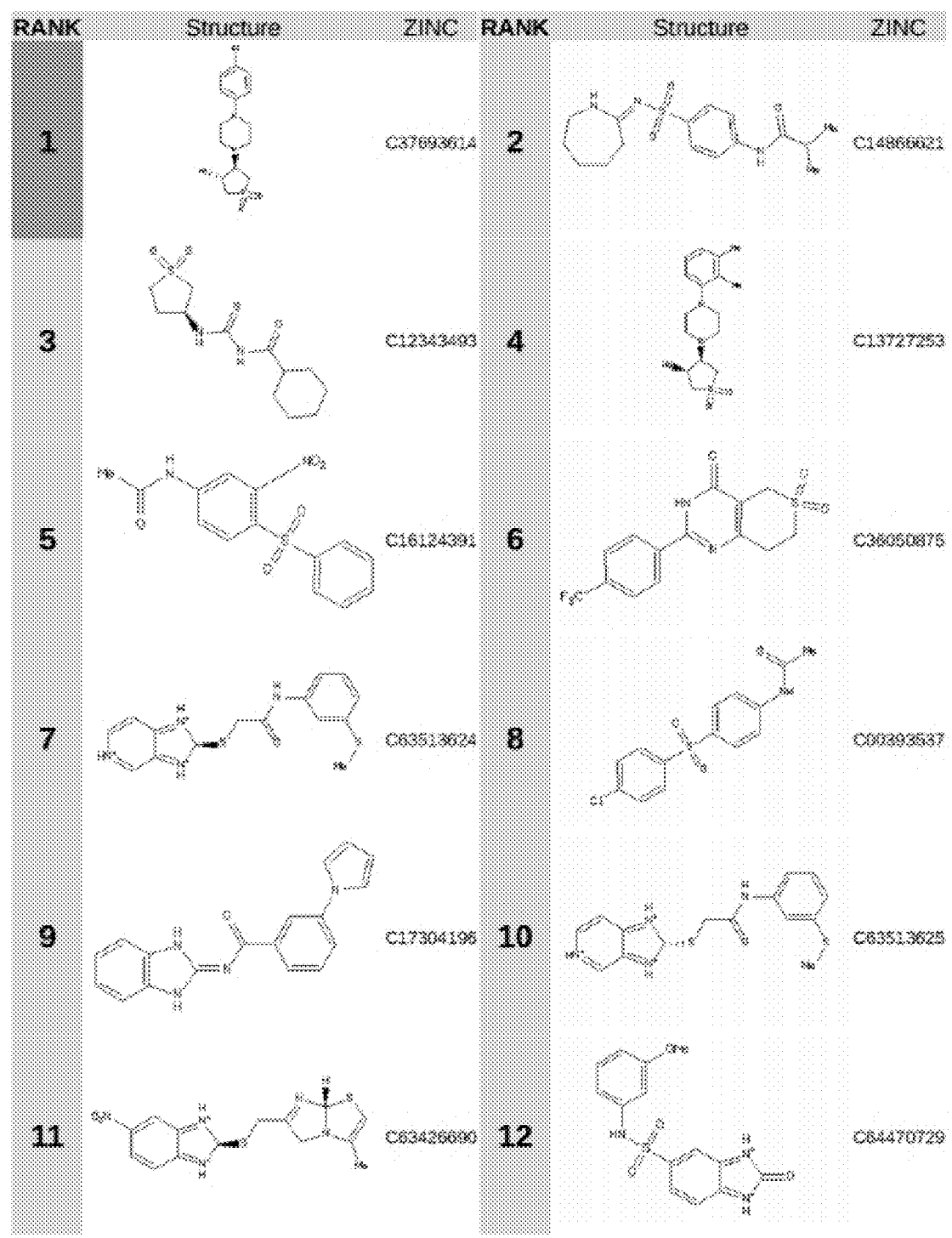
FIG. 4 shows the 500 top-scoring docked compounds from virtual screening at the KOP receptor.
Figure 4:
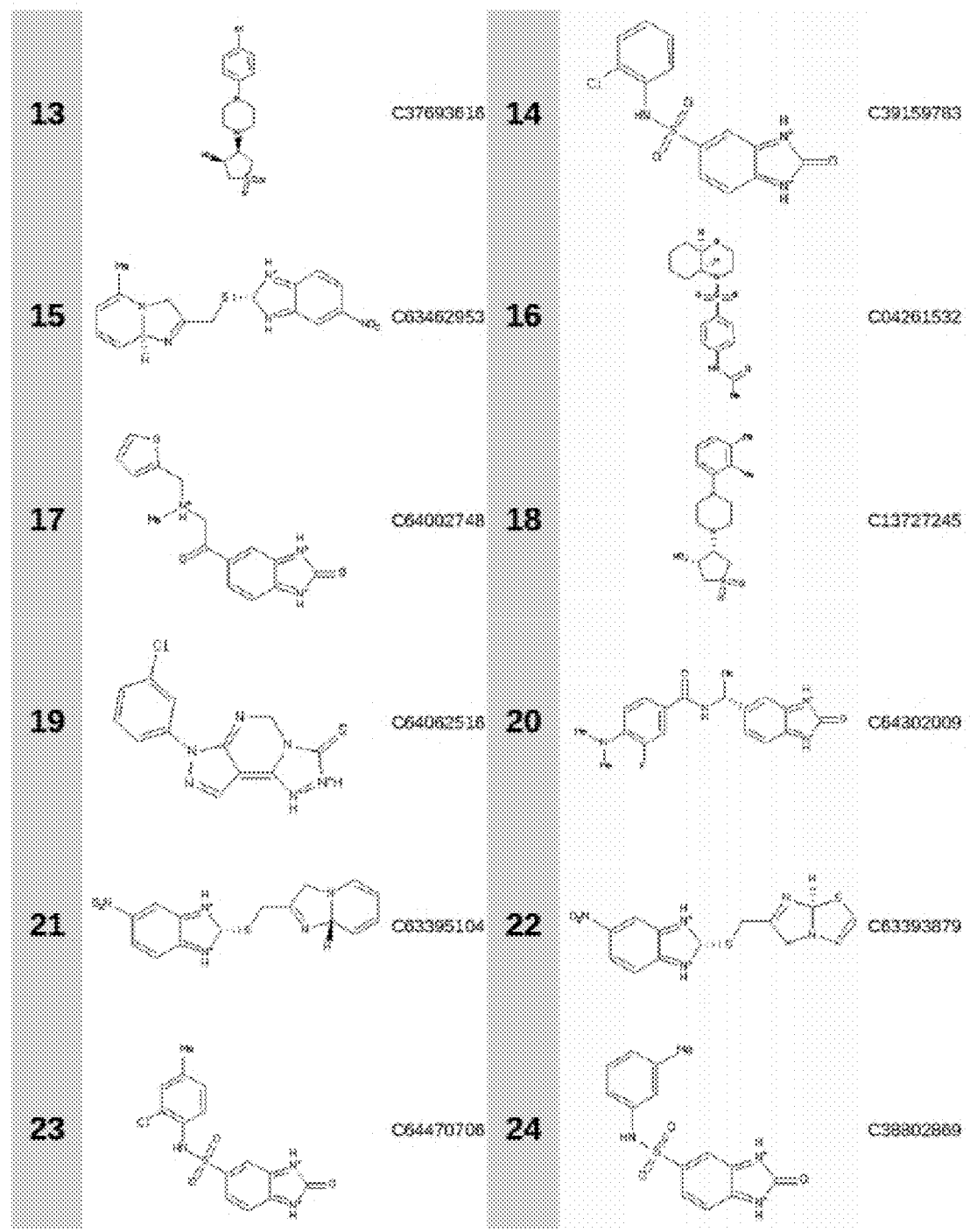
Figure 4:
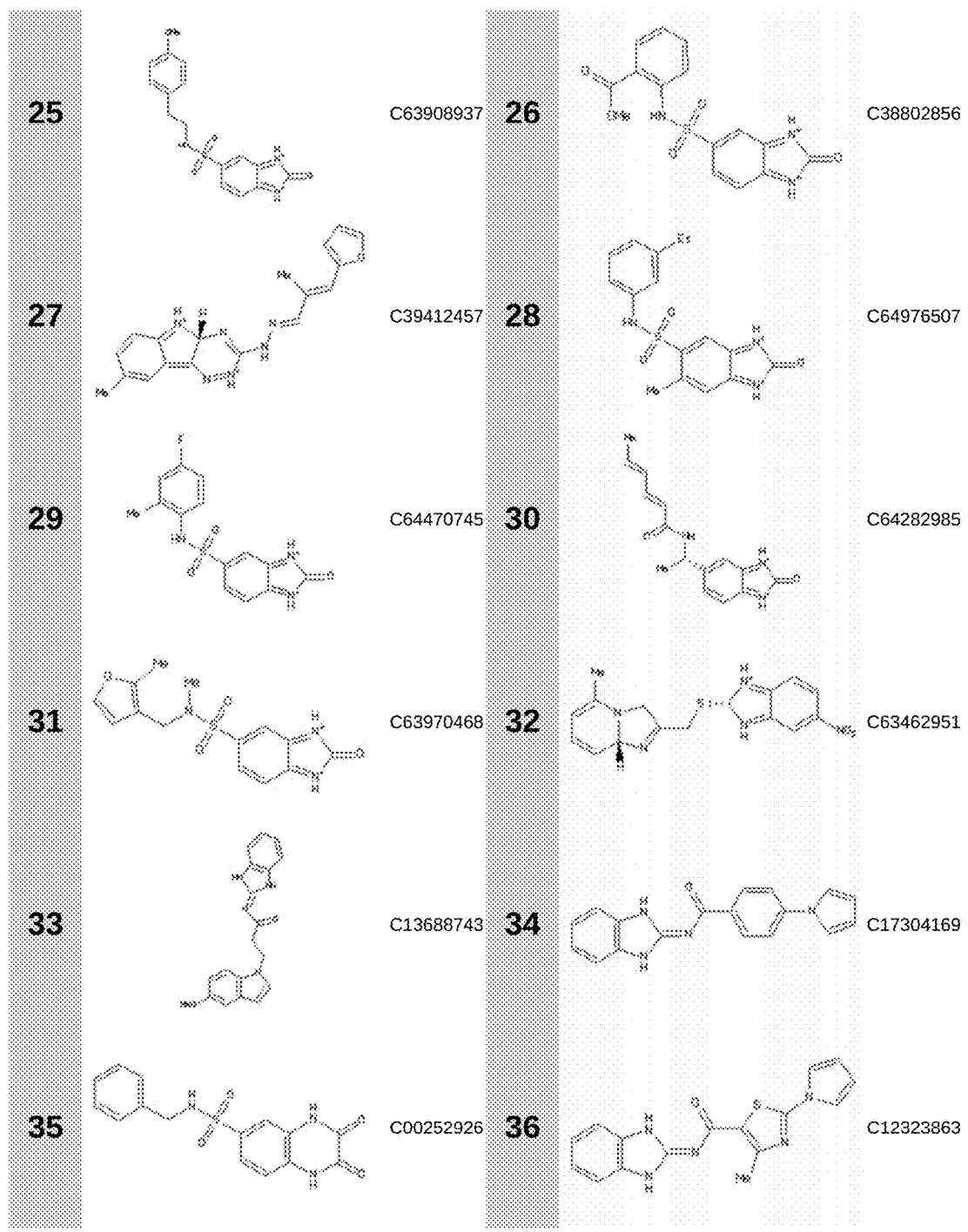
Figure 4:
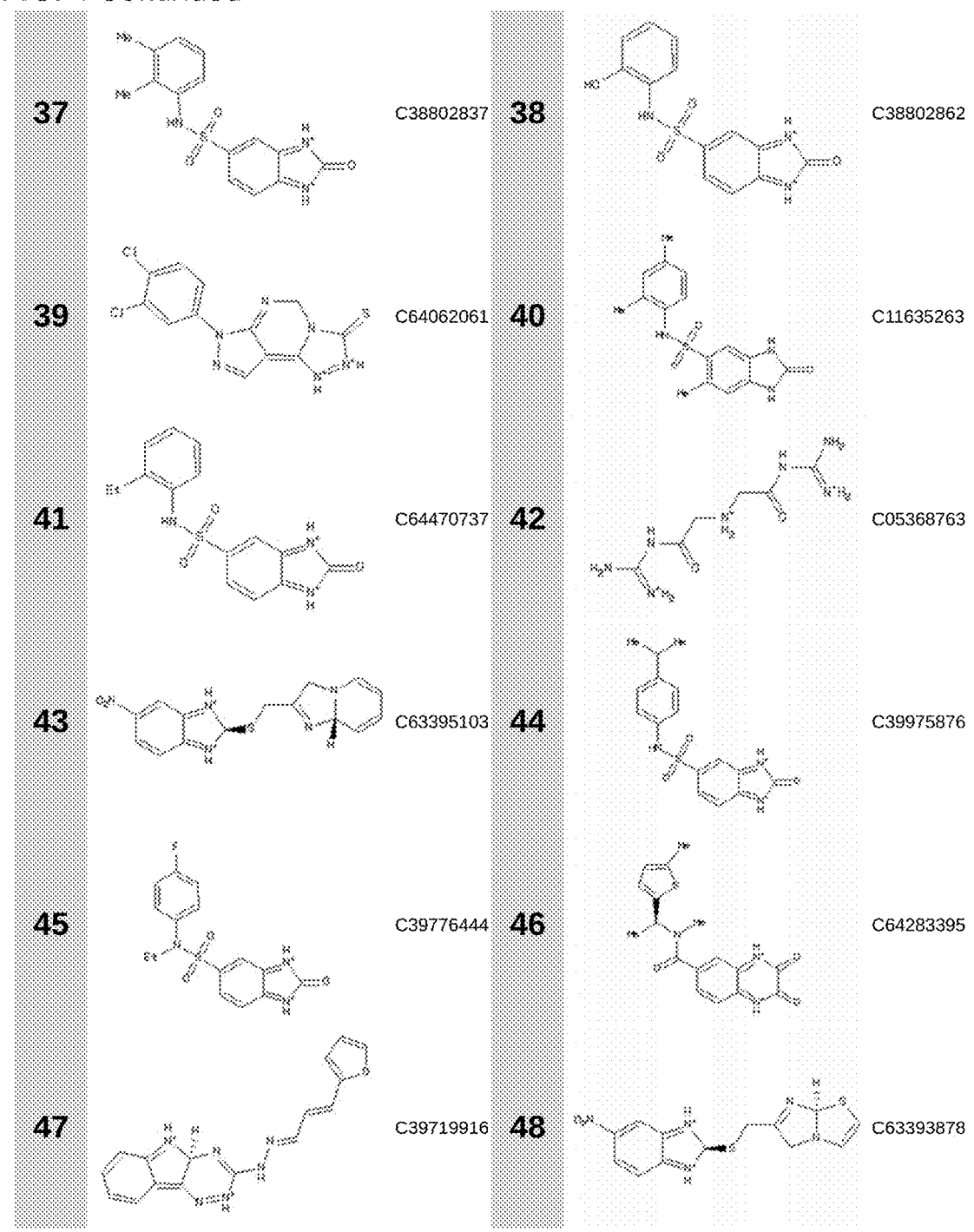
Figure 4:
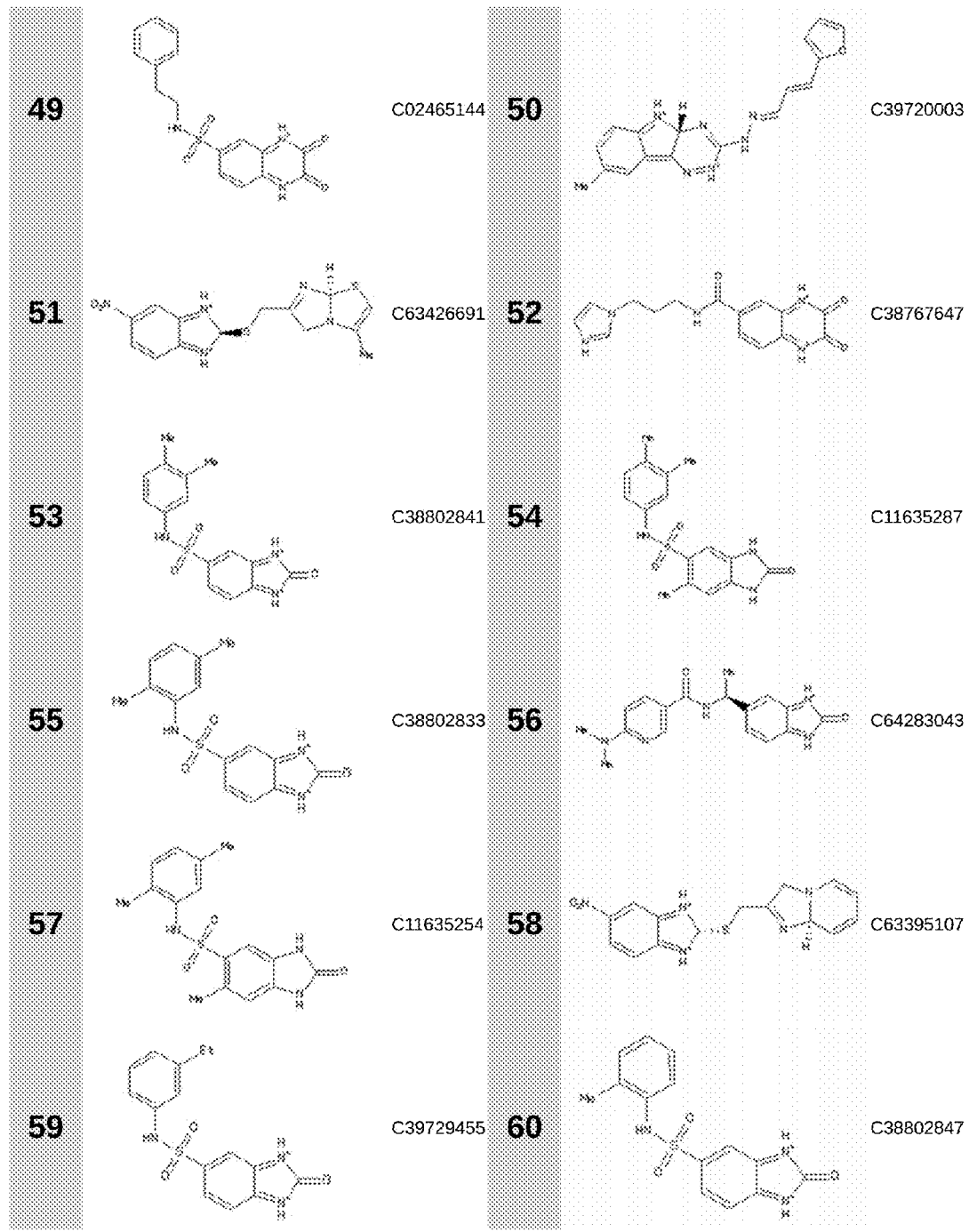
Figure 4:
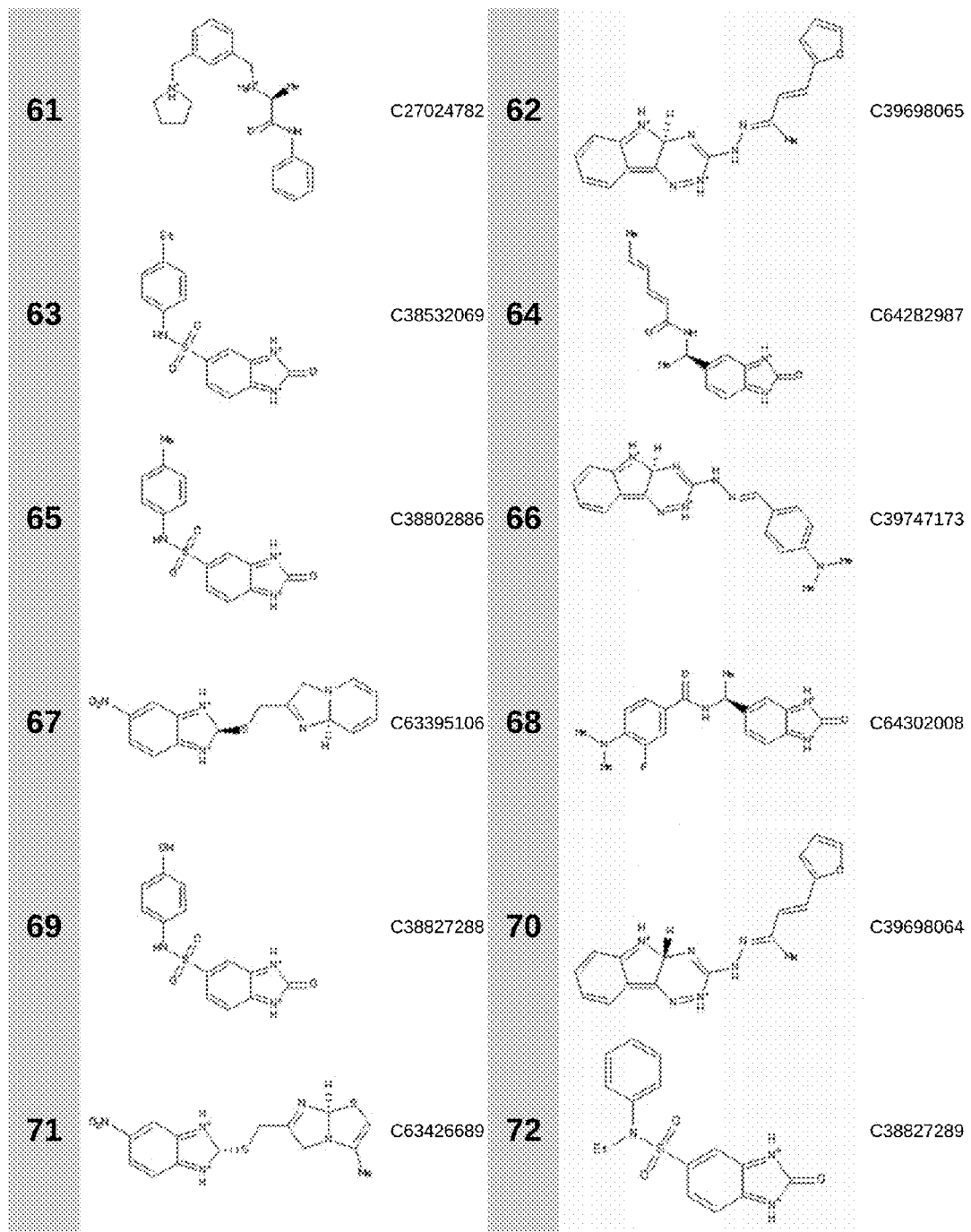
Figure 4:
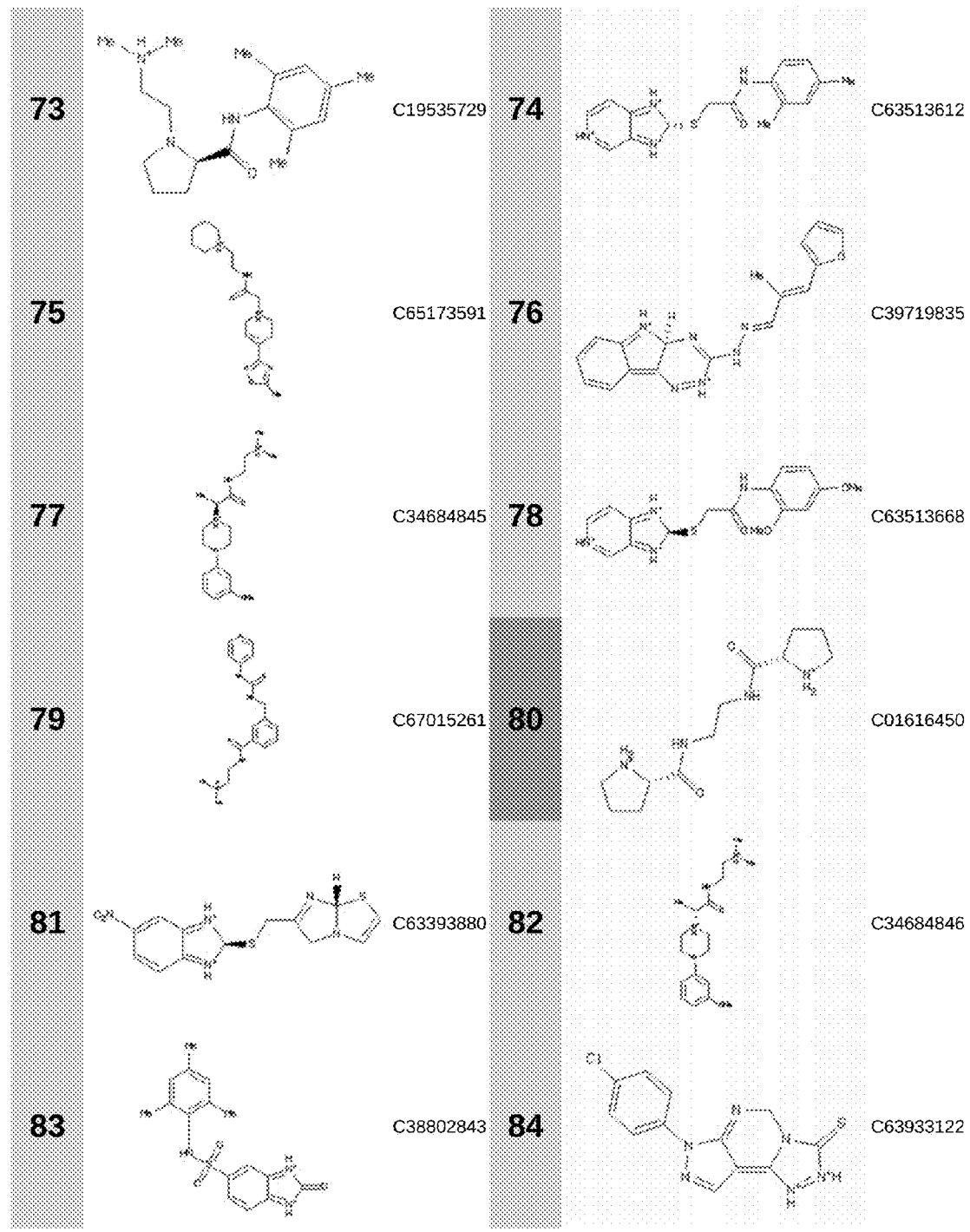
Figure 4:
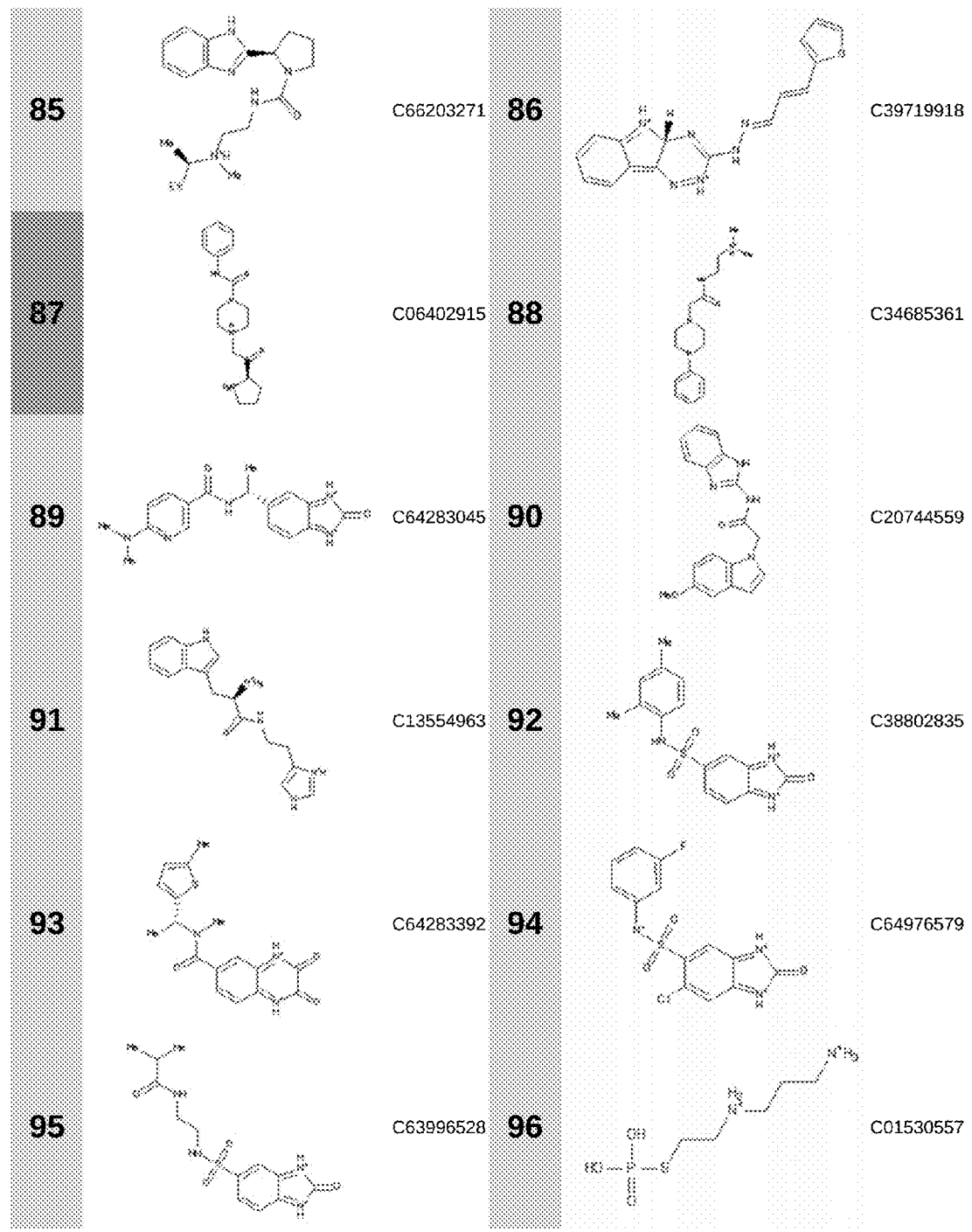
Figure 4:
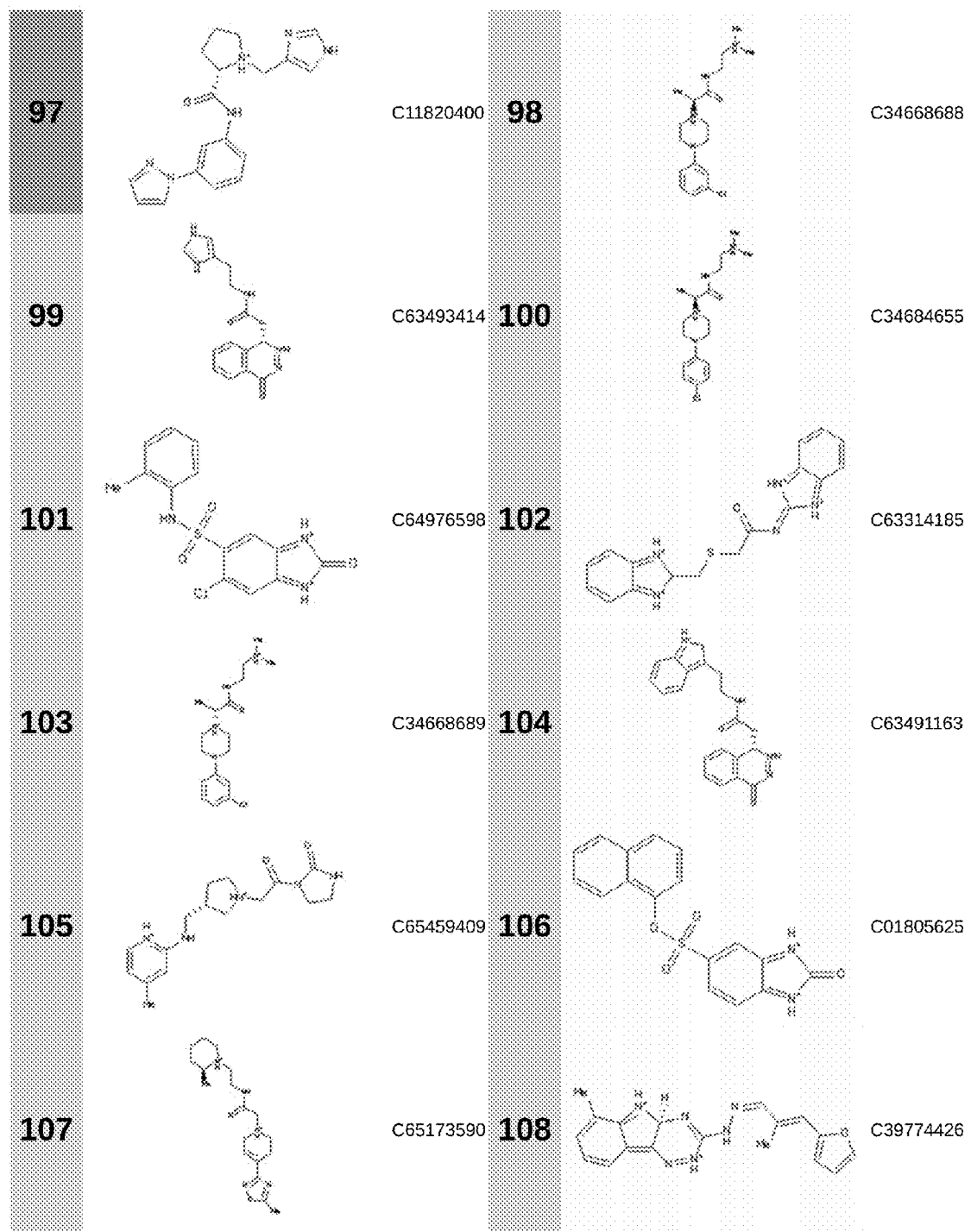
Figure 4:
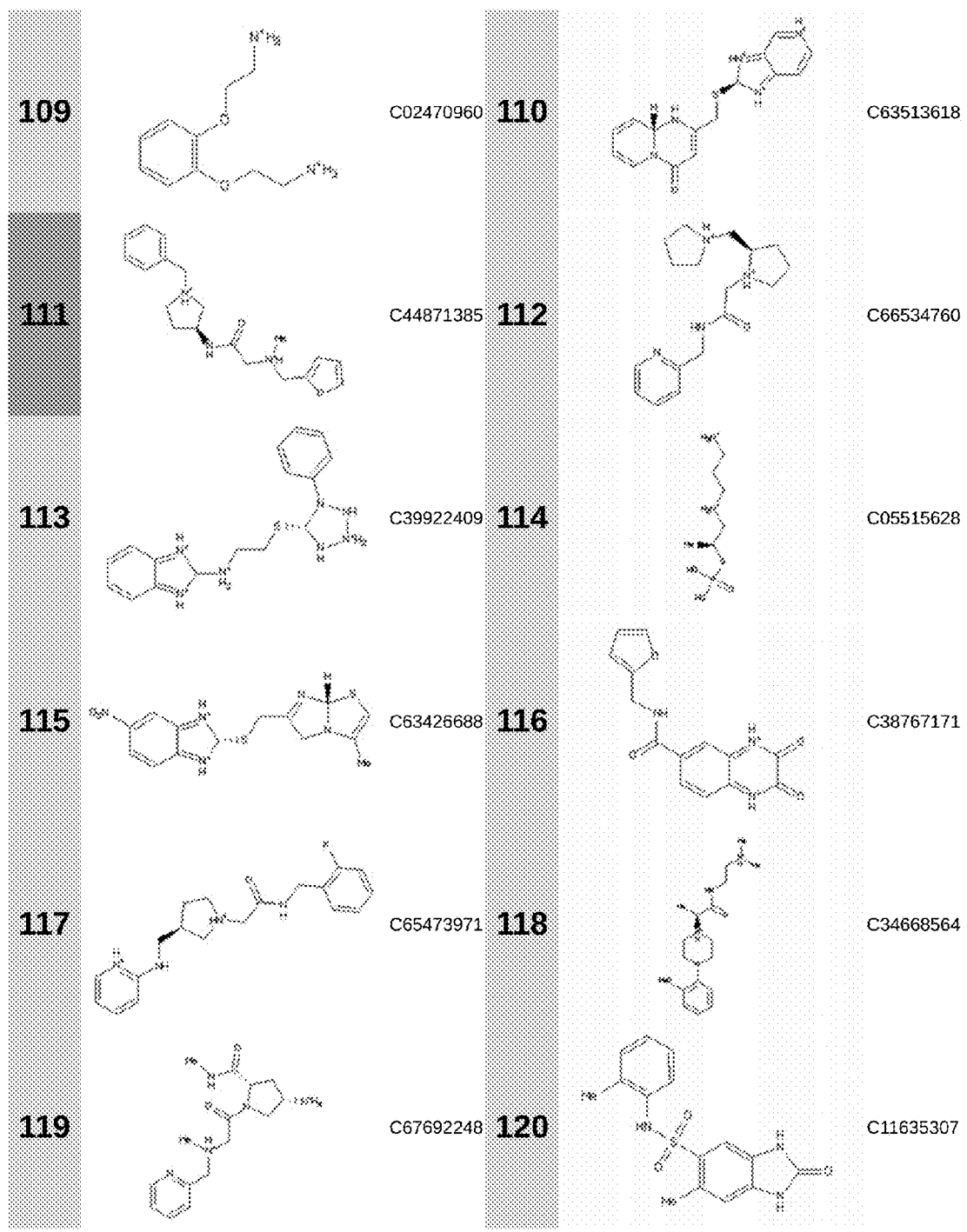
Figure 4:
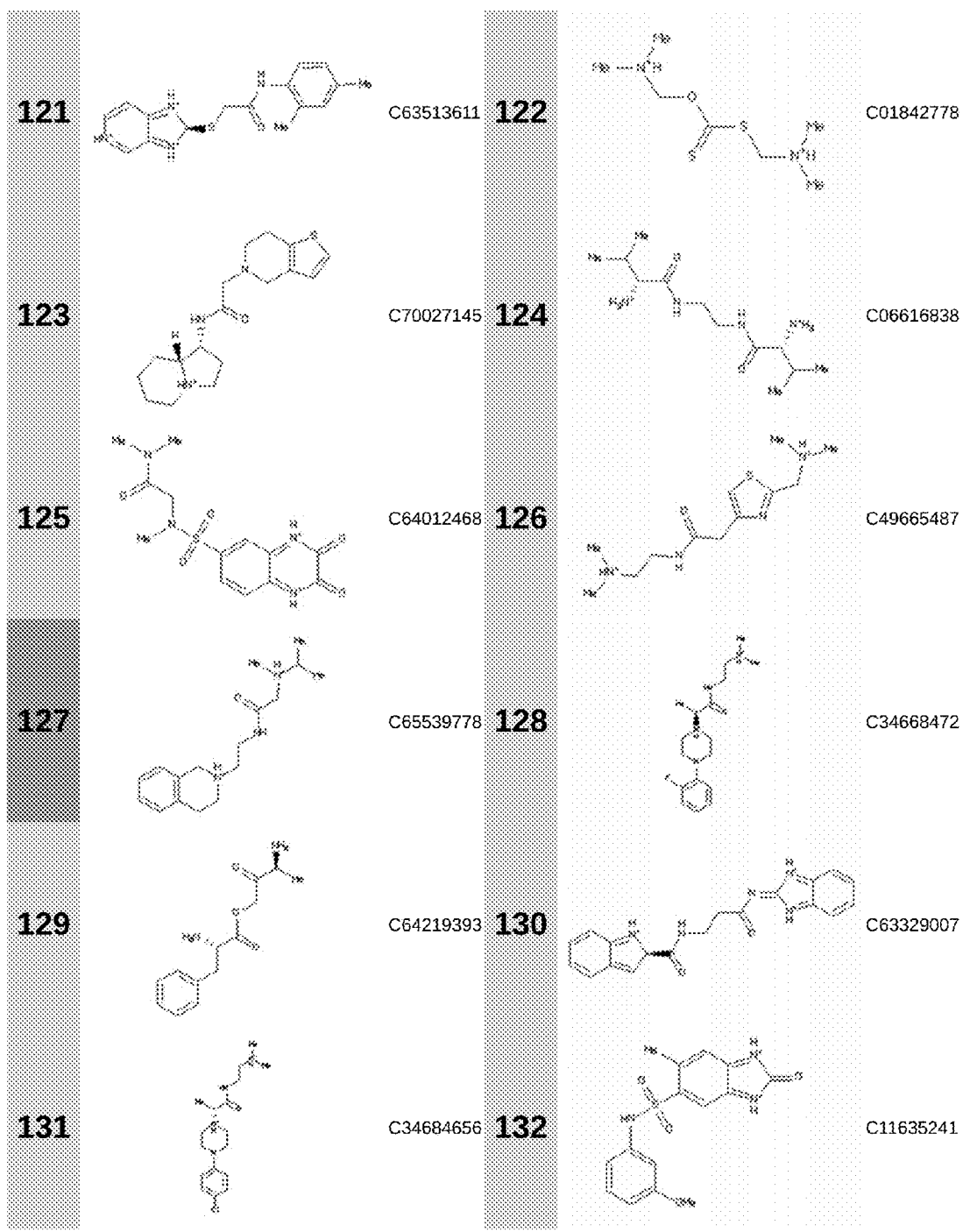
Figure 4:
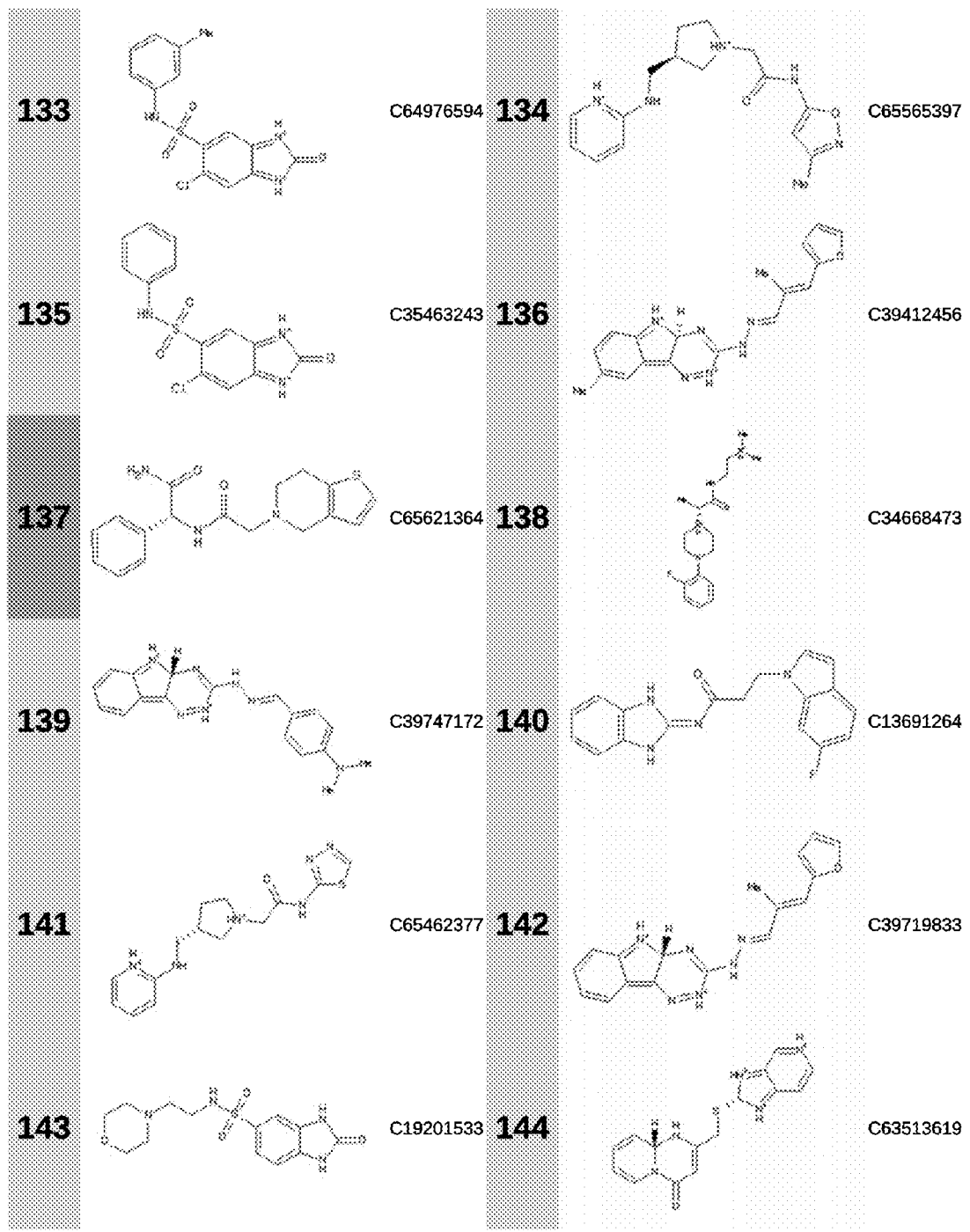
Figure 4:
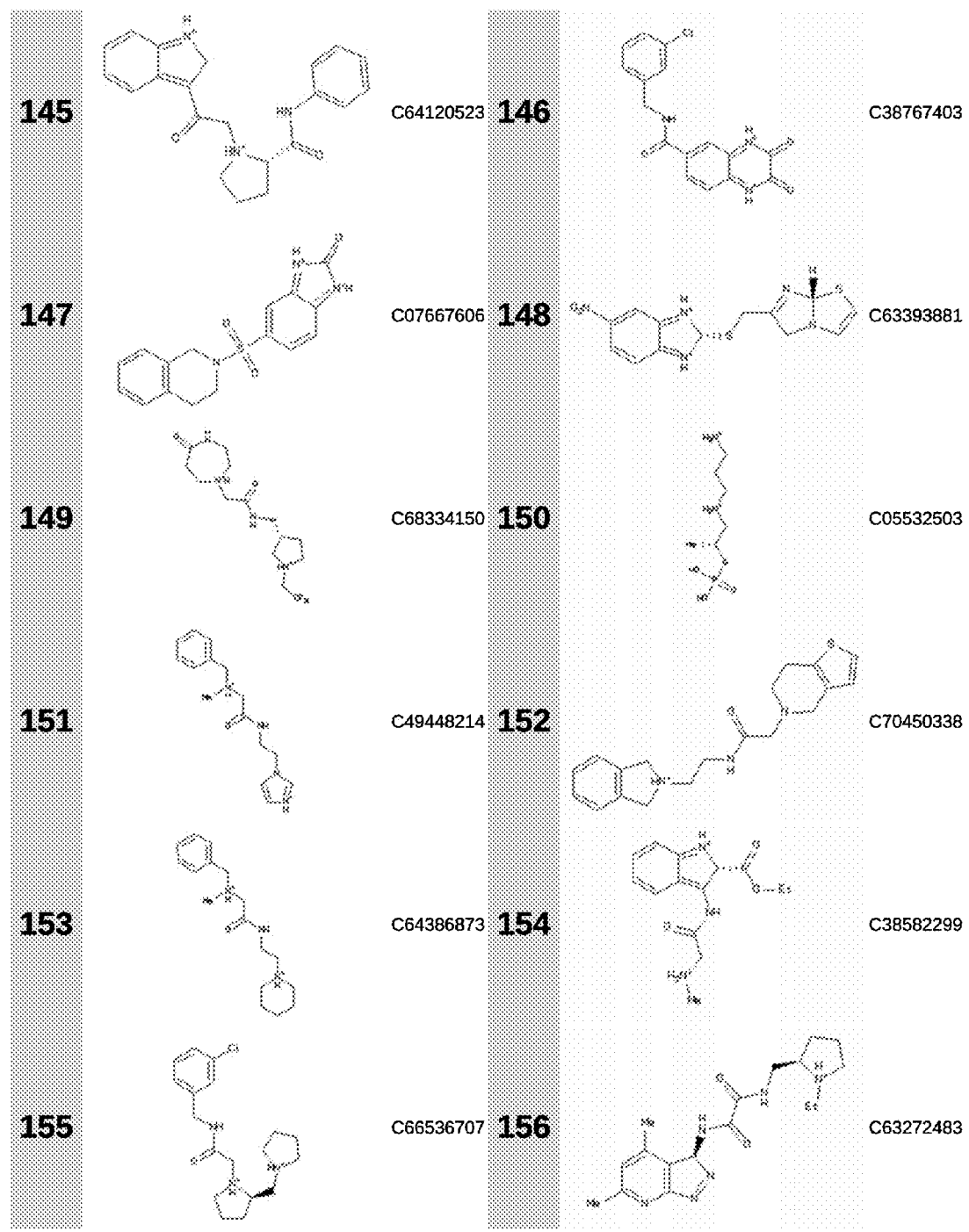
Figure 4:
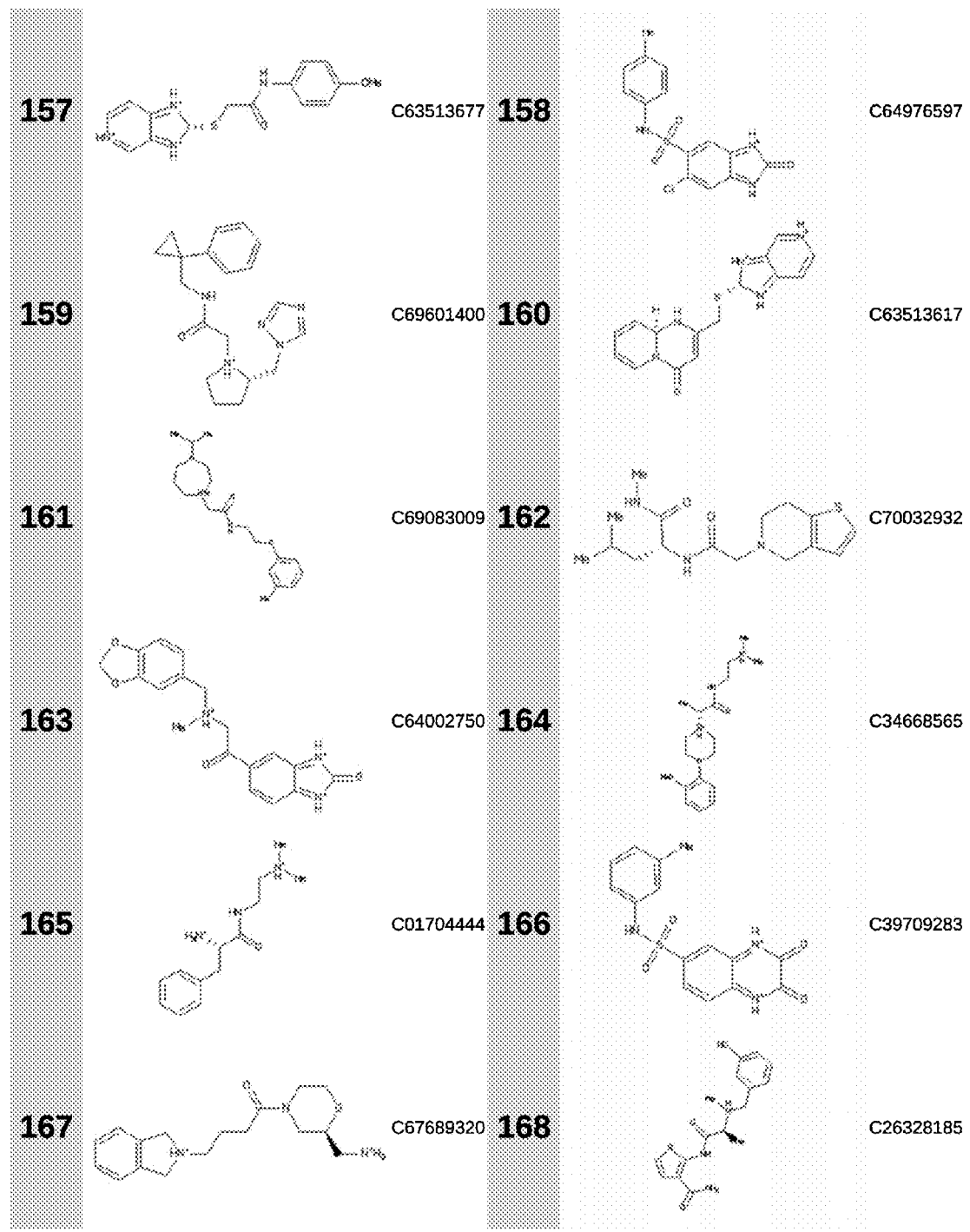
Figure 4:
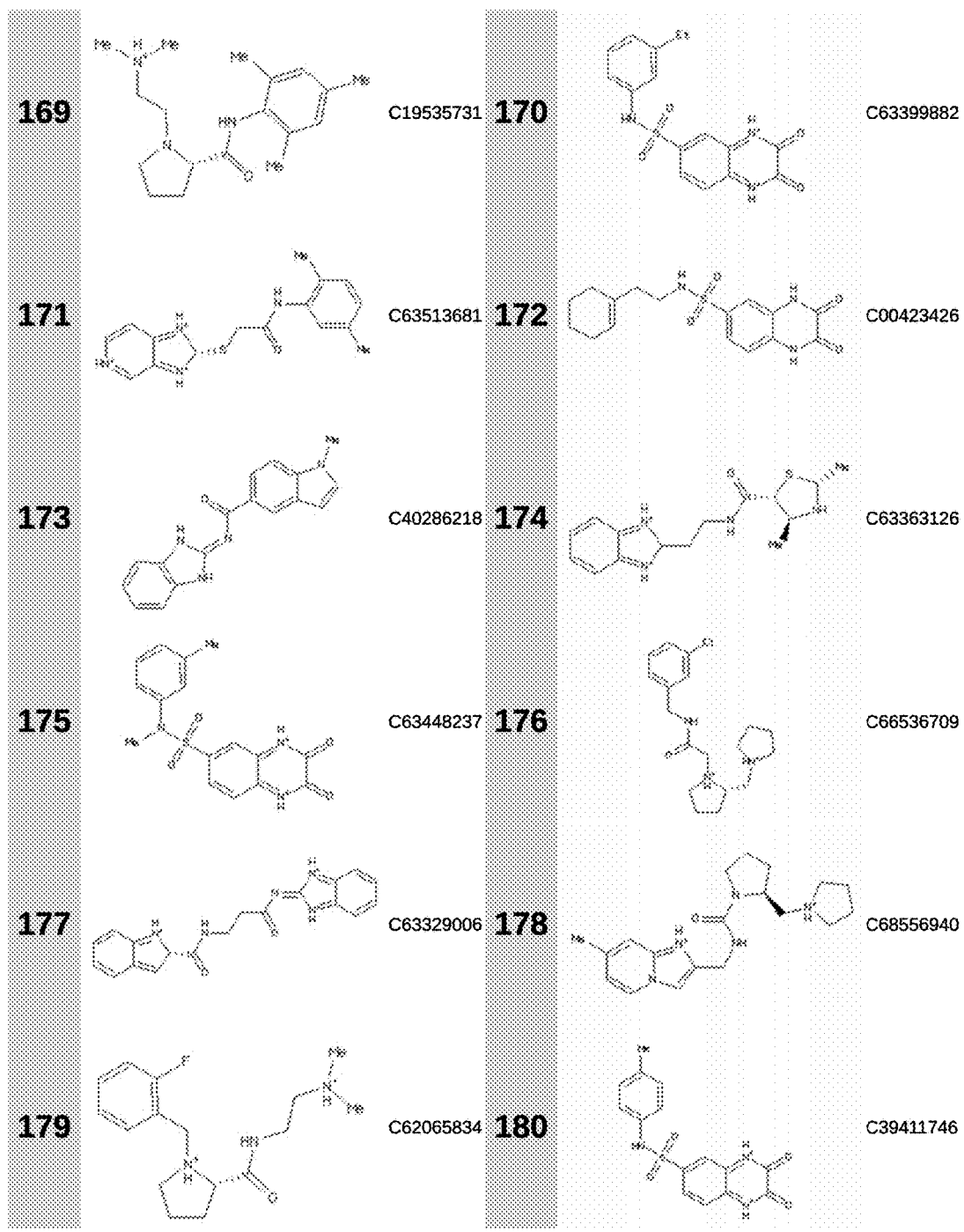
Figure 4:
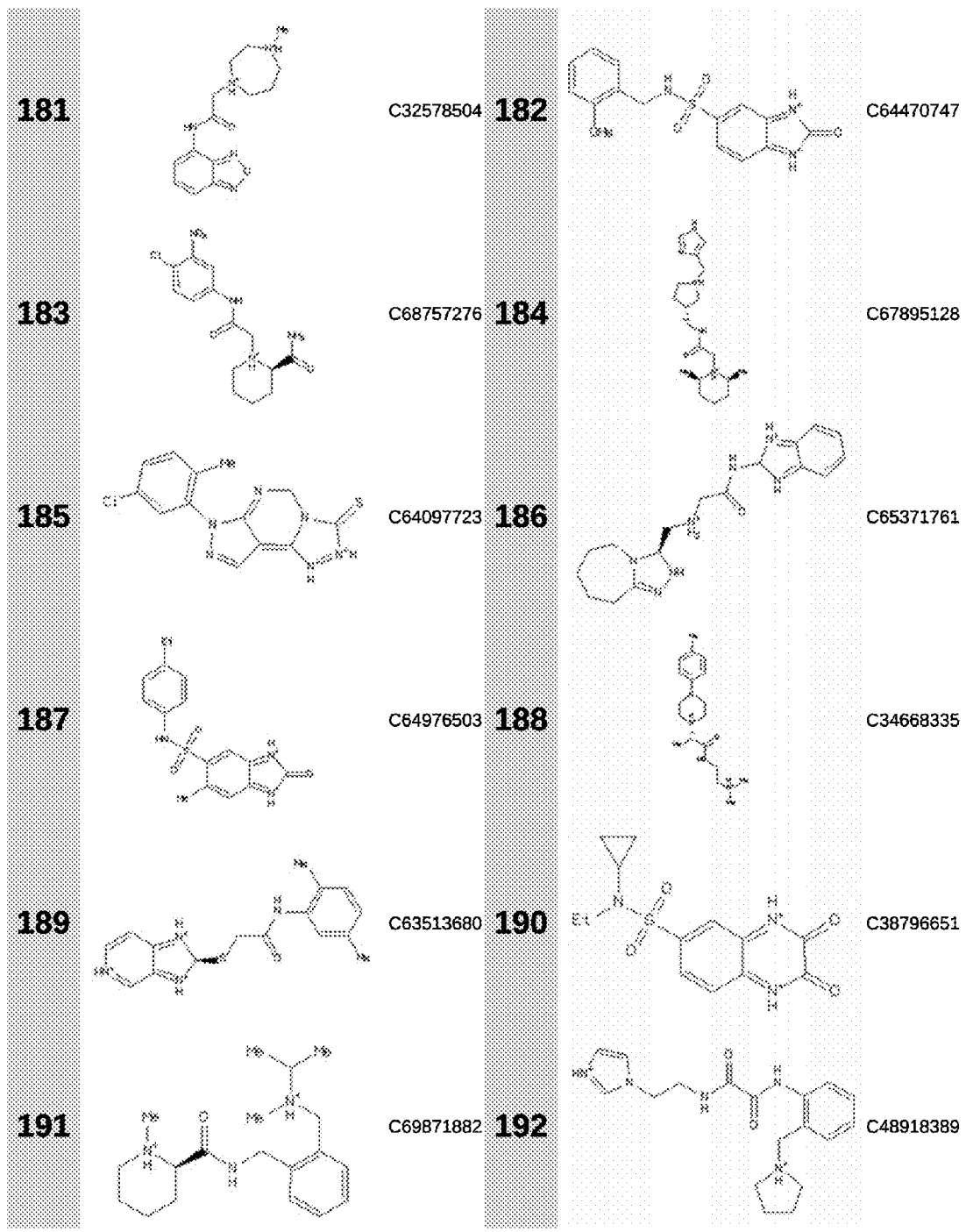
Figure 4:
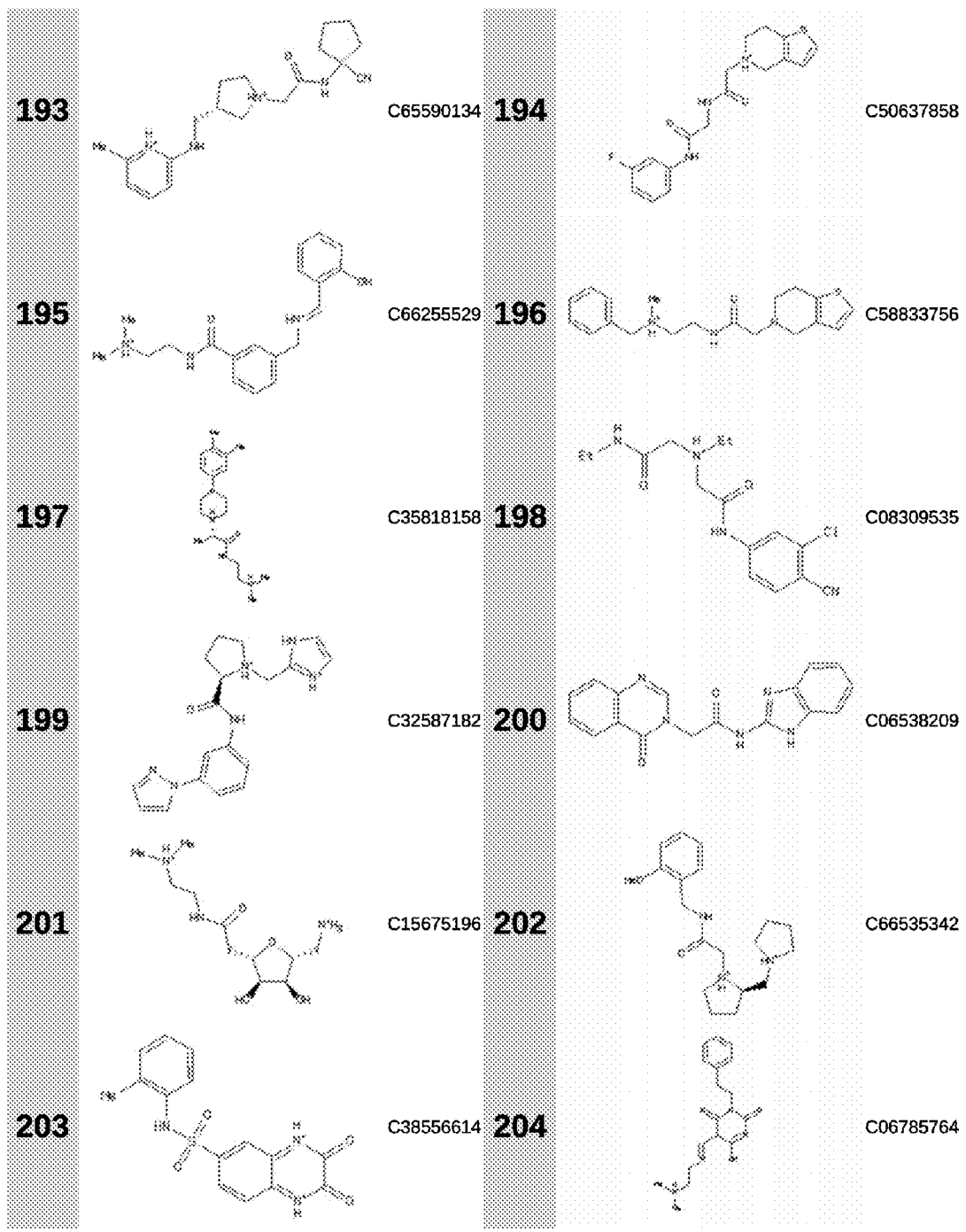
Figure 4:
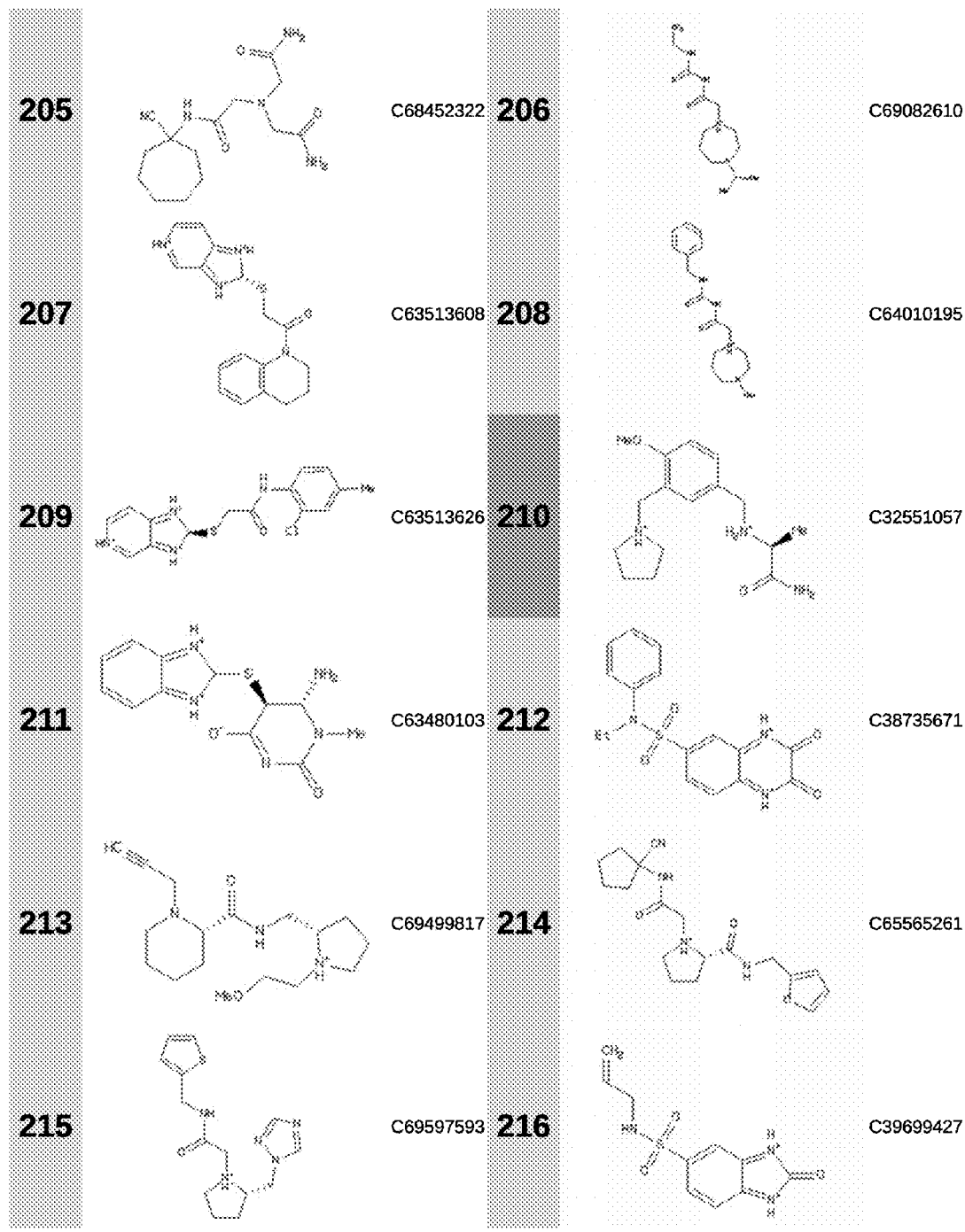
Figure 4:
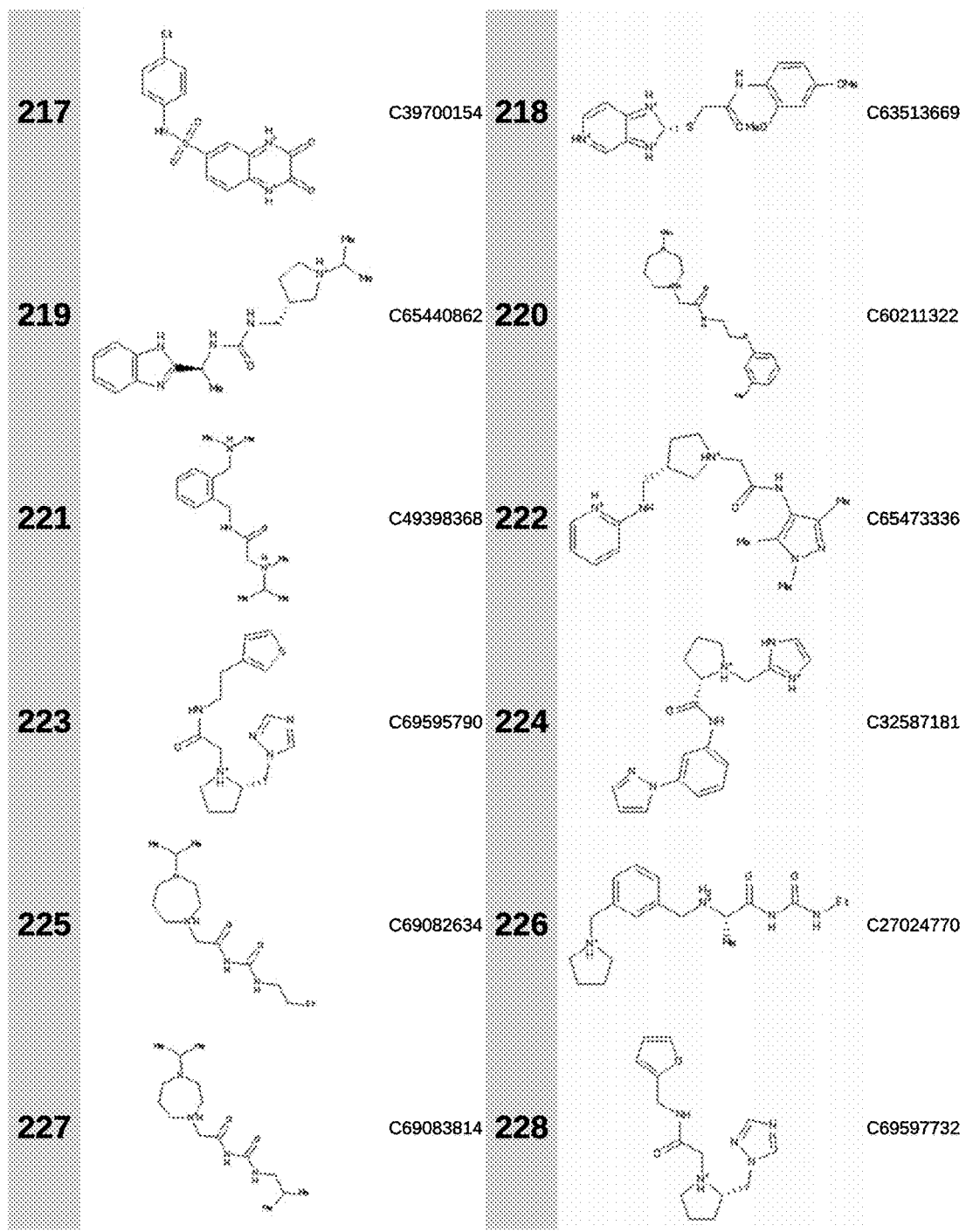
Figure 4:
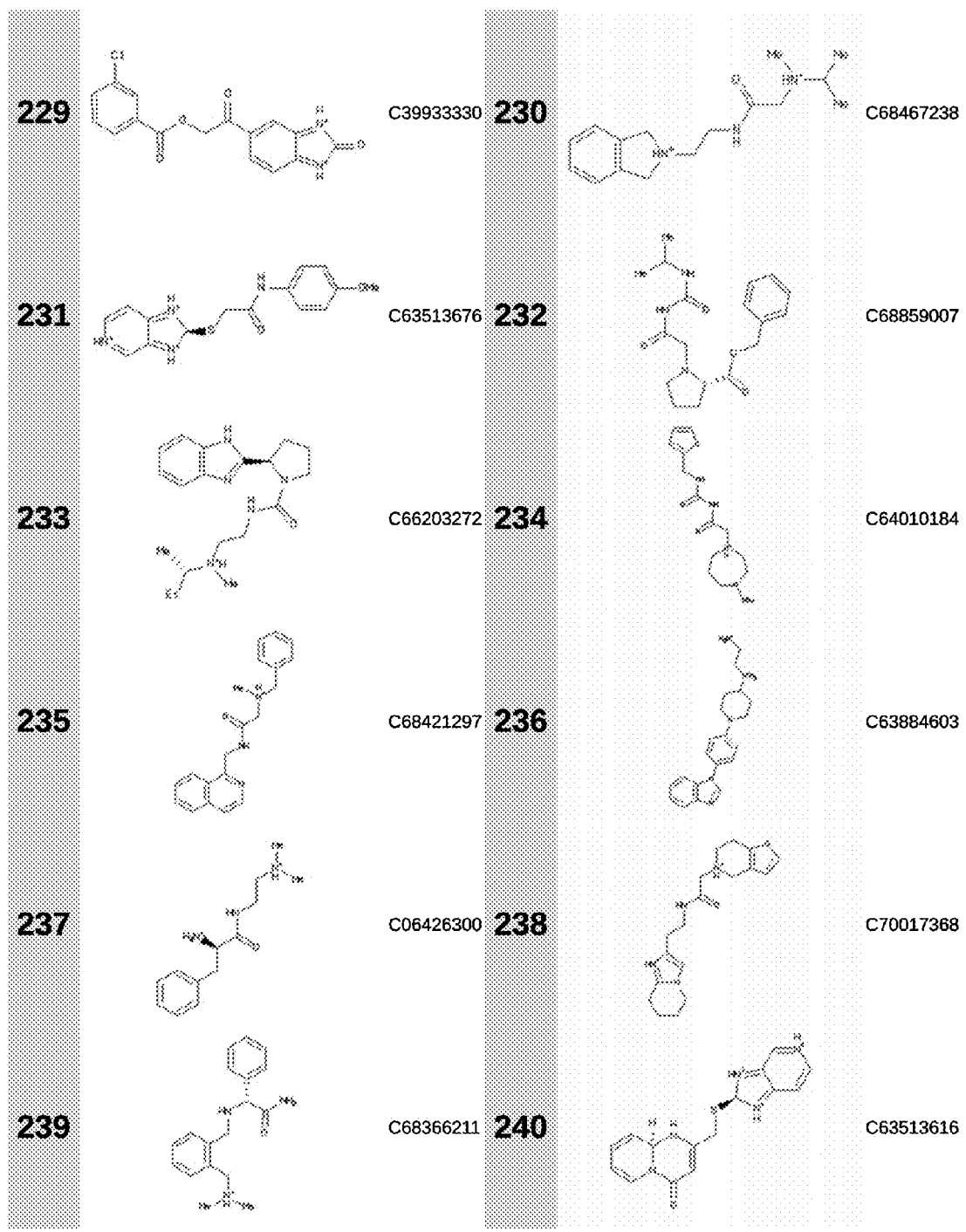
Figure 4:
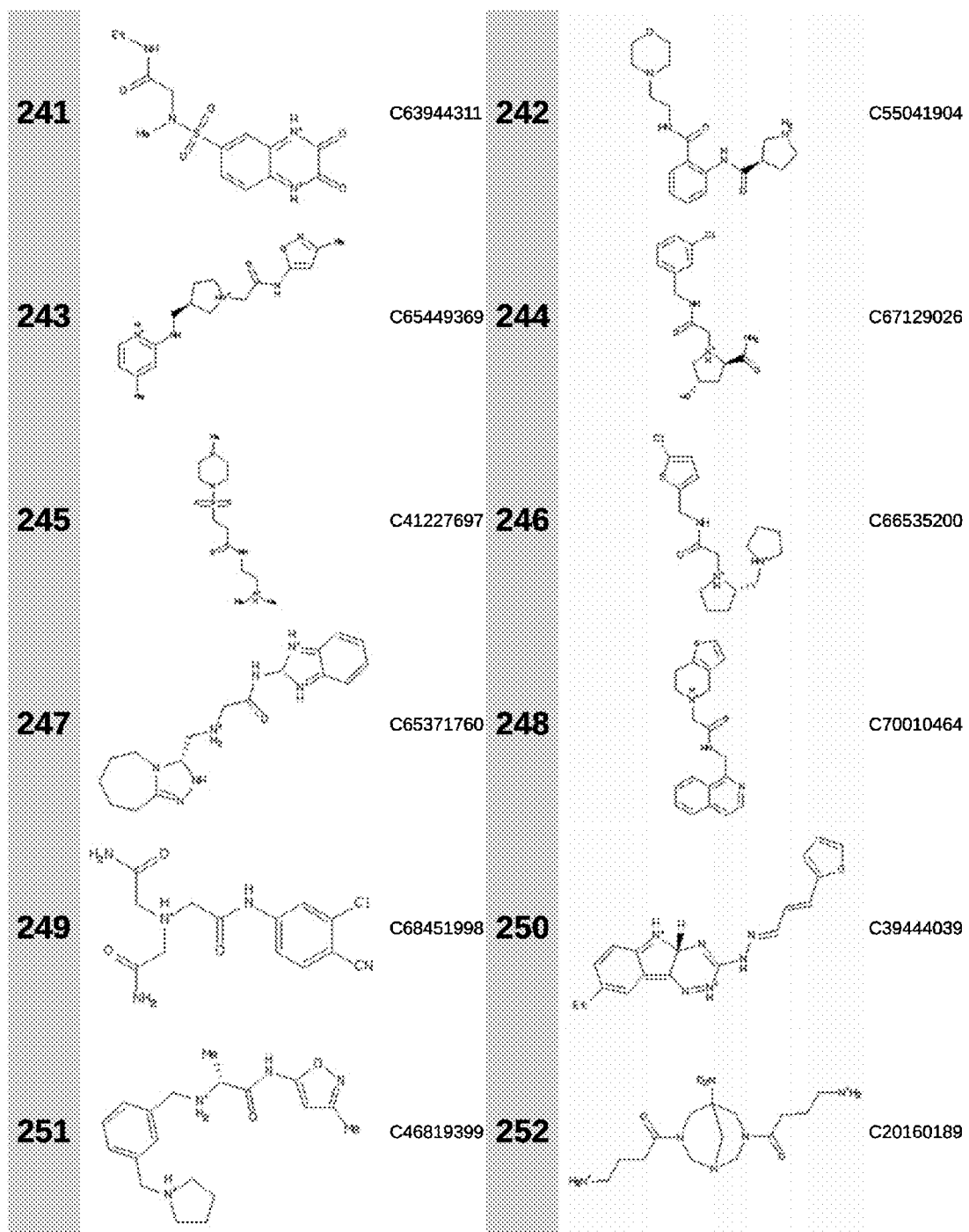
Figure 4:
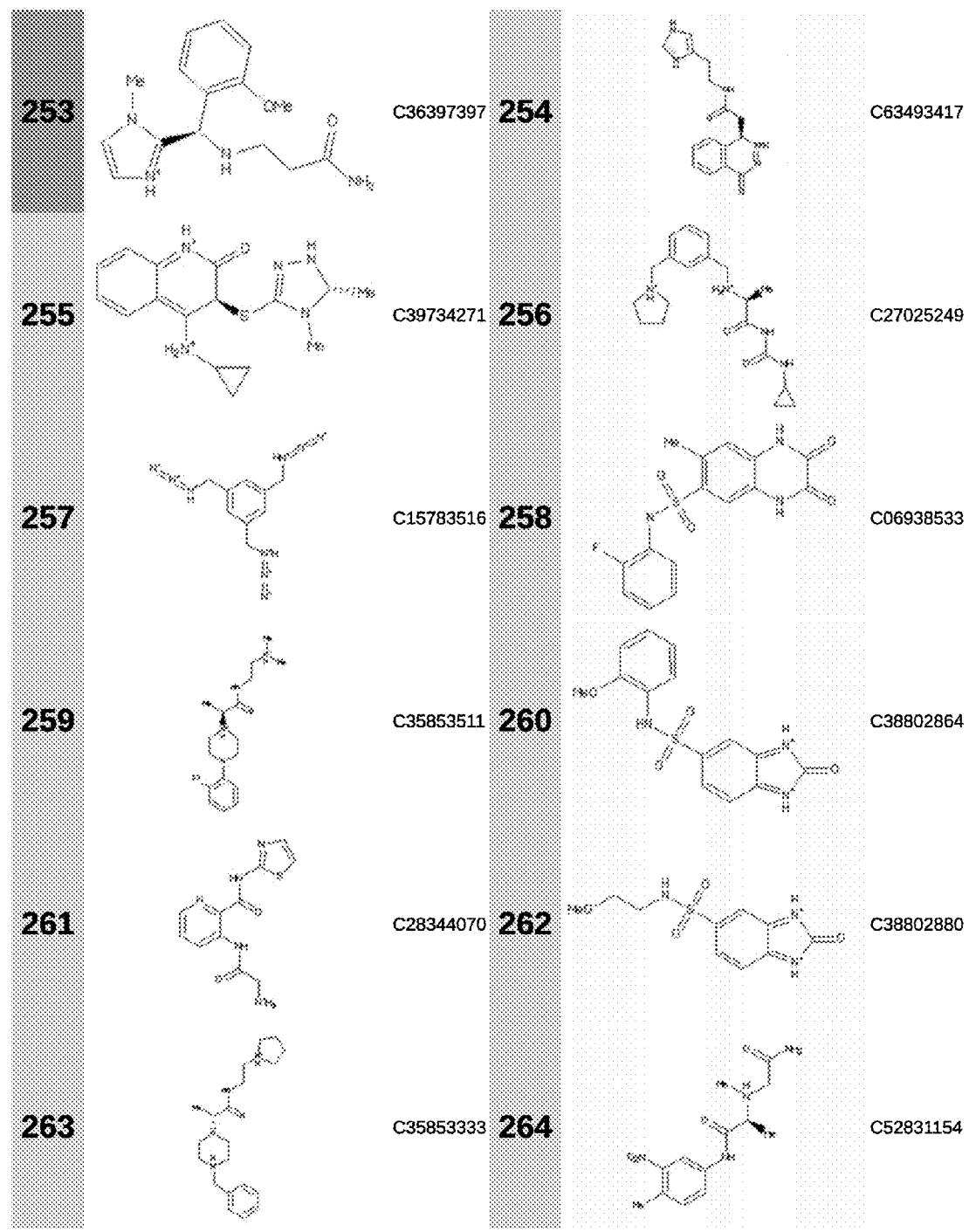
Figure 4:
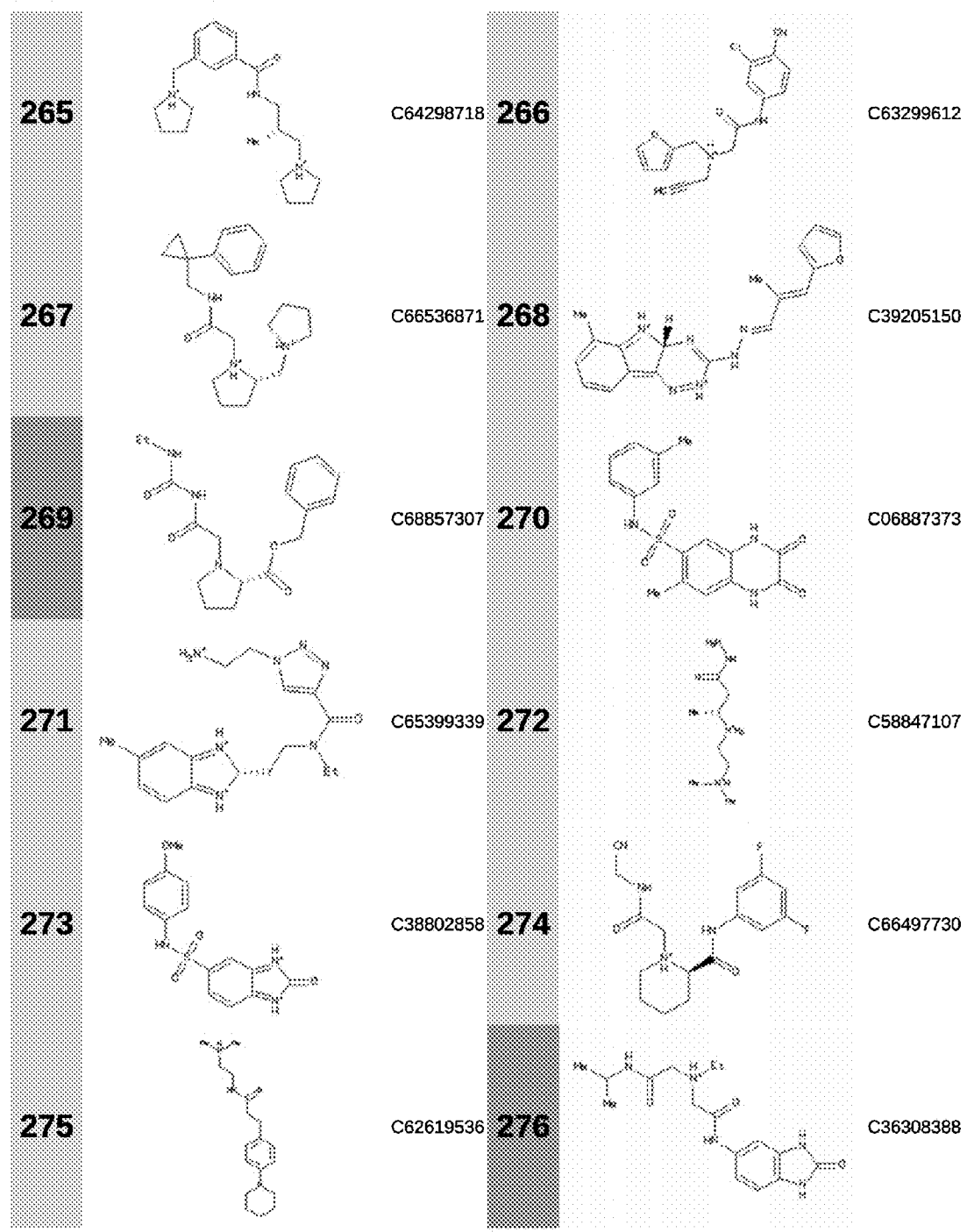
Figure 4:
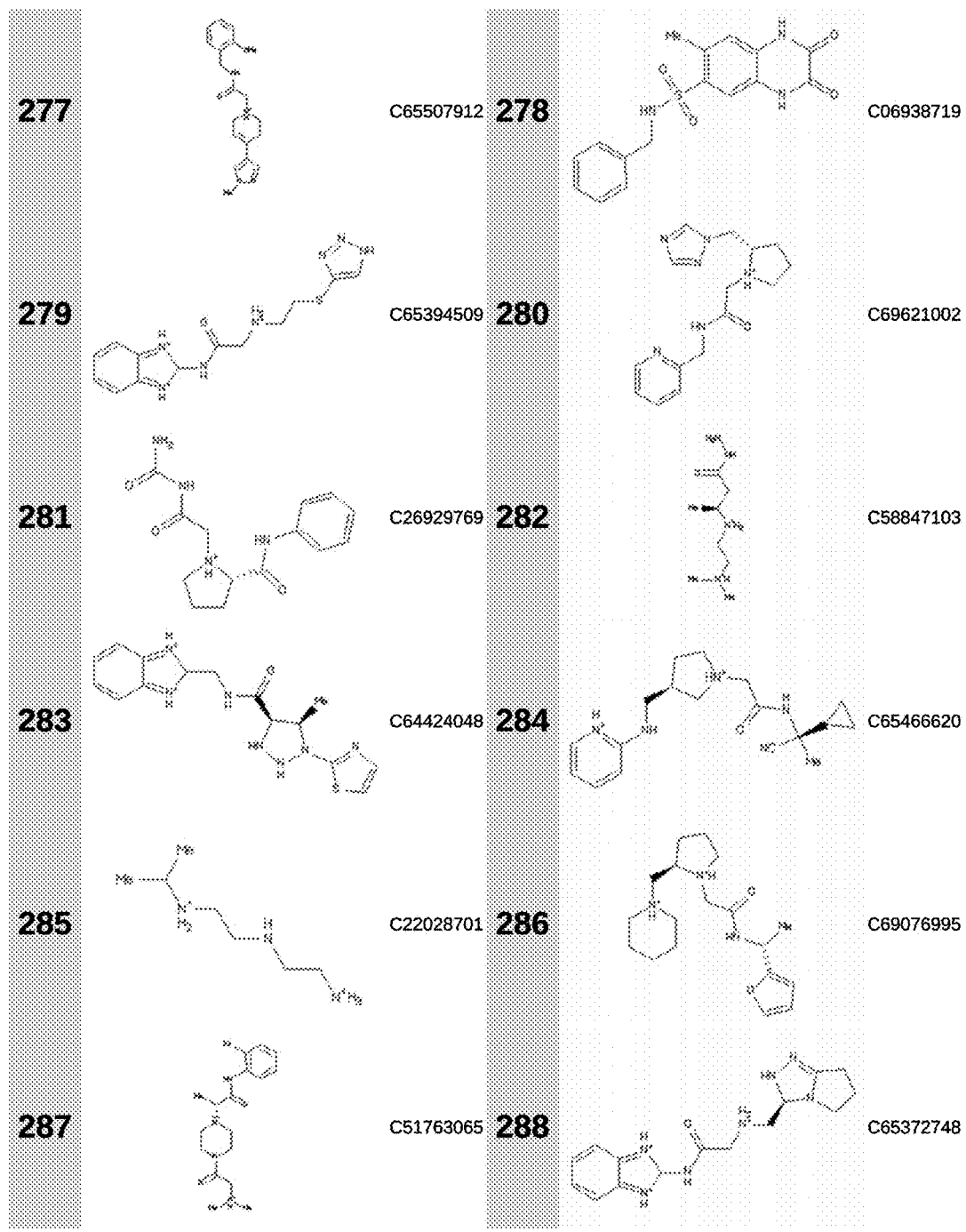
Figure 4:
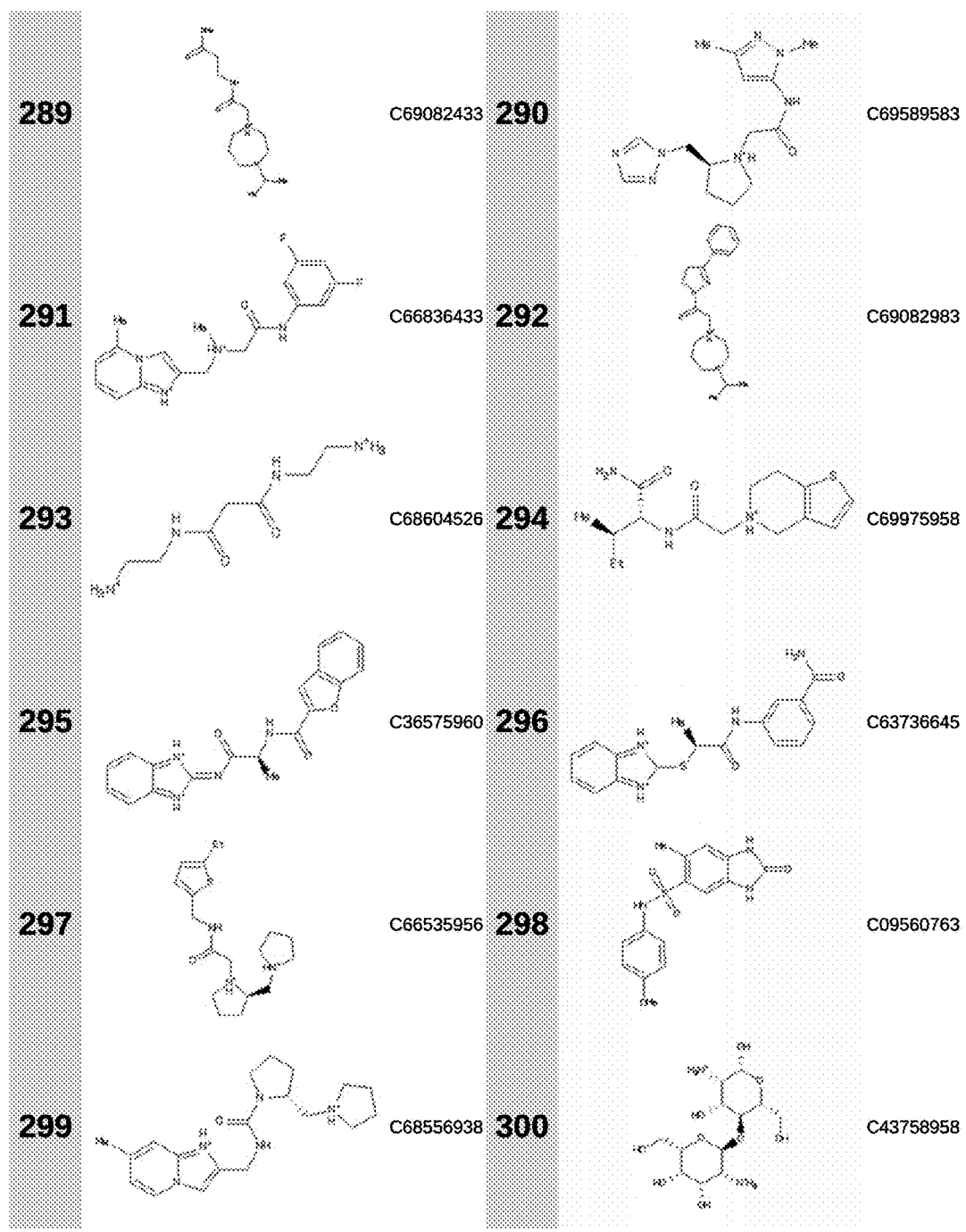
Figure 4:
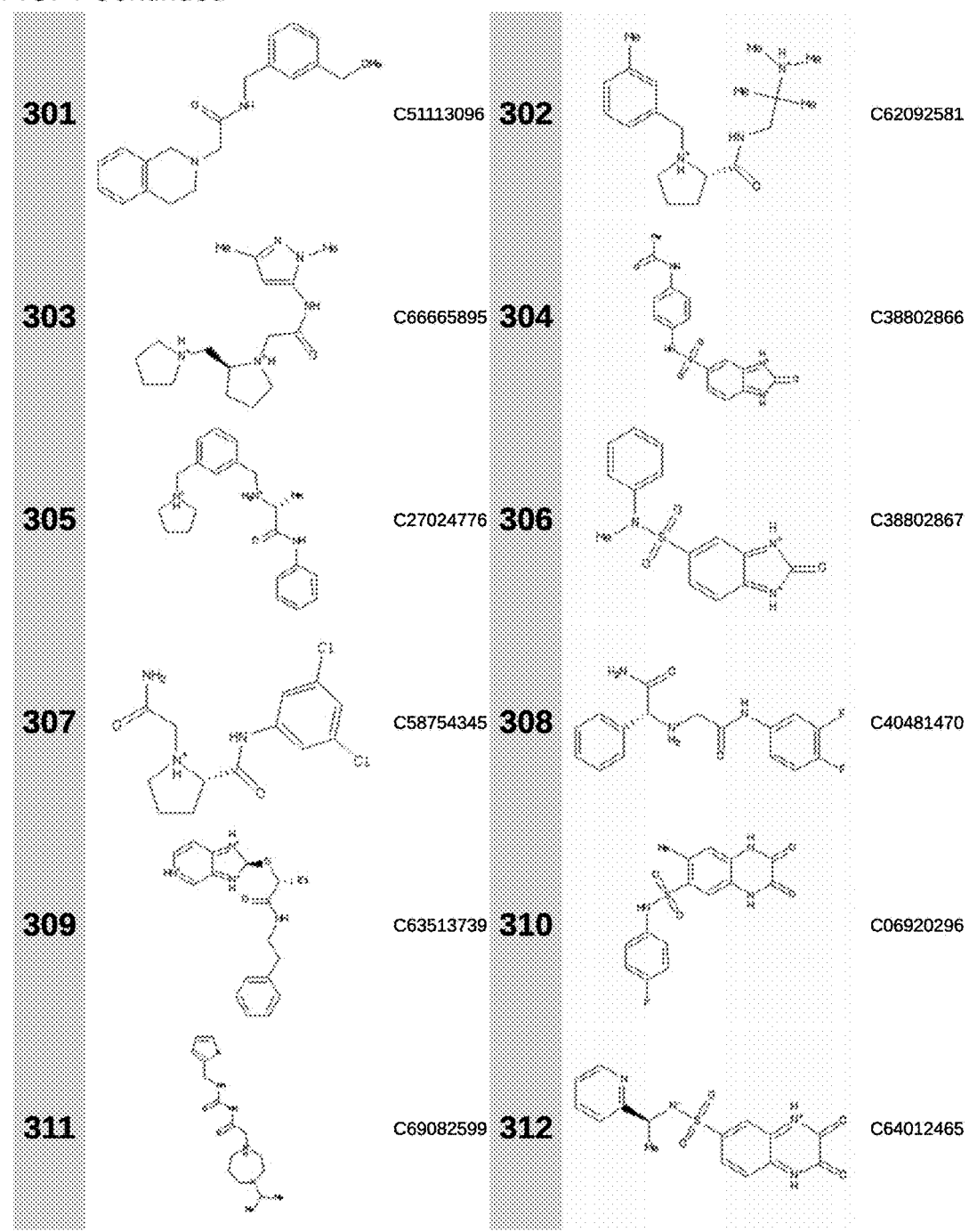
Figure 4:
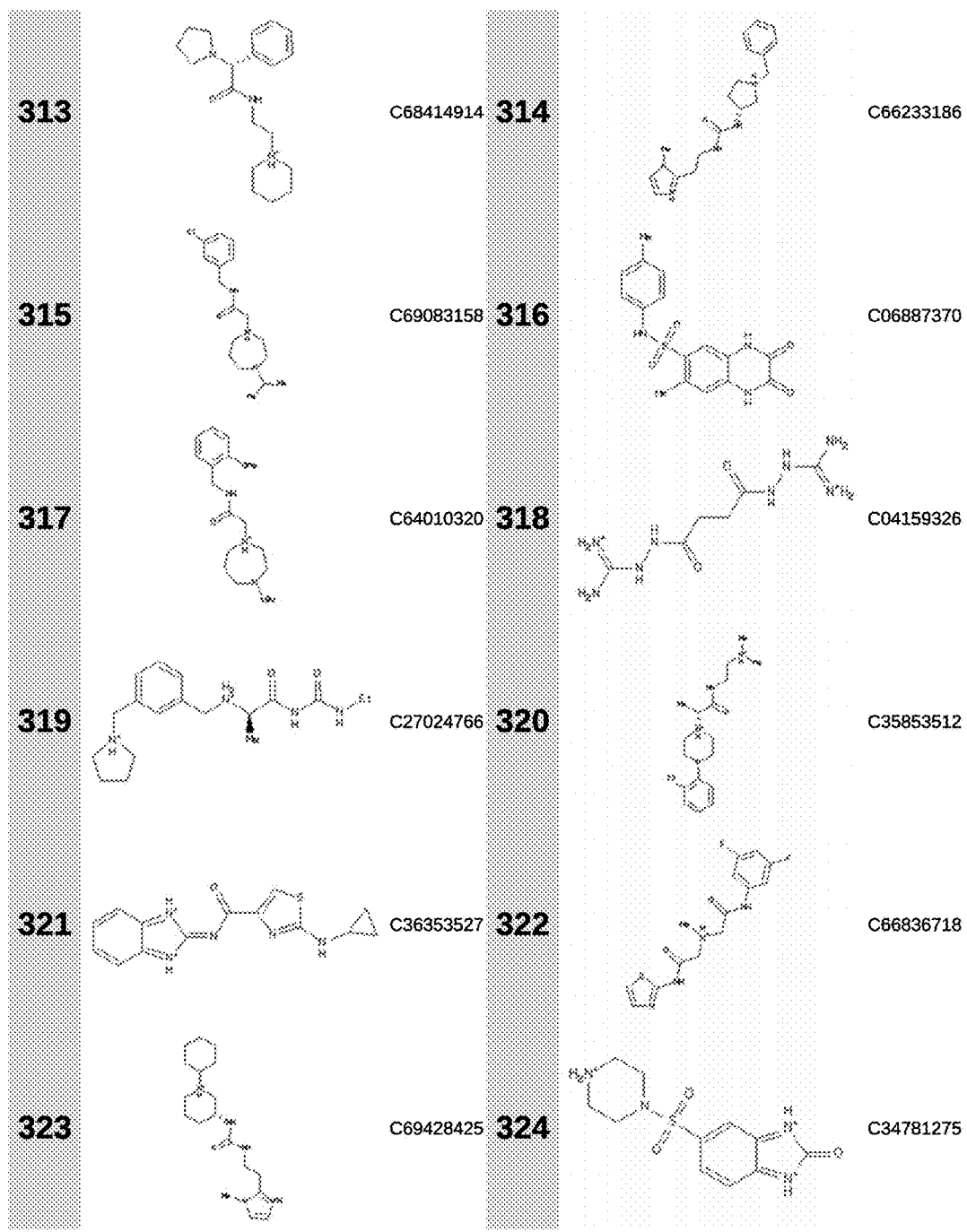
Figure 4:
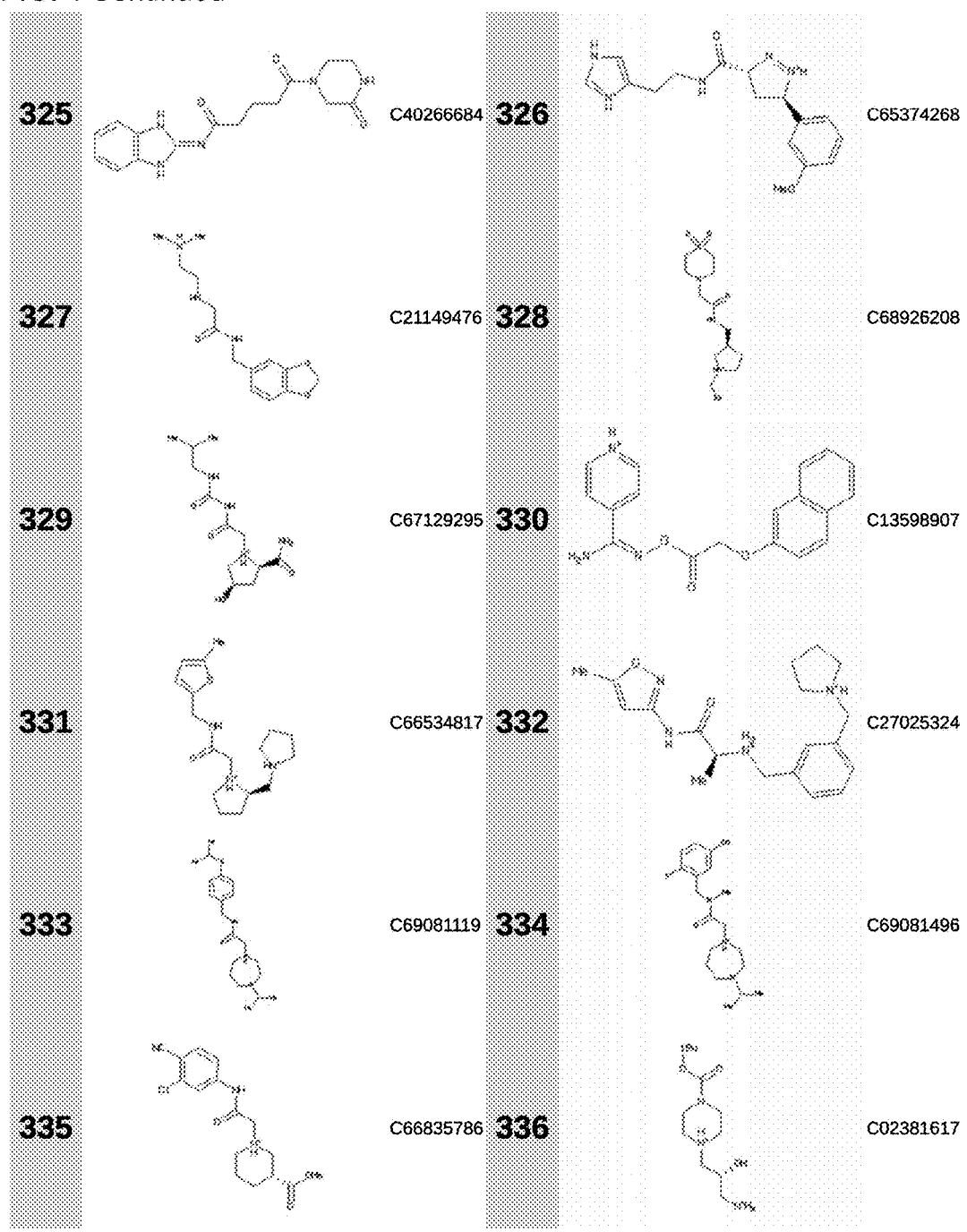
Figure 4:
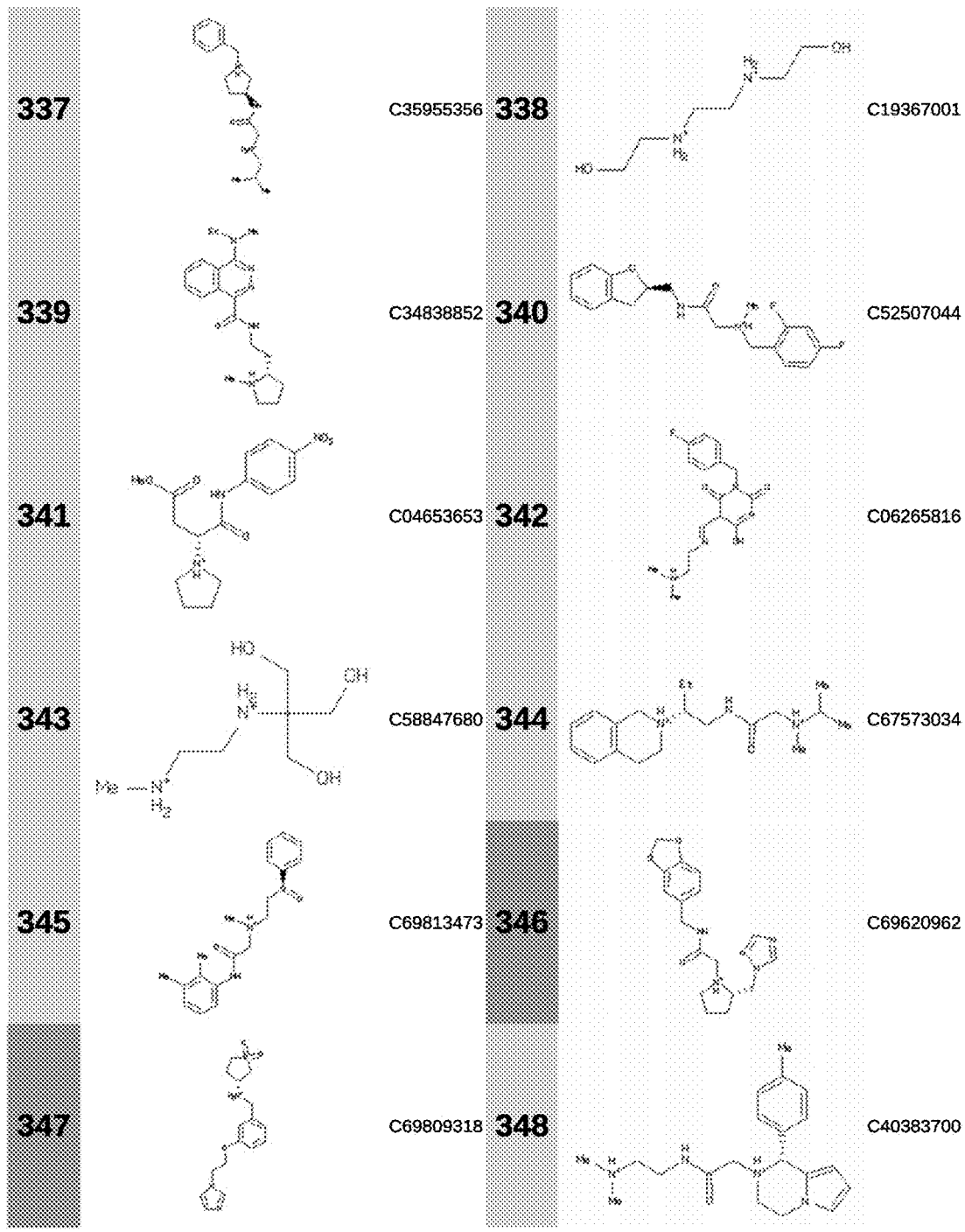
Figure 4:
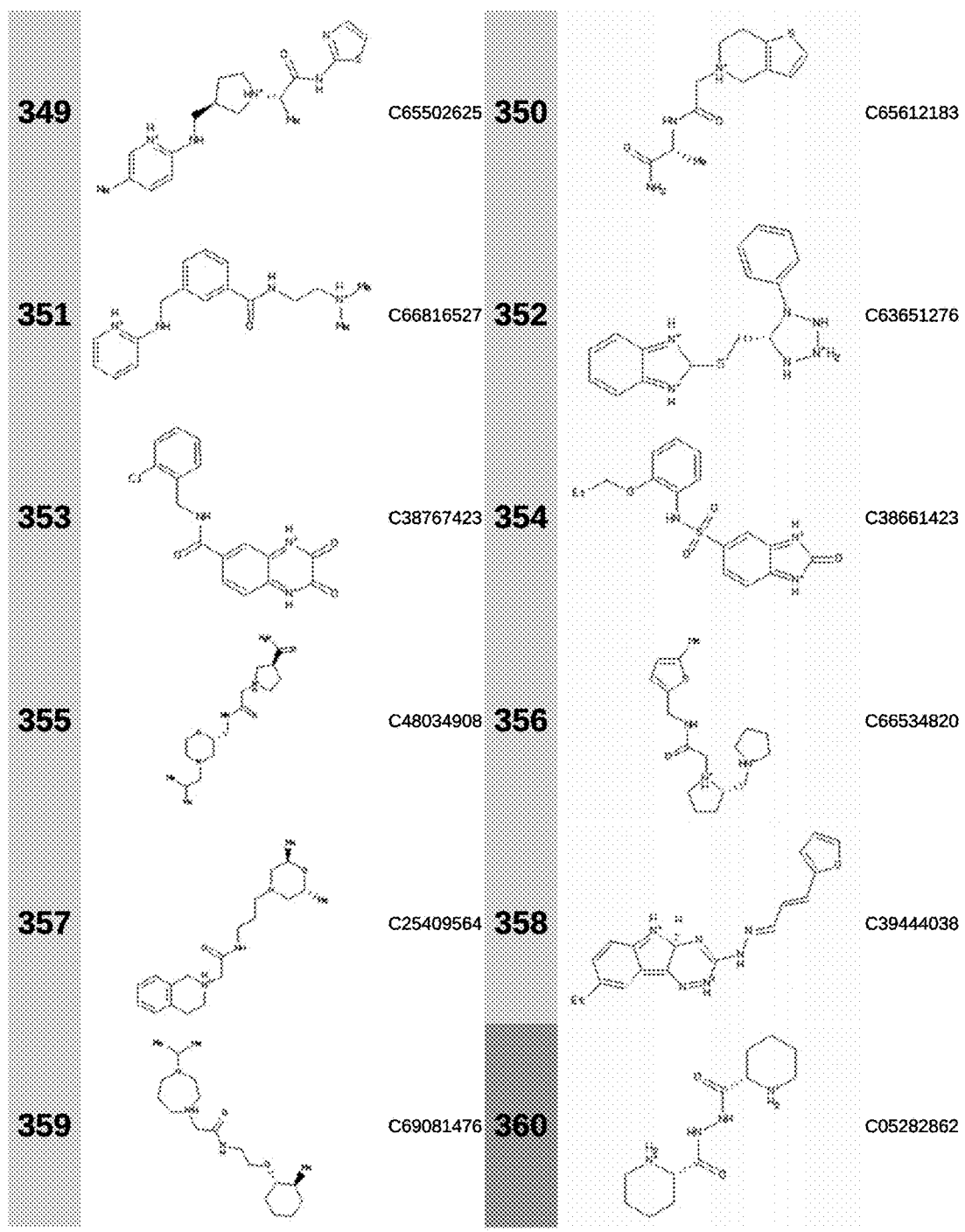
Figure 4:
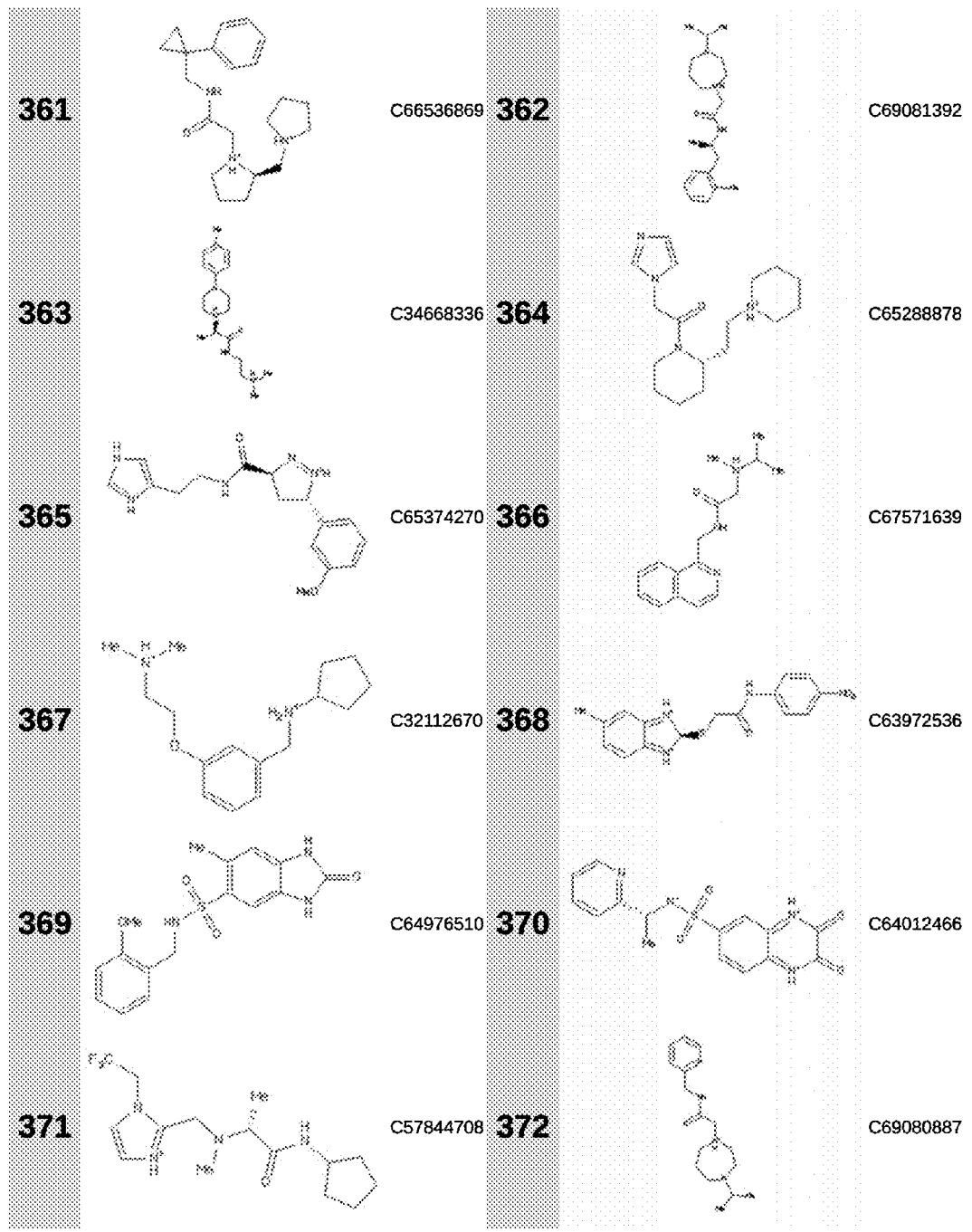
Figure 4:
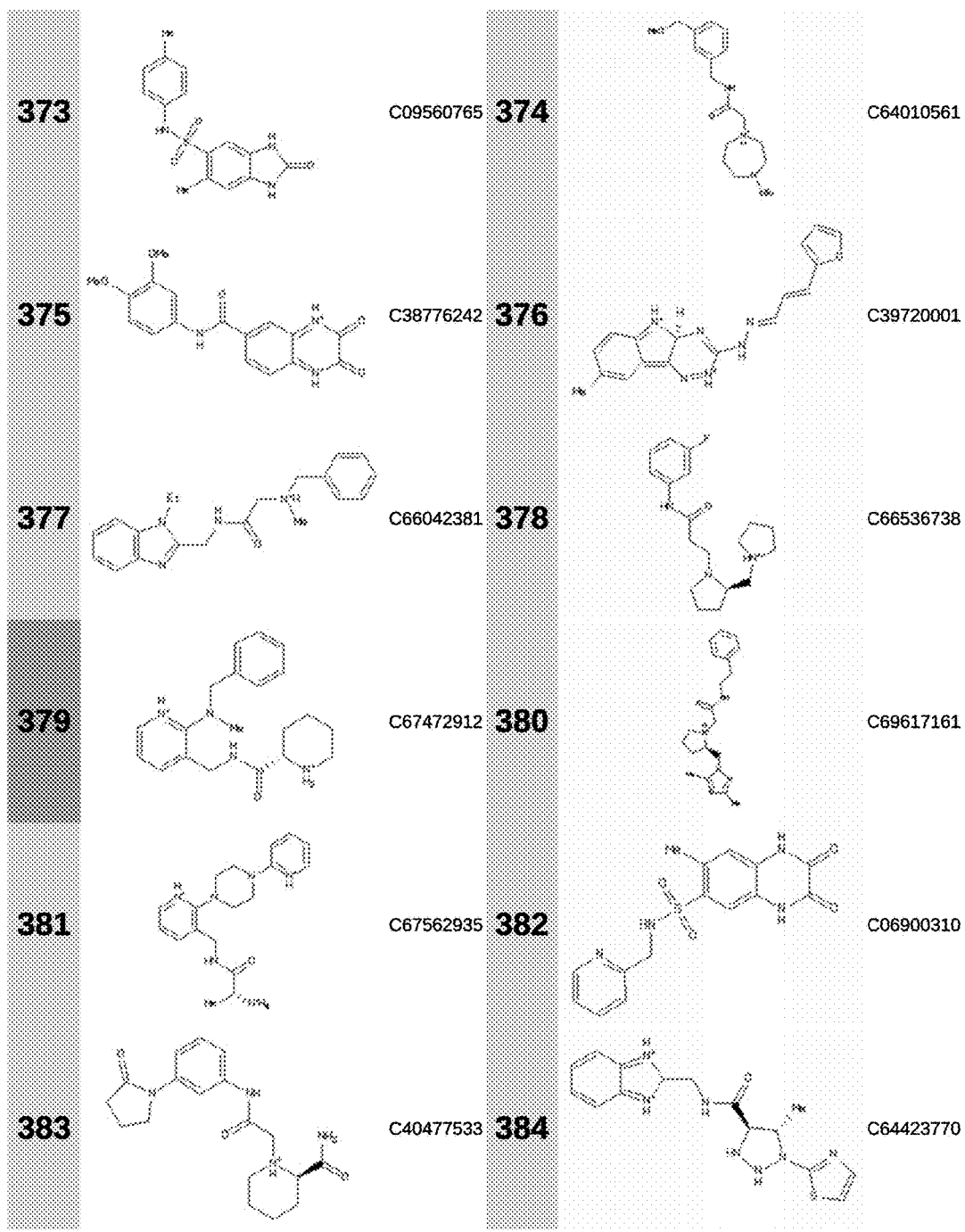
Figure 4:
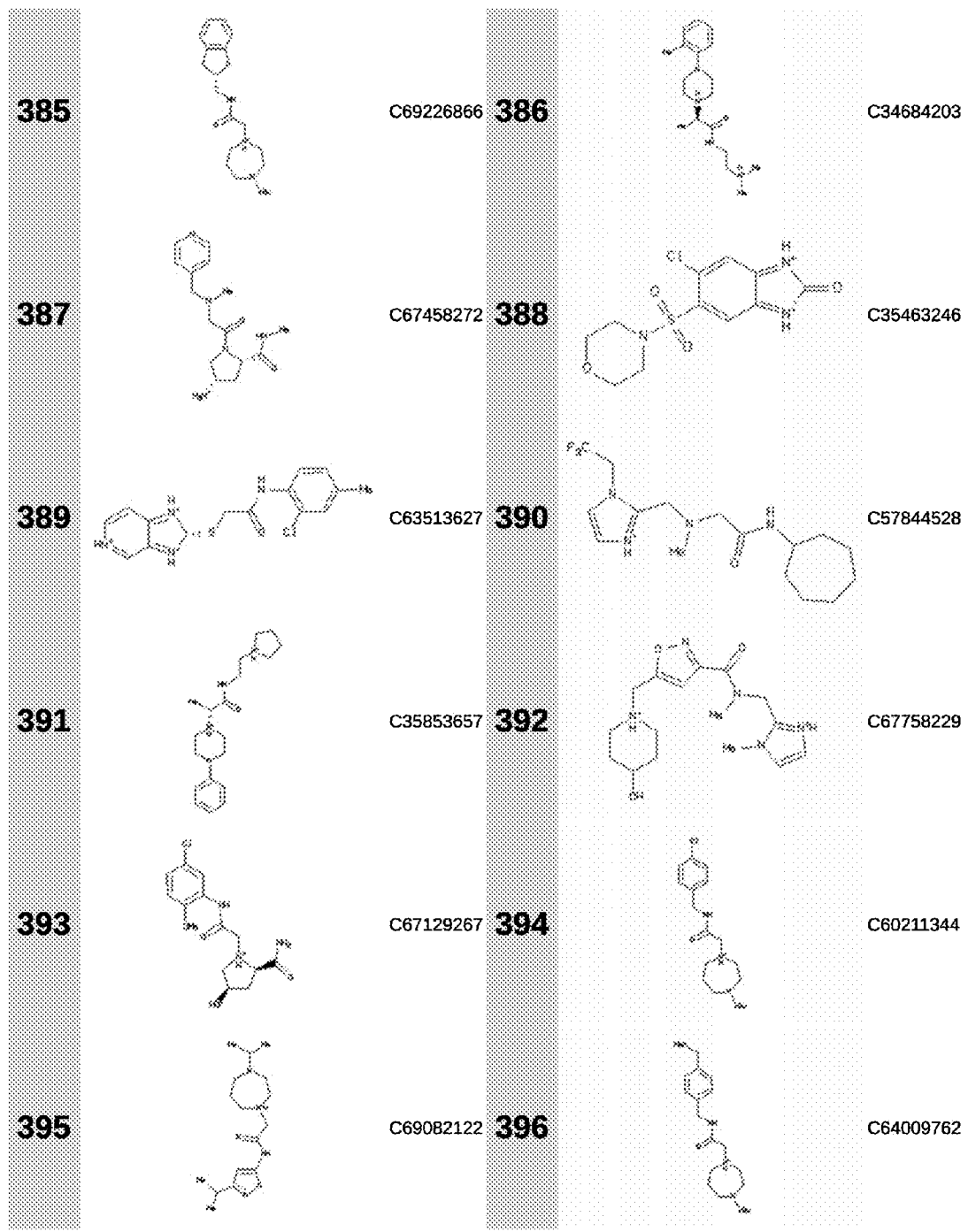
Figure 4:
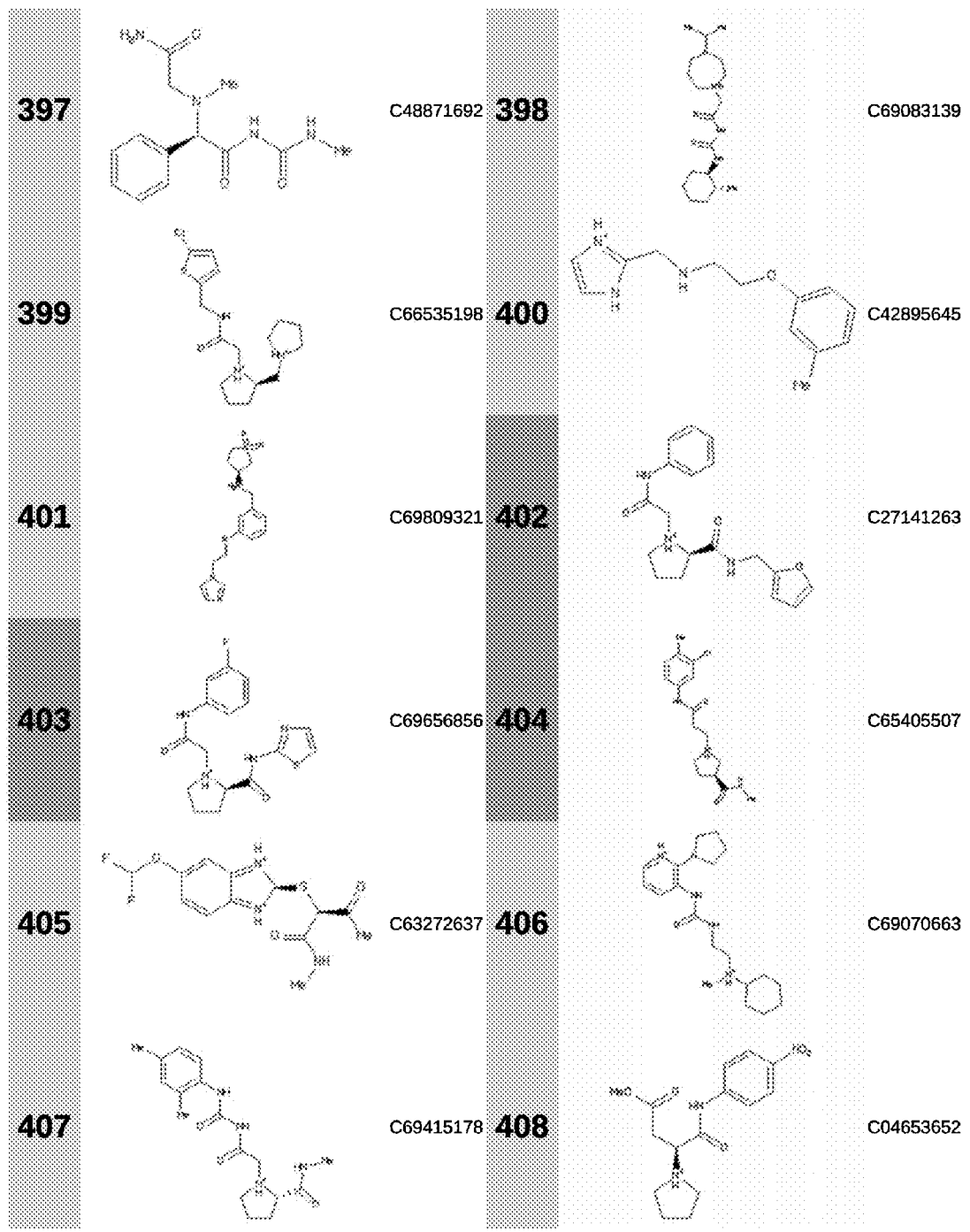
Figure 4:
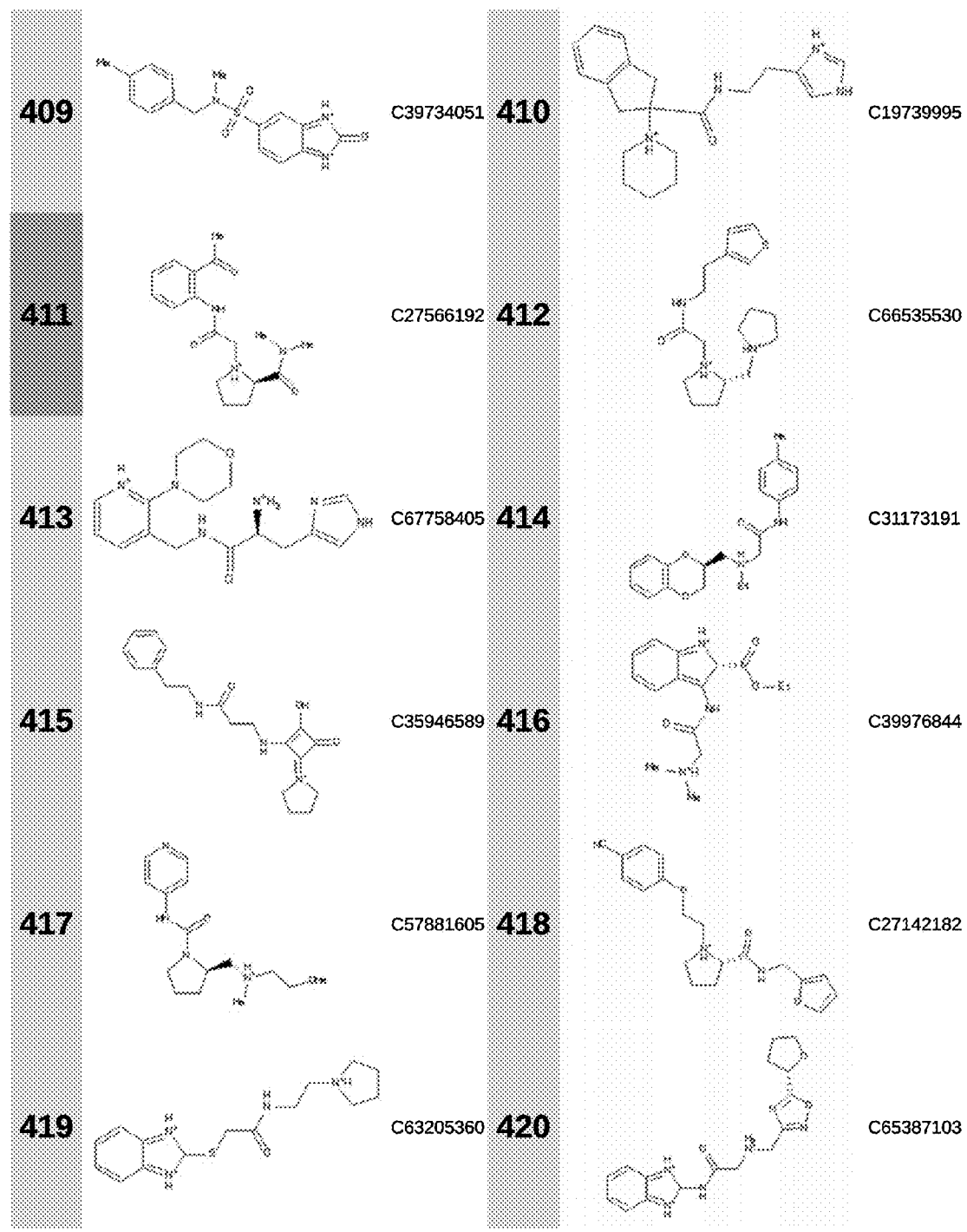
Figure 4:
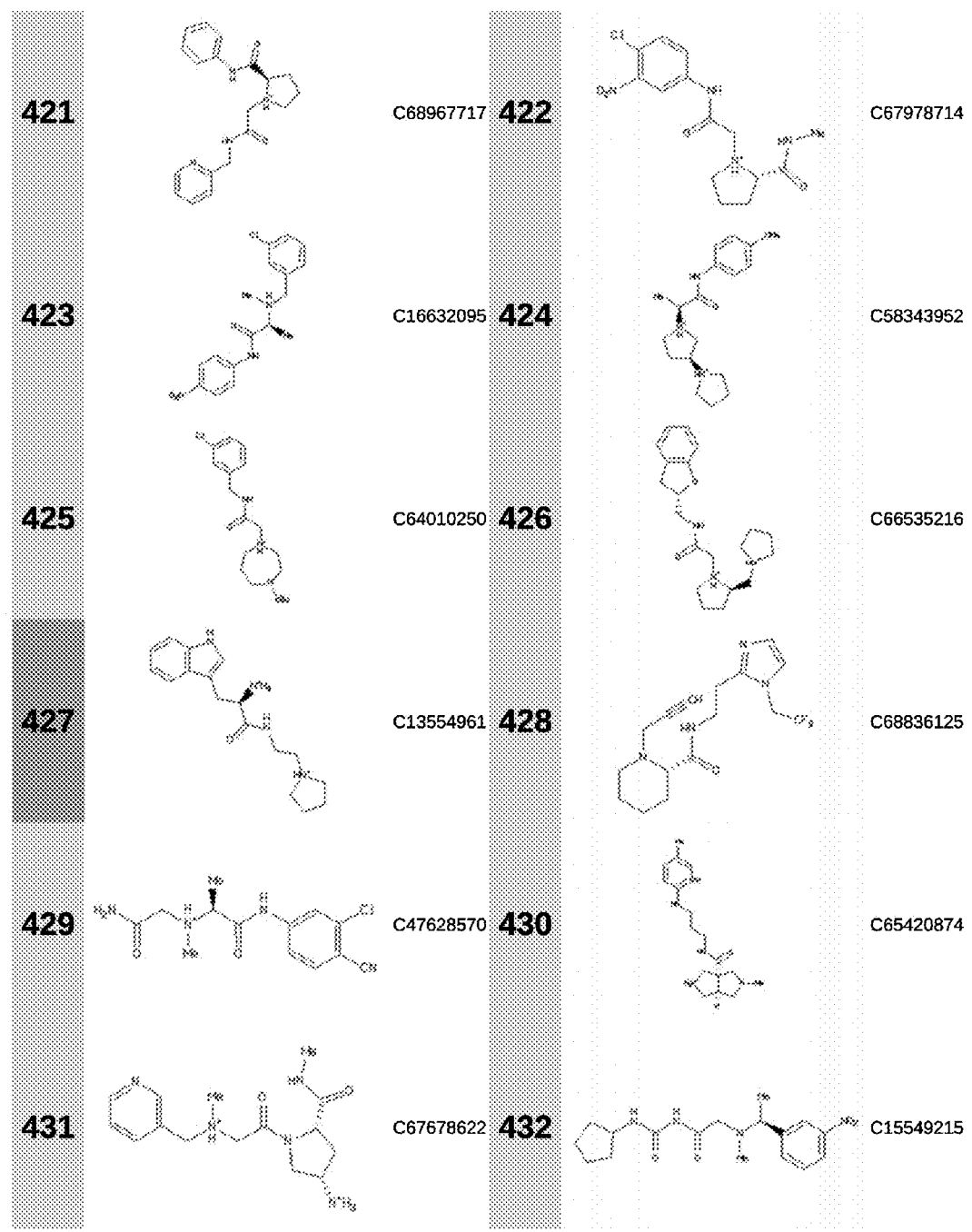
Figure 4:
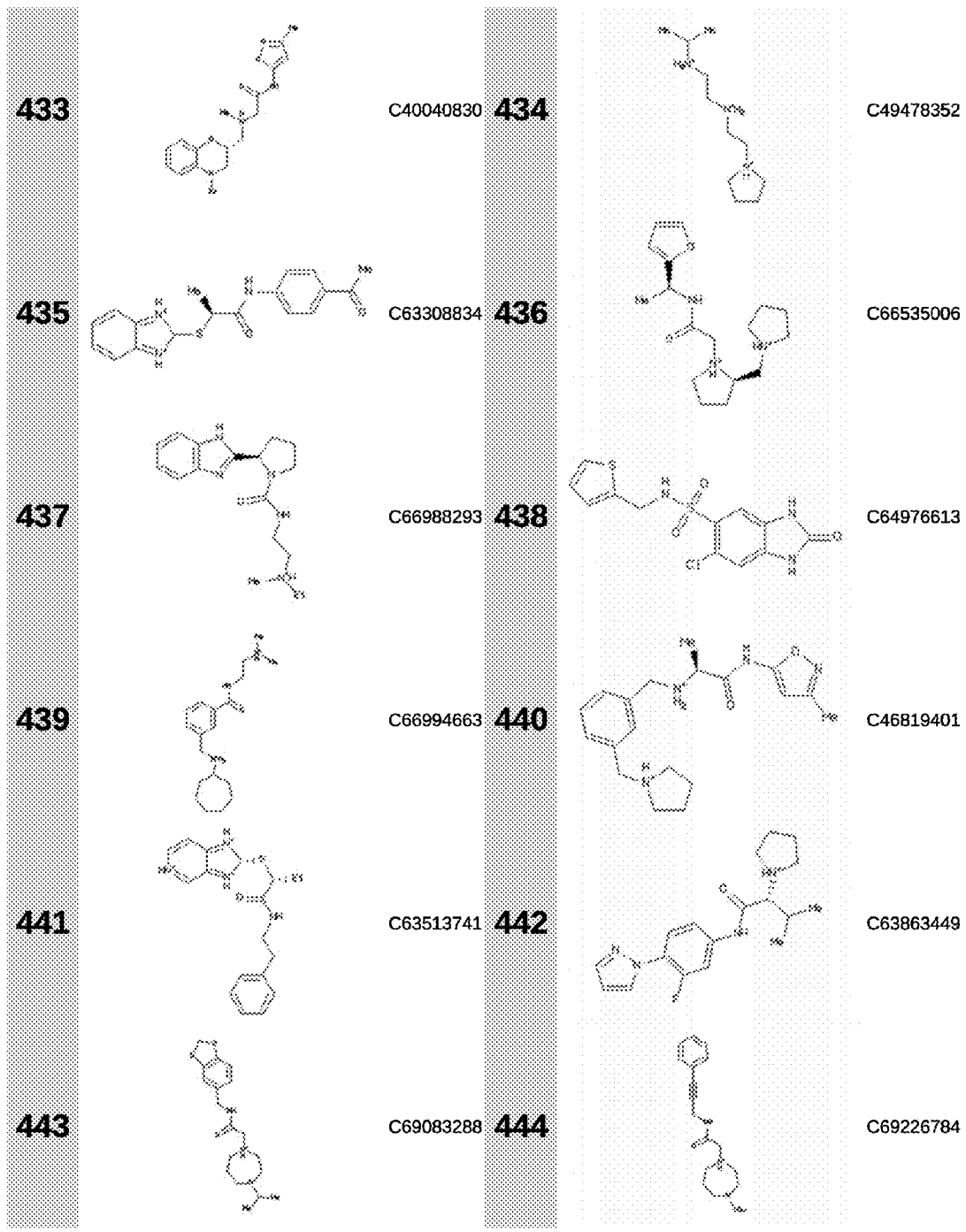
Figure 4:
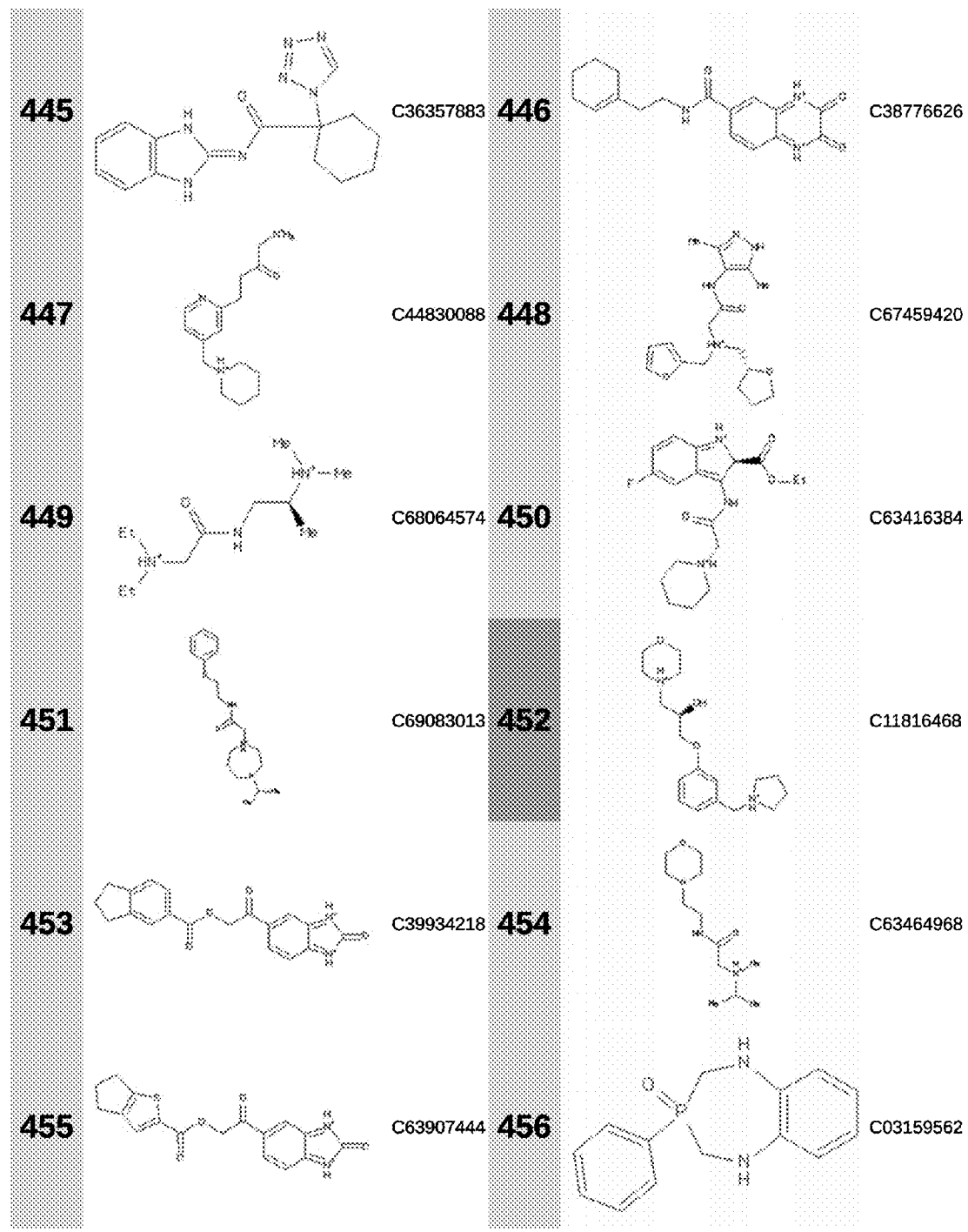
Figure 4:
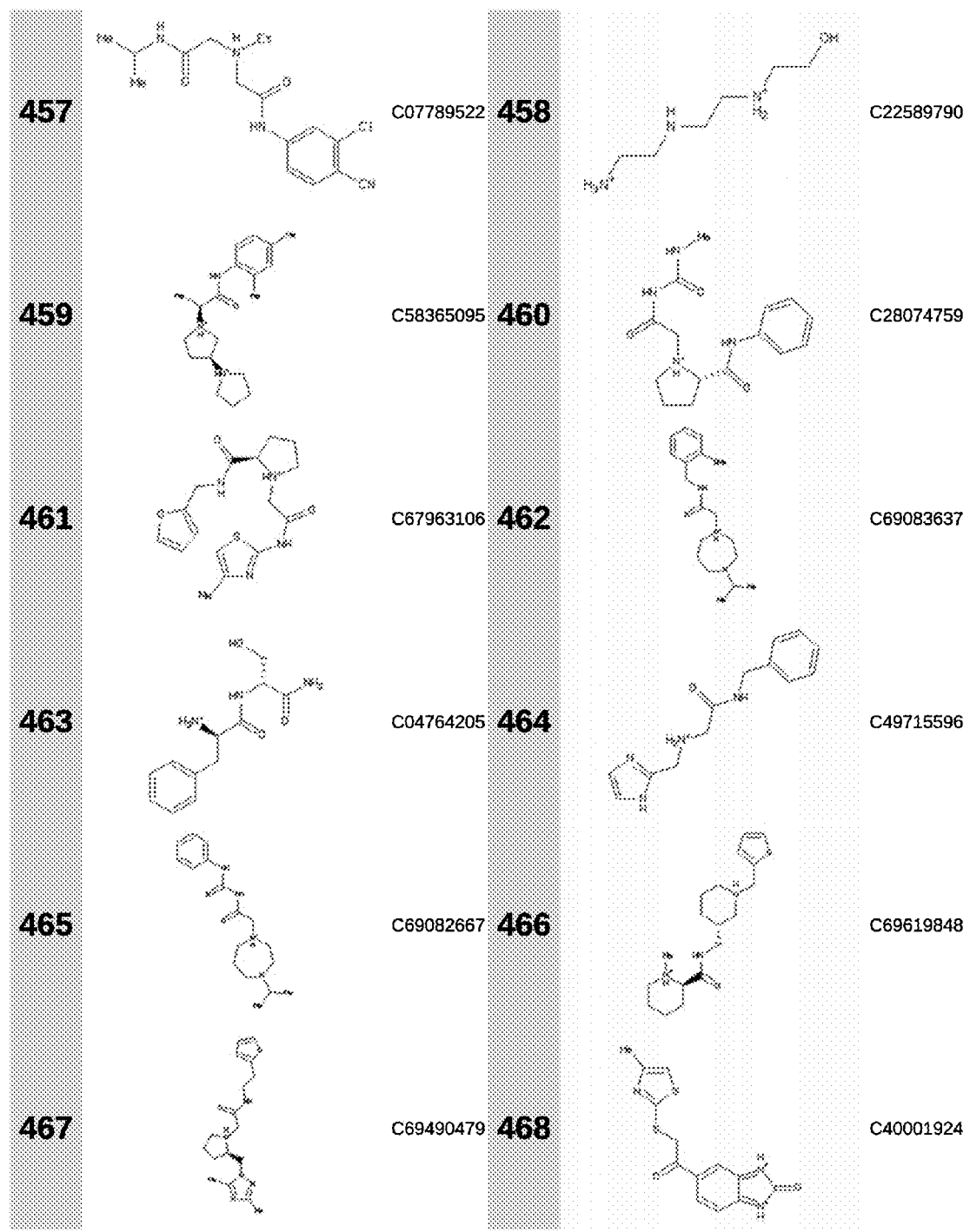
Figure 4:
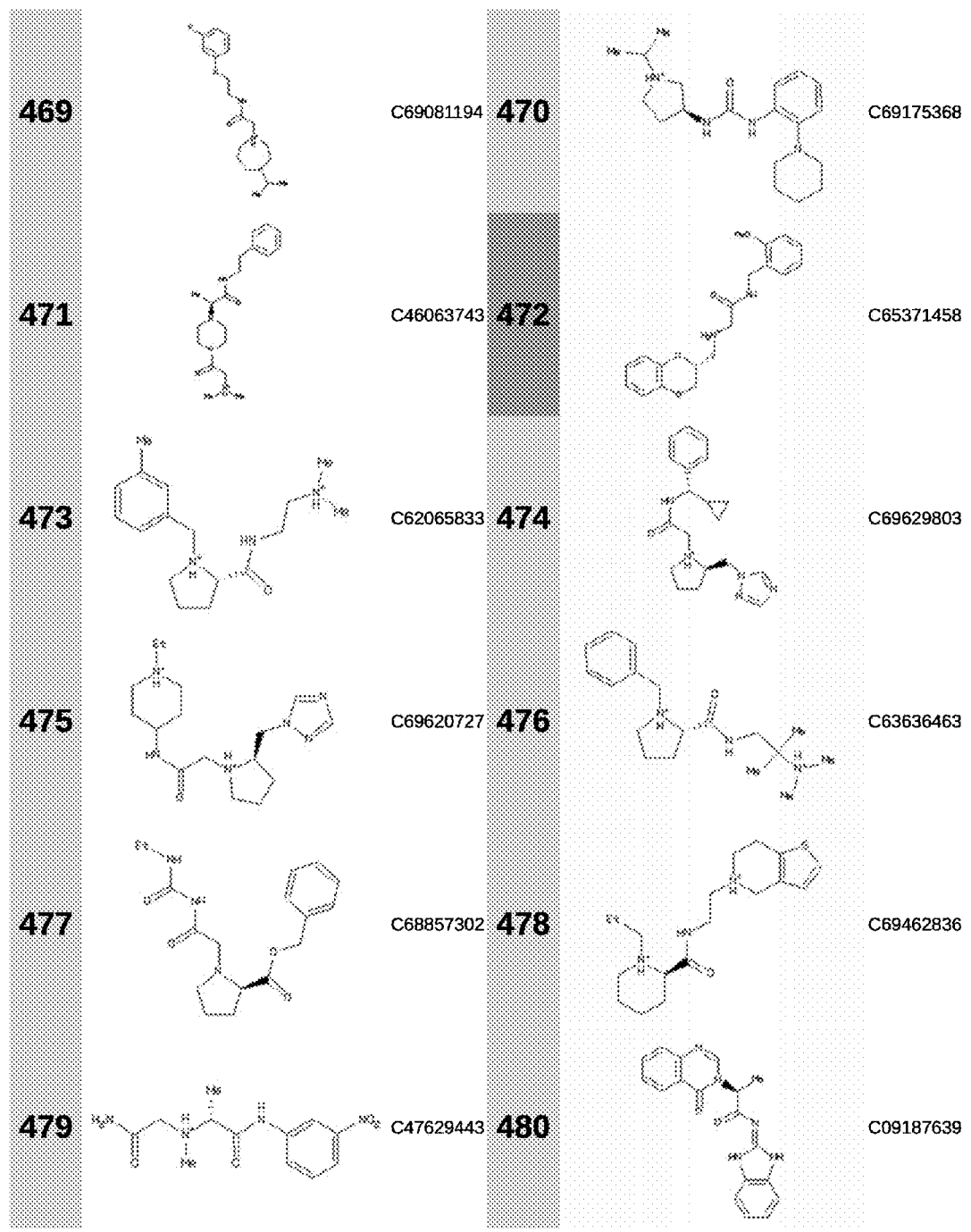
Figure 4:
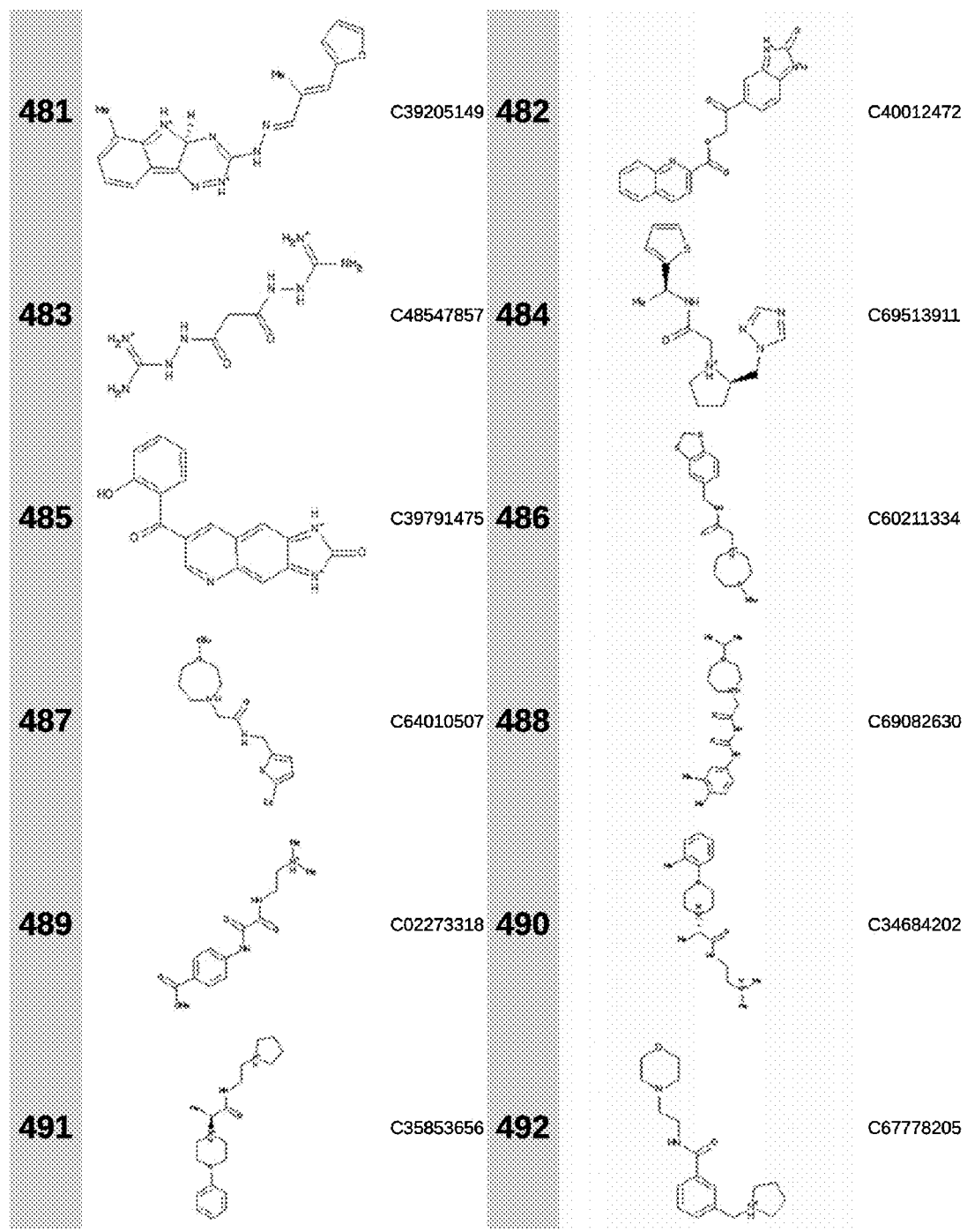
Figure 4:
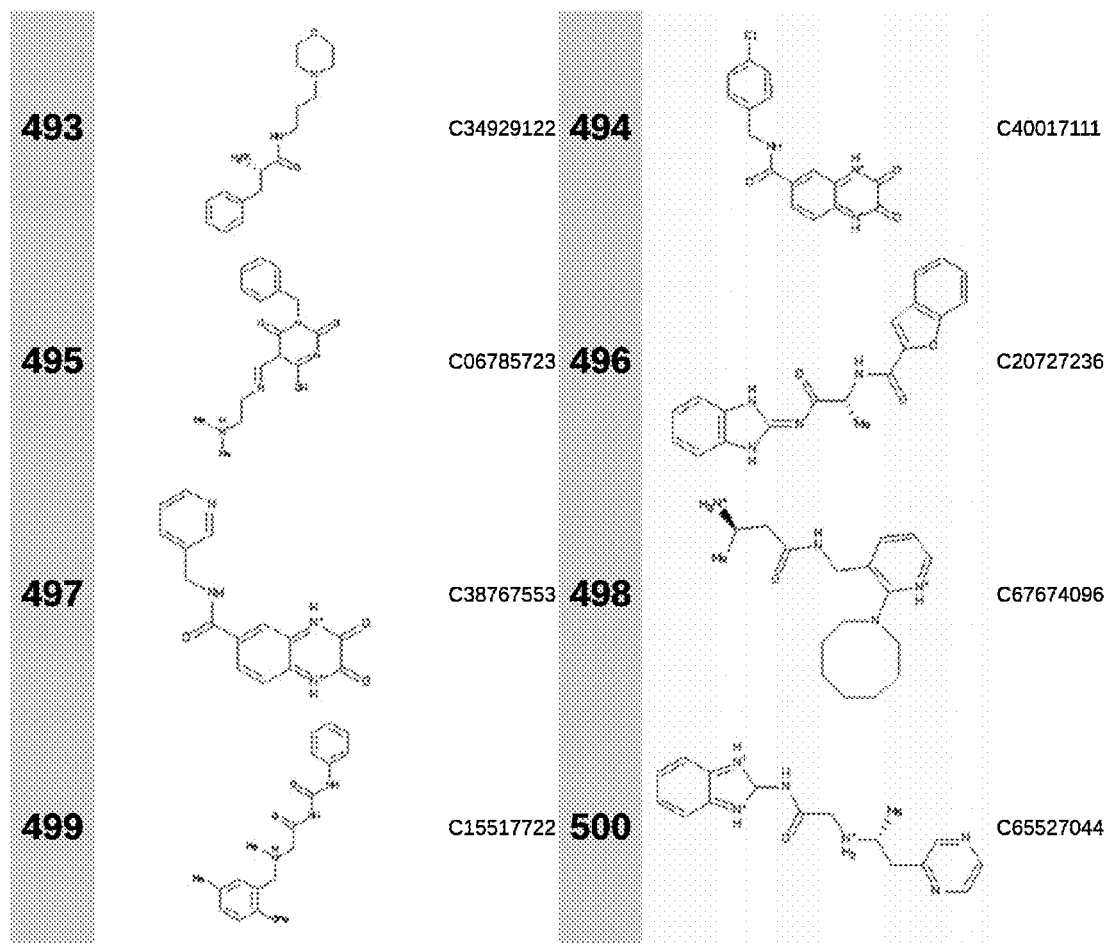

The inventors used the lead-like' subset version of the ZINC database (Irwin et al., 2005) that was accessible online on Feb. 2, 2012, when the molecular docking study was initiated. This subset version contained about 4.5 million commercially available small-molecules selected using the filtering criteria specified on the ZINC database website. Molecular docking at chain A of the recently released inactive KOP receptor structure (PDB ID: 4DJH (Wu et al., 2012)), following removal of all non-protein atoms, was performed with DOCK3.6 (Lorber et al., 1998; Lorber et al., 2005; Kuntz et al., 1982; Mysinger et al., 2010). The atom positions of the JDTic crystallographic ligand within the KOP receptor binding pocket were replaced by forty-five spheres that had been labeled for chemical matching based on the local protein environment. Default parameters, i.e., a bin size of 0.2 Å, a bin size overlap of 0.1 Å, and a distance tolerance of 1.2 Å for both the binding site matching spheres and each docked small-molecule from the 'lead-like' subset, were used for ligand conformational sampling. Partial charges from the united atom AMBER force field (Wiener et al., 1984) were used for all receptor residues with the exception of Asp138 in transmembrane helix 3 (McCurdy et al., 2010; Carlsson et al., 2010). The dipole moment of this residue was increased by 0.4 per polar atom to favor identification of small molecules that would form ionic interactions with this residue (Carlsson et al., 2010). The KOP receptor was kept rigid while each small molecule was docked into the binding pocket in an average of 3,073 orientations relative to the receptor, and an average of 2,132 conformations for each orientation. A score corresponding to the sum of the receptor-ligand electrostatic and van der Waals interaction energies, corrected for ligand desolvation, was assigned to each docked molecule and configuration within the KOP receptor binding pocket. The specific energy estimates were obtained as recently described for an analogous study (Negri et al., 2012). The best scoring conformation of each docked molecule was further subjected to 100 steps of energy minimization with the protein residues kept rigid. Twenty-two compounds, termed here MCKK-1-22, and listed in Table 1 below, were selected from visual inspection of the 500 top-scoring docked compounds (FIG. 4) based on criteria discussed in Example 2.

TABLE 1

List of the 22 tested compounds and their corresponding chemical structure, DOCK scoring rank from the virtual screening experiment, and extended connectivity fingerprint maximum distance 4 (ECFP4)-based Tanimoto similarity coefficient (Tc) to the most similar known opioid ligand in the ChEMBL database.

| Compound (Rank) | Structure | ECFP4 based $T_c$ | Most similar known opioid ligand |
|---|---|---|---|
| MCKK-1 (1) | 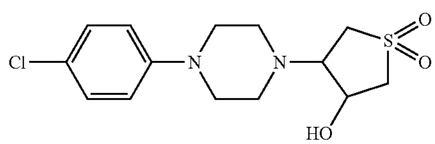 [SMILES: O=S1(=O)CC(O)C(N2CCN(c3ccc(Cl)cc3)CC2)C1] | 0.26 | |
| MCKK-2 (80) | 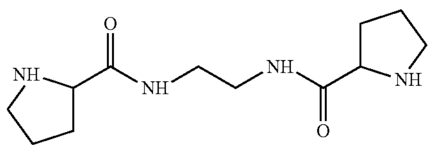 [SMILES: O=C(NCCNC(=O)C1CCCN1)C1CCCN1] | 0.24 | |
| MCKK-3 (87) | 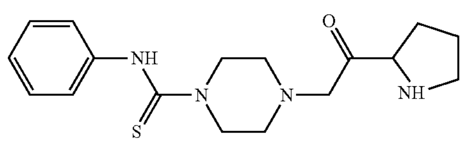 [SMILES: O=C(CN1CCN(C(=S)Nc2ccccc2)CC1)C1CCCN1] | 0.25 | |
| MCKK-4 (97) | 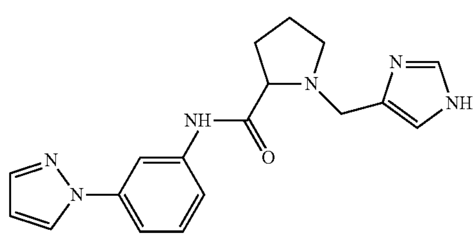 [SMILES: O=C(Nc1cccc(-n2cccn2)c1)C1CCCN1Cc1c[nH]cn1] | 0.20 | |
| MCKK-5 (111) | 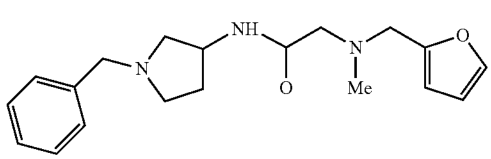 [SMILES: CN(Cc1ccco1)CC(O)NC1CCN(Cc2ccccc2)C1] | 0.27 | |
| MCKK-6 (127) | 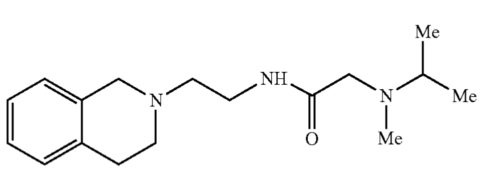 [SMILES: CC(C)N(C)CC(=O)NCCN1CCc2ccccc2C1] | 0.38 | |

TABLE 1-continued

List of the 22 tested compounds and their corresponding chemical structure, DOCK scoring rank from the virtual screening experiment, and extended connectivity fingerprint maximum distance 4 (ECFP4)-based Tanimoto similarity coefficient (Tc) to the most similar known opioid ligand in the ChEMBL database.

| Compound (Rank) | Structure | ECFP4 based $T_c$ | Most similar known opioid ligand |
|---|---|---|---|
| MCKK-7 (137) | 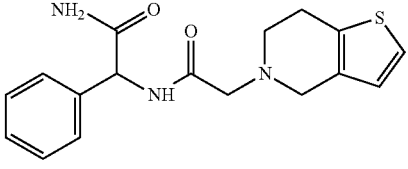 [SMILES: NC(=O)C(NC(=O)CN1CCc2sccc2C1)c1ccccc1] | 0.23 | 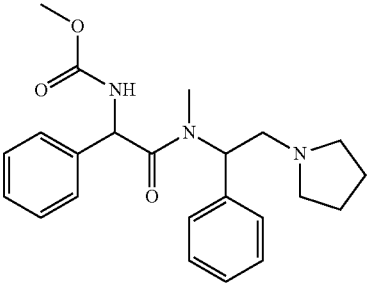 [SMILES: COC(=O)NC(C(=O)N(C)C(CN1CCCC1)c1ccccc1)c1ccccc1] |
| MCKK-8 (210) | 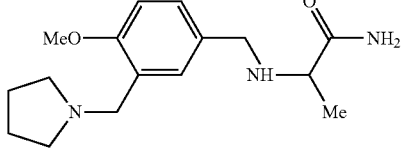 | 0.23 | 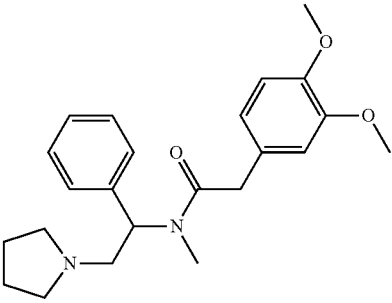 [SMILES: COc1ccc(CC(=O)N(C)C(CN2CCCC2)c2ccccc2)cc1OC] |
| MCKK-9 (253) | 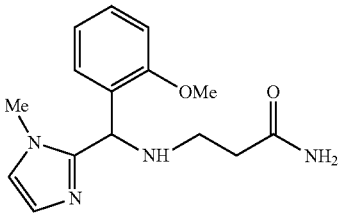 [SMILES: COc1ccccc1C(NCCC(N)=O)c1nccn1C] | 0.19 | 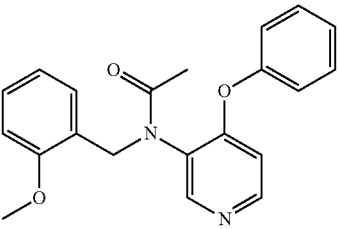 [SMILES: COc1ccccc1CN(C(C)=O)c1cnccc1Oc1ccccc1] |
| MCKK-10 (269) | 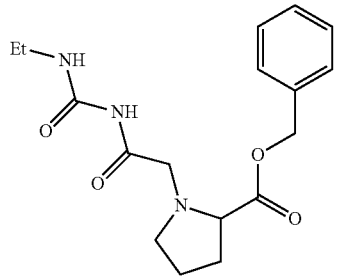 [SMILES: CCNC(=O)NC(=O)CN1CCCC1C(=O)OCc1ccccc1] | 0.27 | 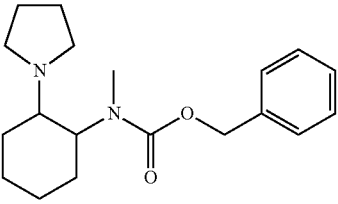 [SMILES: CN(C(=O)OCc1ccccc1)C1CCCCC1N1CCCC1] |

TABLE 1-continued

List of the 22 tested compounds and their corresponding chemical structure, DOCK scoring rank from the virtual screening experiment, and extended connectivity fingerprint maximum distance 4 (ECFP4)-based Tanimoto similarity coefficient (Tc) to the most similar known opioid ligand in the ChEMBL database.

| Compound (Rank) | Structure | ECFP4 based $T_c$ | Most similar known opioid ligand |
|---|---|---|---|
| MCKK-11 (276) | 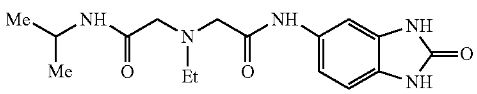 [SMILES: CCN(CC(=O)Nc1ccc2[nH]c(=O)[nH]c2c1)CC(=O)NC(C)C] | 0.15 | |
| MCKK-12 (346) | 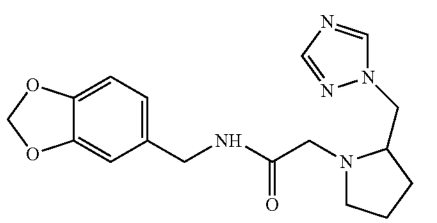 [SMILES: O=C(CN1CCCC1Cn1cncn1)NCc1ccc2c(c1)OCO2] | 0.29 | |
| MCKK-13 (347) | 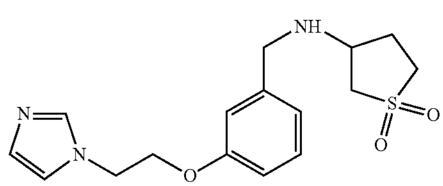 [SMILES: O=S1(=O)CCC(NCc2cccc(OCCn3ccnc3)c2)C1] | 0.17 | |
| MCKK-14 (360) | 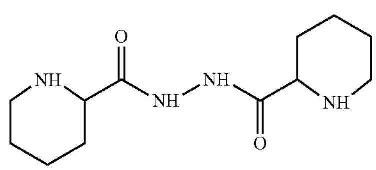 [SMILES: O=C(NNC(=O)C1CCCCN1)C1CCCCN1] | 0.21 | |
| MCKK-15 (379) | 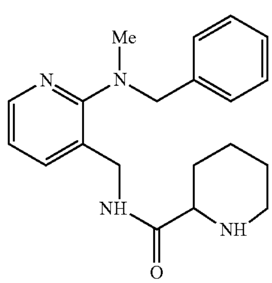 [SMILES: CN(Cc1ccccc1)c1ncccc1CNC(=O)C1CCCCN1] | 0.20 | |

TABLE 1-continued

List of the 22 tested compounds and their corresponding chemical structure, DOCK scoring rank from the virtual screening experiment, and extended connectivity fingerprint maximum distance 4 (ECFP4)-based Tanimoto similarity coefficient (Tc) to the most similar known opioid ligand in the ChEMBL database.

| Compound (Rank) | Structure | ECFP4 based $T_c$ | Most similar known opioid ligand |
|---|---|---|---|
| MCKK-16 (402) | 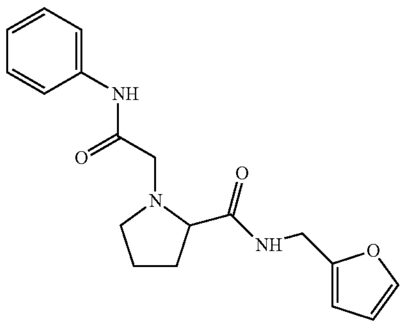 [SMILES: O=C(CN1CCCC1C(=O)NCc1ccco1)Nc1ccccc1] | 0.27 | |
| MCKK-17 (403) | 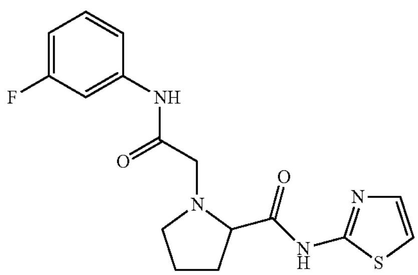 [SMILES: O=C(CN1CCCC1C(=O)Nc1nccs1)Nc1cccc(F)c1] | 0.25 | |
| MCKK-18 (404) | 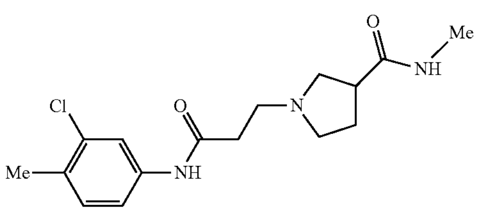 [SMILES: CNC(=O)C1CCN(CCC(=O)Nc2ccc(C)c(Cl)c2)C1] | 0.25 | |
| MCKK-19 (411) | 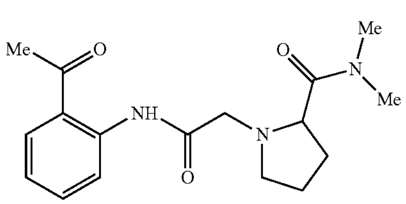 [SMILES: CC(=O)c1ccccc1NC(=O)CN1CCCC1C(=O)N(C)C] | 0.21 | |

TABLE 1-continued

List of the 22 tested compounds and their corresponding chemical structure, DOCK scoring rank from the virtual screening experiment, and extended connectivity fingerprint maximum distance 4 (ECFP4)-based Tanimoto similarity coefficient (Tc) to the most similar known opioid ligand in the ChEMBL database.

| Compound (Rank) | Structure | ECFP4 based $T_c$ | Most similar known opioid ligand |
|---|---|---|---|
| MCKK-20 (427) | 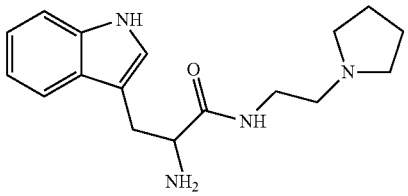 [SMILES: NC(Cc1c[nH]c2ccccc12)C(=O)NCCN1CCCC1] | 0.31 | 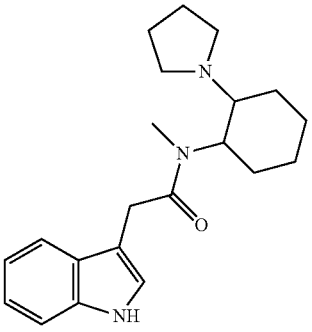 [SMILES: CN(C(=O)Cc1c[nH]c2ccccc12)C1CCCCC1N1CCCC1] |
| MCKK-21 (452) | 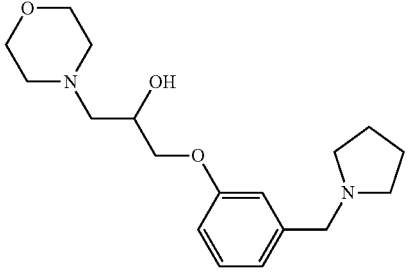 [SMILES: OC(COc1cccc(CN2CCCC2)c1)CN1CCOCC1] | 0.23 | 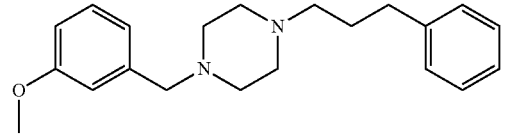 [SMILES: COc1cccc(CN2CCN(CCCc3ccccc3)CC2)c1] |
| MCKK-22 (472) | 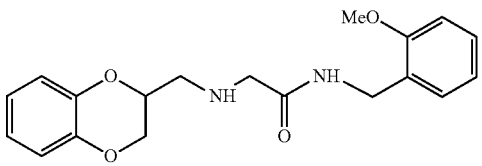 [SMILES: COc1ccccc1CNC(=O)CNCC1COc2ccccc2O1] | 0.20 | 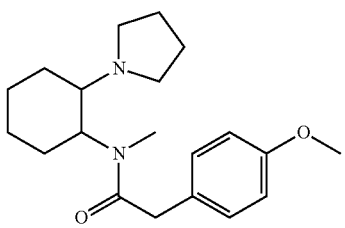 [SMILES: COc1ccc(CC(=O)N(C)C2CCCCC2N2CCCC2)cc1] |

Similarity between these molecules and the 9,934 opioid receptor ligands that are annotated in the ChEMBL database was quantified using an in-house script in R language that calculates Tanimoto coefficients ($T_c$) to the nearest neighbors based on extended connectivity fingerprint maximum distances 4 (ECFP4) and the protocol as described in (Negri et al., 2012). $T_c$ values range from 0 to 1, with the 0 value indicating maximally dissimilar compounds and 1 indicating maximally similar ones (Rogers et al., 2005). As suggested in the literature (Wawer et al., 2010), molecules are considered reasonably similar if their $T_c$ value is above 0.40. Molecules for testing were purchased from commercial vendors. Specifically, compounds MCKK-1, MCKK-4, MCKK-8, MCKK-15, MCKK-18 and MCKK-21-22 were obtained from ChemBridge, MCKK-2 from the National Cancer Institute of the National Institutes of Health, MCKK-3 from Labotest, MCKK-5-7, MCKK-9-13, MCKK-16-17 and MCKK-19 from Enamine, MCKK-14 from Florida Heterocyclic Compounds, and MCKK-20 from Molecular Diversity Preservation International.

Constructs for Expression Vectors and Transfection

The cDNAs for human KOP (hKOP) receptor and the G protein $G\alpha_{oB}$ were obtained from the Missouri S&T cDNA Resource Center. For arrestin recruitment experiments, full-length Renilla luciferase 8 (RLuc8, provided by S. Gambhir) was fused in-frame to the C terminus of the hKOP receptor in the pcDNA3.1 vector. The following human G protein constructs were provided by C. Gales (Gales et al., 2006; Sauliere et al., 2012): $G\alpha_{oB}$ with RLuc8 inserted at position 91 ($G\alpha_{oB}$-RLuc8); untagged $G\beta_1$ (β1); untagged $G\gamma_2$ (γ2). The human γ2 subunit was fused to full-length mVenus at its N terminus (mVenus-γ2), and the fusion construct human arrestin3-mVenus was used as previously described (Klewe et al., 2008). All constructs were confirmed by sequencing analysis. A total of 20 μg of plasmid cDNA (e.g. 0.2 μg of hKOR-RLuc8, 15 μg of arrestin3-mVenus, and 4.8 μg of pcDNA3.1) was transfected into HEK-293T cells using polyethylenimine (Polysciences Inc., Warrington, Pa.) in a 1:3 ratio in 10-cm dishes. Cells were maintained in culture with DMEM supplemented with 10% FBS. The transfected ratio among receptor, Gα, β1, and γ2, or arrestin was optimized by testing various ratios of plasmids encoding the different sensors. Experiments were performed 48 hours after transfection.

Membrane Preparations and Binding Assays

Two days after transfection with human KOP receptor and $G\alpha_{oB}$, HEK293T cells were lysed and membranes were prepared in HEPES buffer (NaCl 140 mM, KCl 5.4 mM, HEPES 25 mM, EDTA 1 mM, MgCl$_2$ 2 mM, BSA 0.006%, pH 7.4) using a Polytron homogenizer. Membranes were incubated with $^3$H-diprenorphine (0.3 nM) (PerkinElmer, Waltham, Mass.) at room temperature for 1 hour in a final volume of 1 ml, in the absence or presence of various concentrations of each small-molecule selected from the virtual screening. Membranes were then harvested using a Brandel cell harvester through a Whatman FPD-24 934AH glass-fiber filter and washed three times with ice-cold wash Buffer (Tris-HCl 10 mM, NaCl 120 mM, pH 7.4). Non-specific binding was determined using 400 nM of NorBNI.
BRET-Based G Protein Activation, Arrestin Recruitment and cAMP Accumulation Assays BRET was performed as described (Guo et al., 2008). Briefly, two days after transfection, cells were harvested, washed, and re-suspended in a phosphate-buffered saline (PBS) solution. Approximately 200,000 cells/well were distributed in 96-well plates, and 5 μM coelenterazine H (luciferase substrate) was added to each well. Five minutes after the addition of coelenterazine H, ligands were added to each well, and after 2 minutes for G protein activation or 5 minutes for arrestin recruitment, the BRET signal was determined by quantifying and calculating the ratio of the light emitted by mVenus, the energy acceptor (510-540 nm), over that emitted by RLuc8, the energy donor (485 nm). The drug-induced BRET signal was normalized, taking the $E_{max}$ of the ethylketocyclazocine (EKC)-induced response as 100%. To measure cAMP accumulation, a BRET-based cAMP in a previously described YFP-Epac-RLuc (CAMYEL) assay was used (Jiang et al., 2007). Gα$_{oB\ B}$, β1, and γ2 were co-expressed to enhance the signal-to-noise ratio, and the cells were treated for 5 minutes with 100 μM forskolin prior to stimulation (Jiang et al., 2007). The data were normalized and represented as the percentage of forskolin-stimulated cAMP accumulation with 0 defined as the maximal inhibition elicited by EKC.

Chemical Synthesis of MCKK-17 Stereoisomers

All reagents purchased from chemical suppliers were used without further purification, and reactions were monitored using thin-layer chromatography (TLC) on 0.25 mm Analtech GHLF silica gel plates using EtOAc/n-hexanes and visualized at 254 nm. Column chromatography was performed on silica gel (40-63 μm particle size, 230-400 mesh) from Sorbent Technologies (Atlanta, Ga.). NMR spectra were recorded on either a Bruker DRX-400 with a H/C/P/F QNP gradient probe or a Bruker Avance AV-III 500 with a dual carbon/proton cryoprobe using δ values in ppm as standardized from tetramethylsilane (TMS) and J (Hz) assignments for $^1$H resonance coupling and $^{13}$C fluorine coupling. High resolution mass spectrometry data were collected on a LCT Premier (Waters Corp.) time-of-flight mass spectrometer. Analytical HPLC was performed on an Agilent 1100 Series Capillary HPLC system with diode array detection at 254.8 nm on a CRIRALCEL OD-H column (4.6×150 mm), Daicel Chemical Industries, Ltd. using isocratic elution in 97% hexanes and 3% 2-Propanol at a flowrate of 1.25 mL/min.

General procedure for the synthesis of tert-butyl 2-(thiazol-2-ylcarbamoyl)pyrrolidine-1-carboxylate (2S and 2R)

A mixture of N-(tert-butoxycarbonyl)-L-proline (1S) or N-(tert-butoxycarbonyl)-D-proline (1R) (2.3 mmol) and 1,1'-carbonyldiimidazole (2.9 mmol) in anhydrous CH$_2$Cl$_2$ (20 mL) was stirred at room temperature under an argon atmosphere. After 1 hour, 2-aminothiazole (2.3 mmol) was added and the resulting mixture was stirred overnight. H$_2$O (30 mL) was added and the mixture was extracted with CH$_2$Cl$_2$ (3×20 mL). The combined organic portion was then dried (Na$_2$SO$_4$). Removal of the solvent under reduced pressure afforded a crude residue that was subjected to FCC (eluent: EtOAc/Hex, 1:1) to yield a fluffy white solid.

(S)-tert-butyl 2-(thiazol-2-ylcarbamoyl)pyrrolidine-1-carboxylate (2S)

Yield 501 mg (72.3%): $^1$H NMR (400 MHz, DMSO) δ 12.27 (s, 1H), 7.48 (d, J=3.6, 1H), 7.22 (d, J=3.6, 1H), 3.48-3.38 (m, 1H), 2.54-2.47 (m, 2H), 2.21 (dd, J=10.3, 14.8, 1H), 1.97-1.73 (m, 3H), 1.31 (d, J=67.9, 9H). $^{13}$C NMR (126 MHz, CDCl$_3$) δ 169.82, 158.16, 156.39, 137.60, 113.53, 81.26, 60.88, 59.94, 47.34, 31.04, 27.71, 24.61, 23.97. HRESIMS (m/z); [M+H] (calculated for C$_{13}$H$_{20}$N$_3$O$_3$S, 298.1225). found 298.1218.

(R)-tert-butyl 2-(thiazol-2-ylcarbamoyl)pyrrolidine-1-carboxylate (2R)

Yield 437 mg (63.3%): $^1$H NMR (400 MHz, DMSO) δ 12.27 (s, 1H), 7.48 (d, J=3.6, 1 H), 7.22 (d, J=3.6, 1 H), 3.48-3.38 (m, 1H), 2.54-2.47 (m, 2H), 2.21 (dd, J=10.3, 14.8, 1H), 1.97-1.73 (m, 3H), 1.31 (d, J=67.9, 9H). $^{13}$C NMR (126 MHz, CDCl$_3$) δ 169.82, 158.16, 156.39, 137.60, 113.53, 81.26, 60.88, 59.94, 47.34, 31.04, 27.71, 24.61, 23.97. HRESIMS (m/z); [M+H] (calculated for C$_{13}$H$_{20}$N$_3$O$_3$S, 298.1225). found 298.1229.

General procedure for the synthesis of 1-(2-(3-fluorophenylamino)-2-oxoethyl)-N-(thiazol-2-yl)pyrrolidine-2-carboxamide (MCKK-17S and MCKK-17R)

A solution of 2S or 2R (1.0 eq) in a mixture of TFA/CH$_2$Cl$_2$ (1:2, 10 mL/mmol) was stirred for 30 minutes at room temperature. The solvent was then removed under reduced pressure solution to give a brown oil that was used without further purification. A mixture of the oil, 2-chloro-N-(3-fluorophenyl)acetamide (Ma et al., 2011; Gu et al., 2010), K$_2$CO$_3$ (3.0 eq), and a catalytic amount of NaI, and DMF (8 mL/mmol) was stirred at 80° C. overnight. The reaction was cooled to room temperature then poured into H$_2$O (10 mL/mL DMF), and the mixture was extracted with EtOAc (3×20 mL). The combined organic portion was then washed with brine (20 mL) and dried (Na$_2$SO$_4$). The solvent was then removed under reduced pressure and the resulting residue was purified by column chromatography (eluent: EtOAc/Hex, 7:3) to afford an oil that was crystallized from Et$_2$O as a white solid.

(S)-1-(2-(3-fluorophenylamino)-2-oxoethyl)-N-(thiazol-2-yl)pyrrolidine-2-carboxamide (MCKK-17S)

Yield 32 mg (5.7%) from 496 mg of 2S; $^1$H NMR (500 MHz, DMSO) δ 12.00 (s, 1H), 10.22 (s, 1H), 7.64-7.56 (m, J=1.3, 10.5, 1 H), 7.48 (d, J=3.6, 1 H), 7.36 (h, J=8.2, 2H), 7.23 (d, J=3.5, 1H), 6.89 (ddd, J=3.1, 5.6, 11.6, 1H), 3.68 (dd, J=4.4, 9.4, 1H), 3.62 (d, J=16.5, 1H), 3.42 (d, J=16.5, 1H), 3.24-3.15 (m, 1H), 2.66 (dd, J=8.7, 15.7, 1H), 2.28-2.17 (m, J=9.0, 12.3, 1H), 1.94-1.75 (m, 3H). $^{13}$C NMR (126 MHz, DMSO) δ 173.02, 169.71, 161.98 (d, $^1J_{CF}$=241.31), 157.55, 140.17 (d, $^3J_{CF}$=11.07), 137.52, 130.24 (d, $^3J_{CF}$=9.50), 115.11 (d, $^4J_{CF}$=2.48), 113.53, 109.80 (d, $^2J_{CF}$=21.06), 106.14 (d, $^3J_{CF}$=26.06), 66.20, 57.85, 53.98, 30.38, 24.21. HRESIMS (m/z); [M+Na] (calc for $C_{16}H_{17}FN_4O_2SNa$, 371.0954). found 371.0951; Chiral $HPLC_{OD-H}$ $t_r$=10.649 min.

(R)-1-(2-(3-fluorophenylamino)-2-oxoethyl)-N-(thiazol-2-yl)pyrrolidine-2-carboxamide (MCKK-17R)

Yield 164 mg (42.7%) from 330 mg of 2R; $^1$H NMR (500 MHz, DMSO) δ 12.00 (s, 1H), 10.22 (s, 1H), 7.64-7.56 (m, J=1.3, 10.5, 1 H), 7.48 (d, J=3.6, 1 H), 7.36 (h, J=8.2, 2H), 7.23 (d, J=3.5, 1 H), 6.89 (ddd, J=3.1, 5.6, 11.6, 1 H), 3.68 (dd, J=4.4, 9.4, 1 H), 3.62 (d, J=16.5, 1H), 3.42 (d, J=16.5, 1H), 3.24-3.15 (m, 1H), 2.66 (dd, J=8.7, 15.7, 1H), 2.28-2.17 (m, J=9.0, 12.3, 1H), 1.94-1.75 (m, 3H). $^{13}$C NMR (126 MHz, DMSO) δ 173.02, 169.71, 161.98 (d, $^1J_{CF}$=241.31), 157.55, 140.17 (d, $^3J_{CF}$=11.07), 137.52, 130.24 (d, $^3J_{CF}$=9.50), 115.11 (d, $^4J_{CF}$=2.48), 113.53, 109.80 (d, $^2J_{CF}$=21.06), 106.14 (d, $^3J_{CF}$=26.06), 66.20, 57.85, 53.98, 30.38, 24.21. HRESIMS (m/z); [M H] (calc for $C_{16}H_{18}FN_4O_2S$, 349.1135). found 349.1127; Chiral $HPLC_{OD-H}$ $t_r$=12.491 min.

Example 2

Structure-Based Identification of Novel Chemotypes Targeting the KOP Receptor 4,554,059 commercially-available, "lead-like" compounds from the ZINC database (Irwin et al., 2005) were screened in silico based on complementarity with the crystallographic binding mode of JDTic into the KOP receptor binding pocket. The 500 top-scoring docking hits (FIG. 4; 0.01% of the docked library) were visually inspected and prioritized based on features that an automatic molecular docking screen does not take into account. Specifically, molecules were selected based on the following criteria: a) chemotype diversity; b) the presence of polar interactions between the ligand and the Asp138$^{3.32}$ residue; c) interactions with KOP receptor residues in the binding pocket that are different in DOP and MOP receptors, d) limited flexibility, e) different binding modes from classical alkaloids as revealed by DOP (Granier et al., 2012) and MOP (Manglik et al., 2012) receptor crystal structures, and f) purchasability, i.e., molecules were readily available for purchase. Based on these criteria, twenty-two small molecules were purchased from the set of 500 highest-scored compounds. These molecules, labeled MCKK-1-22 in Table 1, corresponded to the DOCK scoring ranks 1, 80, 87, 97, 111, 127, 137, 210, 253, 269, 276, 346, 347, 360, 379, 402, 403, 404, 411, 427, 452, and 472, respectively. As shown in Table 1 above, these compounds were found to be significantly different from annotated opioid receptor ligands in the ChEMBL database, as indicated by small ECFP4-based $T_c$ values Wawer et al., 2010). These data confirm the chemotype novelty of all selected agents.

Example 3

Figure 2:
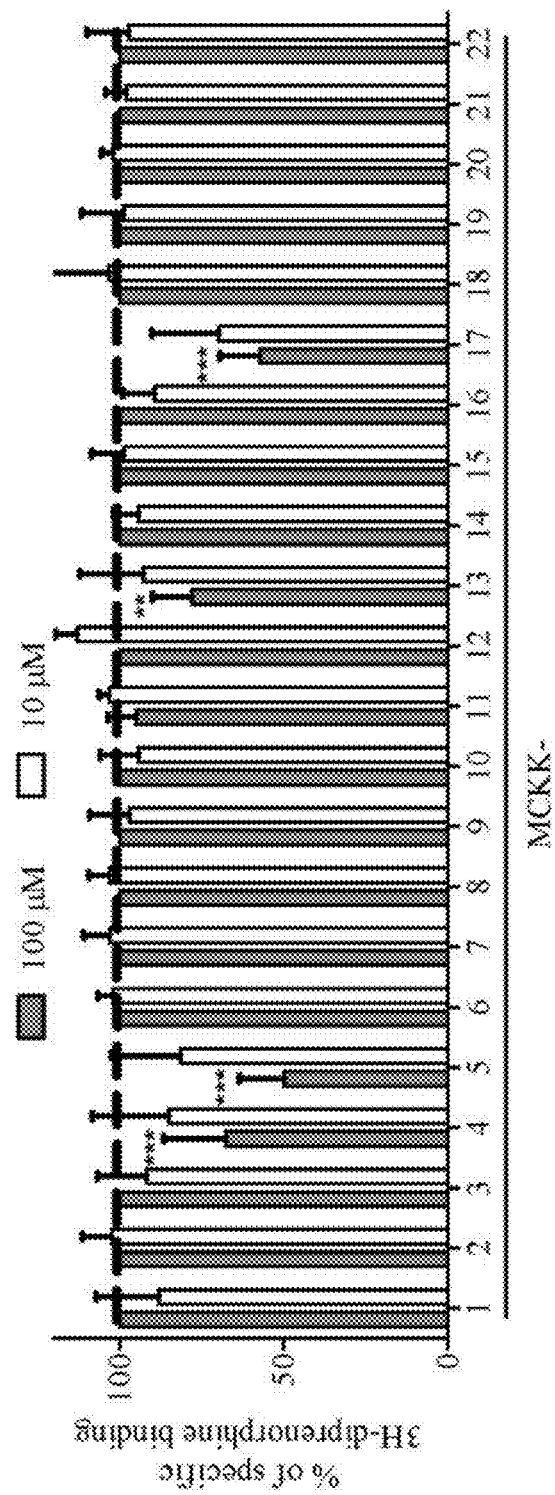
FIG. 2 shows the competitive inhibition of $^3$H-diprenorphine binding at the hKOP receptor. Membranes of HEK293T cells transfected with the hKOP receptor and GaoB were prepared and incubated with $^3$H-diprenorphine (0.3 nM) at room temperature for 1 hour in a final volume of 1 ml, in the absence or presence of 10 or 100 μM of each small-molecule from virtual screening. Only MCKK-4, MCKK-5, MCKK-13 and MCKK-17(R/S) significantly inhibited $^3$H-diprenorphine binding at 100 μM (n=3). A one-way analysis of variance test with 99.9% confidence intervals (p<0.001) followed by a Tukey's multiple test comparison was performed to determine the significance of each value as compared to vehicle.

One of the Top-Scoring Docked Molecules is a Selective Agonist at the KOP Receptor The primary experimental testing of MCKK-1-22 consisted of performing a competitive inhibition binding assay at the hKOP receptor. Membranes of HEK293T cells transfected with the hKOP receptor and $G\alpha_{oB}$ were prepared and incubated with $^3$H-diprenorphine (0.3 nM) in the absence or presence of 10 or 100 μM of each small-molecule from the virtual screening. Four molecules, MCKK-4, MCKK-5, MCKK-13 and MCKK-17 partially but significantly inhibited $^3$H-diprenorphine binding (FIG. 2) at 100 μM and their properties were therefore further investigated.

To assess whether any of these molecules had agonistic activity, a BRET-based G protein activation assay where the hKOP receptor was co-expressed in HEK293T cells with $G\alpha_{oB}$-RLuc8, β1, and mVenus-γ2 was used. The drug-induced BRET signal is interpreted as a dissociation of and/or conformational change within the Gαβγ complex, and thus, as the activation of the co-expressed G protein. Among the selected molecules, only the racemic mixture MCKK-17R/S activated $G\alpha_{oB}$ with a potency of 8.3±4.0 μM (FIG. 1A).

The chemical synthesis of the R and S stereoisomers of MCKK-17 using commercially available N-(tert-butoxycarbonyl)-L-proline (1R) or N-(tert-butoxycarbonyl)-D-proline (1S) (see synthetic scheme below) was done to identify the active molecule.

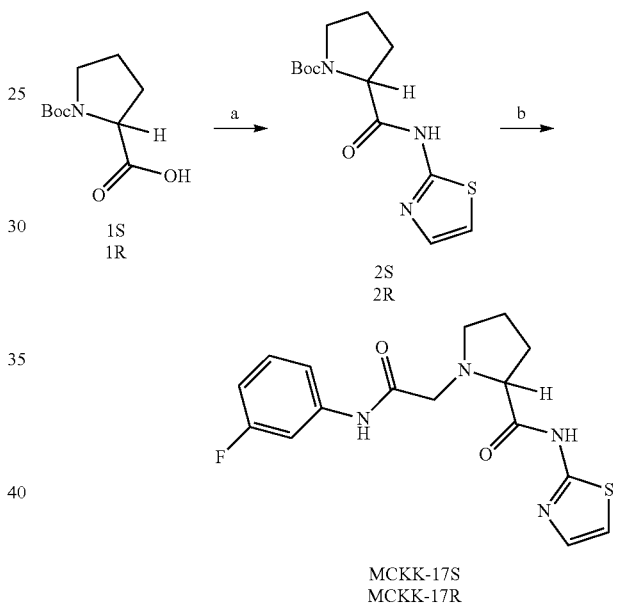

Reagents and conditions used were: (a) i. 1,1'-Carbonyldiimidazole, CH$_2$Cl$_2$, 1 hour; ii. 2-Aminothiazole, 16 hours; (b) i. TFA/CH$_2$Cl$_2$, 1:2, 30 minutes; ii. 2-Chloro-N-(3-fluorophenyl)acetamide, NaI, K$_2$CO$_3$, DMF, 80° C., 16 hours.

The appropriate proline was coupled to 2-aminothiazole using 1,1'-carbonyldiimidazole (CU) in CH$_2$Cl$_2$ under anhydrous conditions (Luo et al., 2005; Yu et al., 2011) to afford the corresponding Boc-protected thiazoles (2R and 2S). Removal of the Boc group under acidic conditions followed by alkylation with 2-chloro-N-(3-fluorophenyl)acetamide (Ma et al., 2011; Gu et al., 2010) under basic conditions in DMF overnight at 80° C. gave stereoisomers MCKK-17S and MCKK-17R. The purity of MCKK-17S and MCKK-17R was determined to be at least 99% by integration of the UV trace from chiral HPLC (data not shown). MCKK-17S resulted in the most active stereoisomer at the hKOP receptor. Indeed, MCKK-17S displayed full agonism relative to EKC at the hKOP receptor with an EC$_{50}$ of 7.2±3.8 μM, whereas MCKK-17R displayed a potency of only 115±9 μM. None of the other molecules, MCKK-4, MCKK-5 and MCKK-13, significantly activated $G_{oB}$ (FIG. 1A), suggesting that, in contrast to MCKK-17R/S, those molecules are antagonists at the hKOP receptor.

Figure 3:
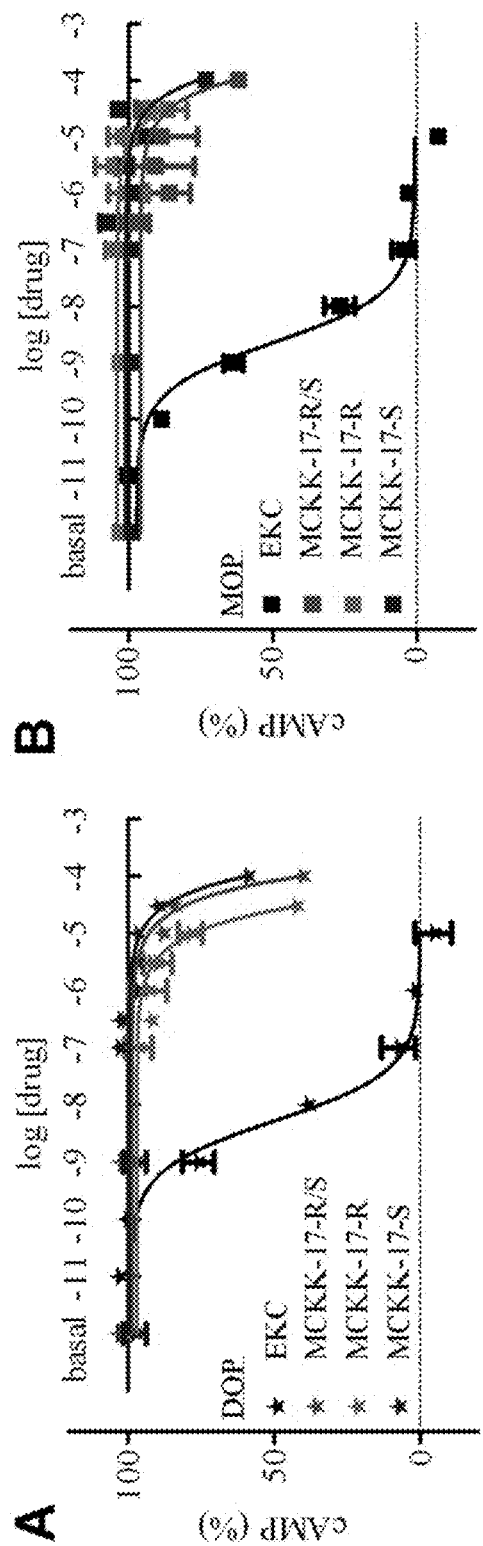
FIG. 3 shows cAMP accumulation inhibition at DOP and MOP receptors. The DOP receptor (FIG. 3A) or MOP receptor (FIG. 3B) was co-expressed with a BRET-based CAMYEL sensor to assay inhibition of forskolin-stimulated cAMP accumulation. The data are normalized and represented as the percentage of forskolin-stimulated cAMP accumulation with 0 defined as the maximal inhibition triggered by EKC. Error bars indicate S.E.

To assess the degree of selectivity of MCKK-4, MCKK-5, MCKK-13, MCKK-17R or MCKK-17S for the hKOP over the DOP and MOP receptors, competitive inhibition of $^3$H-diprenorphine (0.3 nM) binding in the absence or presence of various concentrations of each molecule were performed, and their $K_i$ values for each receptor were determined (Table 2 below).

at the DOP receptor. In contrast, MCKK-17S did not significantly activate the DOP receptor, confirming its selectivity at the hKOP receptor. These results were confirmed using a BRET-based cAMP accumulation inhibition assay (FIG. 1C) to monitor the agonistic activity of the selected molecules at the hKOP receptor (FIG. 1C), as well as at the DOP and MOP receptors (FIG. 3).

TABLE 2

Active compounds and their corresponding chemical structure, DOCK scoring rank from the virtual screening experiment, and binding affinity values ($K_i$). Values are the means ± S.E.M. (n = 3).

| Compound (Rank) | Structure | Ki (µM) KOP | DOP | MOP |
|---|---|---|---|---|
| MCKK-4 (97) | 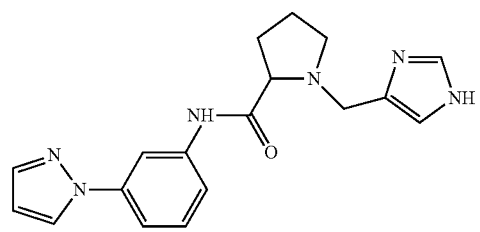 [SMILES: O=C(Nc1cccc(-n2cccn2)c1)C1CCCN1Cc1c[nH]cn1] | 292 ± 209 | 641 ± 192 | 906 ± 836 |
| MCKK-5 (111) | 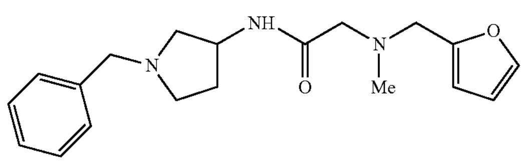 [SMILES: CN(CC(=O)NC1CCN(Cc2ccccc2)C1)Cc1ccco1] | 134 ± 81 | 179 ± 187 | 428 ± 137 |
| MCKK-13 (347) | 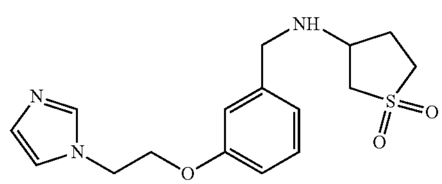 [SMILES: O=S1(=O)CCC(NCc2cccc(OCCn3ccnc3)c2)C1] | 453 ± 27 | 300 ± 99 | >10000 |
| MCKK-17 (403) | 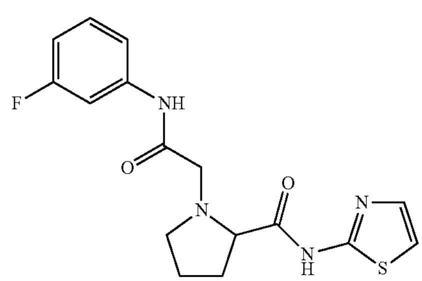 [SMILES: O=C(CN1CCCC1C(=O)Nc1nccs1)Nc1cccc(F)c1] | 17R: 2904 ± 964 17S: 123 ± 38 | 17R: 286 ± 322 17S: >10000 | 17R: 508 ± 636 17S: >10000 |

Consistent with the first experimental testing (FIG. 2), the aforementioned five molecules displayed a relatively weak affinity (Ki values) at the hKOP receptor, between 100 and 500 µM (Table 2). Among them, only MCKK-17S exhibited selectivity for the hKOP receptor with a measured affinity of 123±38 µM at this receptor, and no detectable affinity at DOP and MOP receptors (>1000 µM).

To further assess the selectivity of MCKK-17S for the hKOP receptor (Table 2), we also investigated whether the racemic mixture MCKK-17R/S, as well as the two stereoisomers, displayed agonistic activity at the DOP and MOP receptors (FIG. 1B). Neither the racemic nor the MCKK-17 stereoisomers displayed significant activity at the MOP receptor, and they only weakly activated the DOP receptor (>1000 µM). Notably, MCKK-17R, the less active stereoisomer at the hKOP receptor, was the most active enantiomer Finally, whether MCKK-17 and the corresponding stereoisomers could recruit arrestin was investigated. MCKK-17R/S and MCKK-17S recruited arrestin3, with potencies of 164±38 µM and 123±47 µM, respectively, whereas MCKK-17R only weakly recruited arrestin3 at the highest concentration (potency>1000 µM) (FIG. 1D), consistent with its weaker potency at the hKOP receptor for G protein activation.

The structure-based virtual screening and compound selection criteria yielded the discovery of a novel small-molecule chemotype that acts as a selective, full agonist at the KOP receptor. To the best of the inventors' knowledge, this is the first time that a virtual screening based on an antagonist-bound GPCR crystal structure has identified an agonist. The chemical scaffold of the identified hit refers to a selective KOP receptor compound that has very little similarity with all opioid receptor agonists or antagonists annotated in ChEMBL, and it has never been reported to be an opioid receptor ligand. In summary, MCKK-17S is a promising new lead compound for structure-based ligand optimization aimed at discovering potent non-addictive analgesics. Although the parent compound MCKK-17S is not biased toward G protein activation over arrestin, the chemical scaffold is well suited to structure-guided modifications, raising the prospects of maintaining selectivity while increasing potency and building G protein bias.

Figure 5:
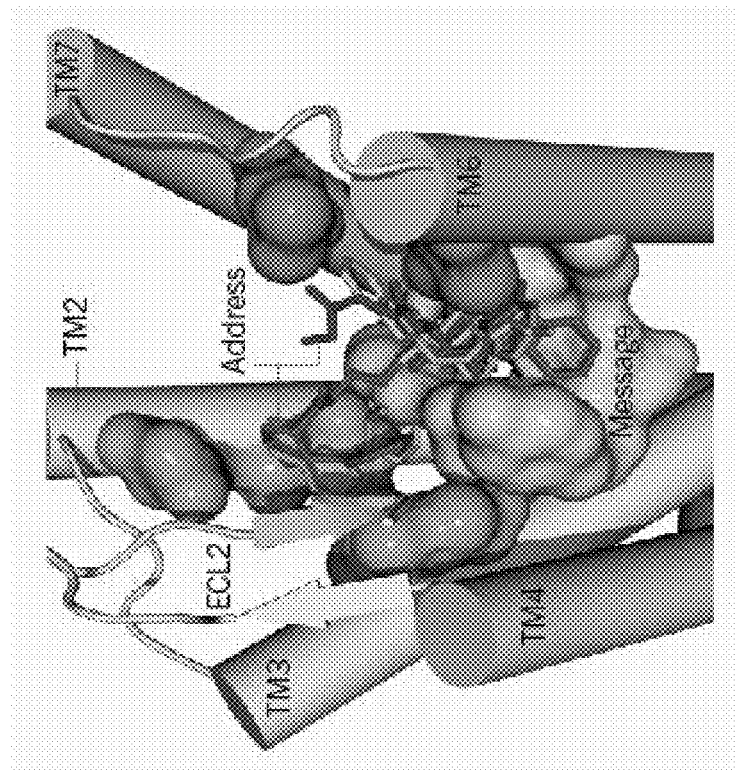
FIG. 5 shows a portion of the crystallized opioid ligand with the KOP receptor. The so-called "message" region of these crystallized opioid ligands (i.e., the chemical moieties that are responsible for opioid efficacy) form interactions with amino-acid residues at the same positions in transmembrane (TM) helices TM3, TM6 and TM7. In contrast, the chemical moieties that are possibly responsible for the selectivity of these ligands (the so-called "address" region) occupy two different areas of the binding pocket, depending on whether the ligand is a classical or non-classical opioid molecule.

The results we have obtained from studies of the KOP receptor support that the recently released high-resolution crystal structures of opioid receptors (Manglik et al., 2012; Granier et aL, 2012; Wu et al., 2012) offer an unprecedented opportunity to discover novel chemotypes targeting these proteins (Filizola, 2012; Filizola et al., 2012). These structures correspond to inactive forms of the receptors that are either bound to classical (i.e., containing the 'morphinan' chemical structure) antagonists, such as β-funaltrexamine for the MOP receptor and naltrindole for the DOP receptor, or other types of selective opioid ligands, such as JDTic for the KOP receptor. The so-called "message" region of these crystallized opioid ligands (i.e., the chemical moieties that are responsible for opioid efficacy) form interactions with amino-acid residues at the same positions in transmembrane (TM) helices TM3, TM6 and TM7 (FIG. 5). In contrast, the chemical moieties that are possibly responsible for the selectivity of these ligands (the so-called "address" region) occupy two different areas of the binding pocket, depending on whether the ligand is a classical or non-classical opioid molecule (Filizola, 2012). Specifically, the address regions of the two morphinans crystallized in the binding pockets of MOP and DOP receptors, i.e., β-funaltrexamine and naltrindole, respectively, were found to interact with TM6 and/or TM7 of the receptor whereas those of the non-classical opioid JDTic appeared to interact predominantly with TM2 and TM3 of the KOP receptor. Notably, although the crystal structure of the KOP receptor corresponds to an inactive conformation, we were able to identify a selective agonist of this receptor. Thus, this crystal structure can serve as a guide for structure-activity studies of other classical agonists at this receptor.

Figure 6:
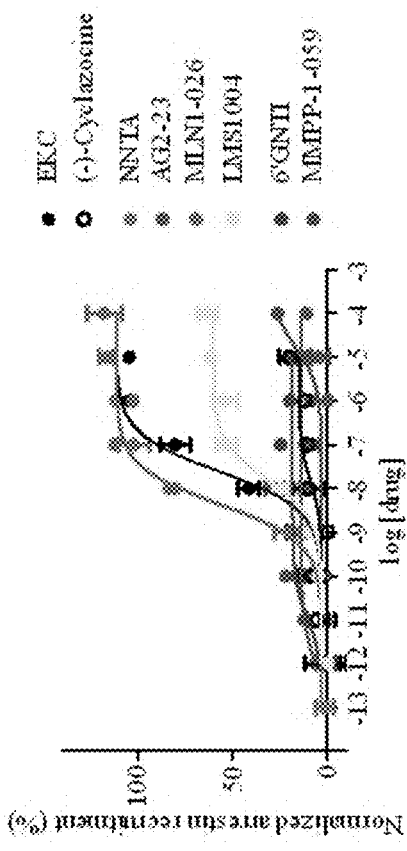
FIG. 6 shows that 6'-GNTI, MMP1-059, AG2-23, and cyclazocine are biased toward G protein activation (FIG. 6A) over arrestin (FIG. 6B), whereas EKC, NNTA, MLN-0126 and LMS1004 resulted in non-biased or partially biased (LMS1004) ligands.
Figure 6:
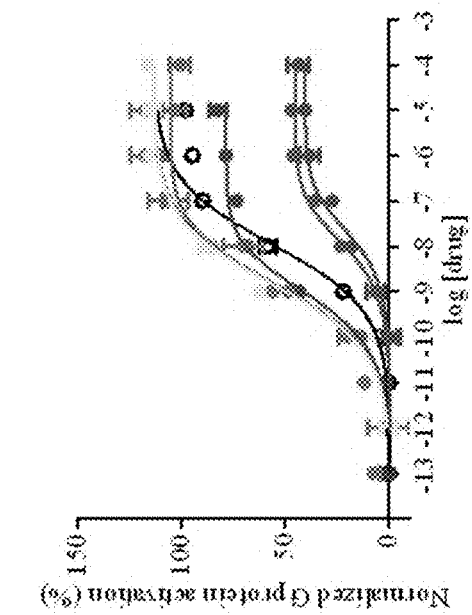

In the search for the molecular determinants that are responsible for KOP receptor ligands to be biased toward G protein activation over arrestin, we docked a series of KOP receptor drugs that we recently tested for possible functional selectivity. Specifically, we used the BRET-based G protein activation and arrestin recruitment assays we mentioned above in its application for MCKK-17 and 6'-GNTI, to assess the possible G protein bias of the following ligands: levorphanol and its analog butorphanol, cyclazocine and its analog EKC, NNTA and its analogs AG2-23, MLN-0126 and LMS1004, as well as U50,488, and 6'-GNTI derivative MMP1-59. 6'-GNTI, MMP1-059, AG2-23, levorphanol, butorphanol, and cyclazocine showed bias toward G protein activation over arrestin, whereas U50,488, EKC, NNTA, MLN-0126 and LMS1004 resulted in non-biased or partially biased (LMS1004) ligands (FIG. 6). Molecular docking of these compounds into the KOP receptor crystal structure was obtained by molecular replacement of the naltrindole molecule into the KOP receptor binding pocket after optimal superposition between the transmembrane regions of the KOP receptor and the naltrindole-bound DOP receptor crystal structures. Standard molecular dynamics simulations of these docked poses were performed to verify conformational stability. Specifically, the atomic coordinates of the T4 lysozyme that are present in the KOP receptor crystal structure were removed and replaced by a low-energy conformation of the intracellular loop 3 (IL3) obtained with the Rosetta ab-initio loop modeling protocol (Rohl et al., 2004). The latter was also used to build the missing extracellular loop 3 (EL3). The resulting receptor model was embedded into an explicit 1-palmitoyl-2-oleoyl-sn-glycero-3-phosphocholine (POPC)/10% cholesterol membrane bilayer using a pre-equilibrated 8×8×10 nm lipid patch hydrated with TIP3P water molecules, and the procedure described in (Kandt et al., 2007). Eight crystallographic water molecules that had been found inside the binding pocket were also added to the system setup, together with a number of $Na^+$ and $Cl^-$ ions used to neutralize the system. The resulting approximately 60,000 atoms systems were then simulated using the CHARMM27 all-atom force field (Mackerll et al., 2004; Mackerell et al., 1998) in GROMACS 4.5.3 (Van Der Spoel et al., 2005). The ligand topologies were obtained from the Paramchem web server and then converted into the GROMACS format using an in-house script. NPT simulations were carried out under periodic boundary conditions, using Parrinello-Rahman and Nose-Hoover algorithms to maintain the pressure at 1 bar and the temperature at 300 K, respectively. Prior to production runs, the systems were equilibrated in 3 steps using different sets of restraints on the protein or the ligand. Specifically, 0.5 ns runs in which protein and ligand heavy atoms were restrained were followed by 1 ns simulations with constraints on the protein backbone and the ligand heavy atoms, and then additional 1.0 ns simulations in which all constraints were released. The standard GROMACS leap-frog algorithm was used with a time step of 2.0 fs, as well as the LINCS algorithm (Hess et al., 1997) to preserve the bond lengths, and the SETTLE algorithm (Miyamoto et al., 1992) to maintain the geometry of water molecules. Lennard-Jones interactions were treated with a twin-range cutoff of 0.9:1.4 nm and an integration time step of 2.0 fs; the neighbor list was updated every 10 steps. Electrostatic interactions were described using the particle-mesh Ewald method (Darden et al., 1993) with a cutoff of 0.9 nm for real-space interactions, and a 0.12-nm grid with fourth-order B-spline interpolation for reciprocal-space interactions.

Example 4

Optimization of Newly Identified Ligand Scaffolds of the KOP Receptor

The objectives of the studies here are: a) to increase the affinity of the newly identified chemical scaffolds at the KOP receptor, b) to understand the source of their efficacy, and c) to transform the identified MCKK-17S agonist into a G-protein biased ligand.

Figure 7:
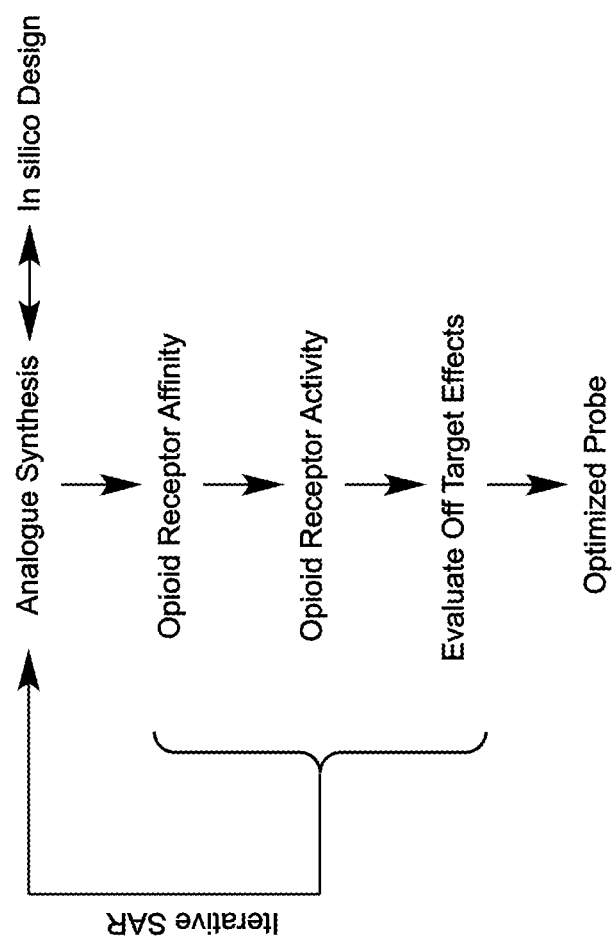
FIG. 7 shows a workflow diagram for screening KOP selective compounds.

The synthetically feasible chemical substitutions that are predicted to improve ligand-receptor interactions based on the results of standard molecular dynamics simulations similar to those recently carried out successfully for the optimization of anti-thrombotic agents (Zhu et al., 2012; Zhu et al., 2010) will be done using the synthetic schema outlined in FIG. 7. Experimental validation will be conducted via functional assays disclosed herein. Specifically, we will use the BRET-based G-protein activation and arrestin recruitment assays at KOP, DOP and MOP receptors, in order to assess the efficacy and selectivity of all newly synthesized molecules at both pathways and for each receptor. We will also perform mutagenesis at the KOP receptor in order to confirm the involvement of the identified residues in the G-protein bias.

The compounds will then be tested for KOP receptor affinity and BRET-based G-protein activation and arrestin recruitment. Computational approaches will be used to assist in rationally selecting compounds for synthesis and in vitro evaluation in order to assess the efficacy and selectivity of all newly synthesized molecules at both pathways and for each receptor. We will also perform mutagenesis at the KOP receptor in order to confirm the involvement of the identified residues in the G-protein bias. It is expected that these tests will identify novel MCKK-17 of differing efficacy.

To that end, the following is the procedure for analogue design and preparation. To further probe the structure-activity relationships of MCKK-17, several positions will be explored. The first feature is the aminothiazole (Site A). Bioisosteric replacements will be tested to further elucidate the influence of this site on affinity and activity. Secondly, the fluoroanilinemoeity will also be evaluated (Site B). In particular, the effect of various aromatic substitutions will be probed. This will focus on finding replacements that enhance affinity and efficacy at KOP receptors. Finally, the effects modifications in both Site A and Site B will be evaluated to determine if these proposed changes are additive.

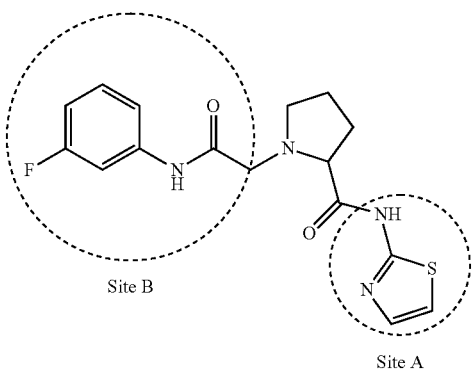

Site A

To investigate the aminothiazole group of MCKK-17 (Site A), we will replace the aminothiazole group of MCKK-17 with other substituents, such as those identified previously herein. It is predicted that such replacement will enhance affinity and activity at KOP receptors. This approach has been used successfully in identifying analogues that have increased affinity and potency. To test this hypothesis, we are synthesizing a series of modified analogues of MCKK-17. The treatment of the appropriate proline with carbonyl diimidazole under basic conditions followed by the appropriate aminoaromatic group will afford the corresponding amide analogues. (See Scheme 1 below). First, we will explore commercially available aminoaromatics. Second, we will systematically explore the degree of alkylation necessary on the amido group formed.

Scheme 1

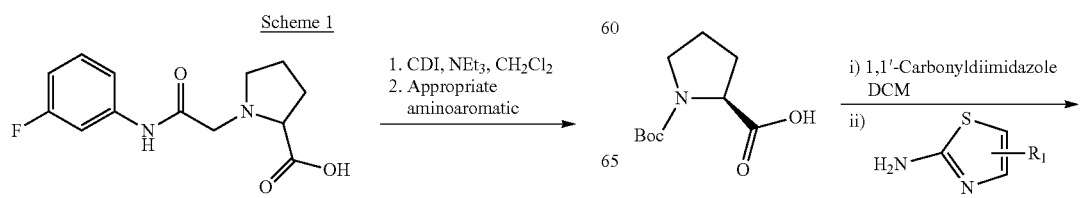

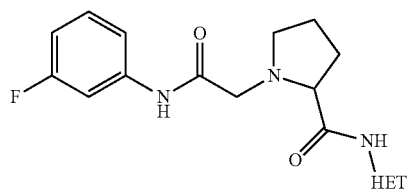

Site B

To investigate the fluoroaniline group of MCKK-17 (Site B), we will replace the fluoroaniline group of MCKK-17 with other substituents, such as those identified previously herein. It is predicted that such replacement will enhance affinity and activity at KOP receptors. We will probe alternative structural modifications of the phenacyl group and their effects on signaling. The coupling of the amino group of the substituted proline and the appropriate halogenated acetamide using previously developed chemistry will afford the corresponding aryl acetamides. (See Scheme 2 below). Commercially available anilines with varying aromatic substituents will be utilized first. The influence of electronics and lipophilicity will be probed using the Topliss tree to guide analogue preparation. The role of the spacer between the amide group and the aryl group will also be investigated.

Scheme 2

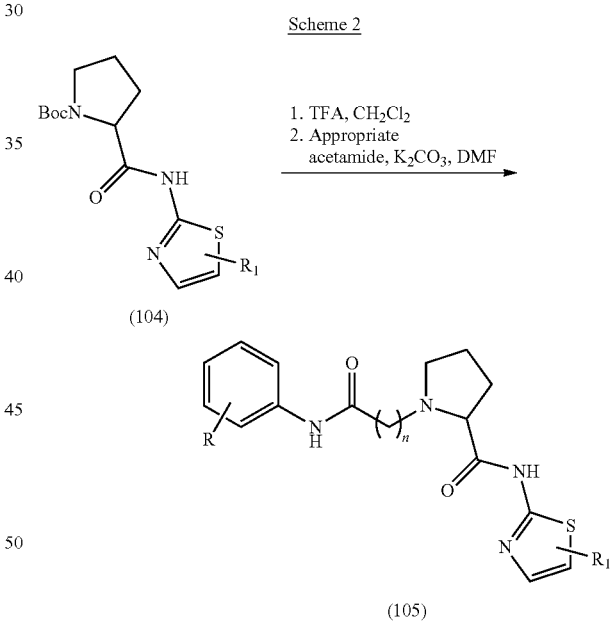

To make compound (104) shown in Scheme 2 above, we will use a procedure adapted from Luo et al. (2005) and Yu et al. (2011). The synthetic scheme is as follows:

-continued

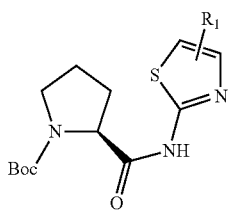

The procedure is as follows. To a stirring solution of (S)-1-(tert-butoxycarbonyl)pyrrolidine-2-carboxylic acid (10 mmol) in $CH_2Cl_2$ (40 mL) under an atmosphere of argon is added 1,1'-carbonyldiimidazole, and the resulting mixture is allowed to stir at room temperature. After 1 hour, to the solution is added substituted 2-aminothiazole (10 mmol), and the resulting solution is allowed to stir overnight. Upon completion of the reaction, the solution is poured into $H_2O$ (40 mL) and extracted with $CH_2Cl_2$ (3×20 mL). The combined organic portion is washed with brine (20 mL) and dried ($Na_2SO_4$). Solvent is removed under reduced pressure and the resulting residue is subjected to flash column chromatography using a mixture of EtOAc/hexanes.

To make the appropriate acetamide shown in Scheme 2 above, we will use a procedure adapted from Ma et al. (2011) and Gu et al. (2010). The synthetic scheme is as follows:

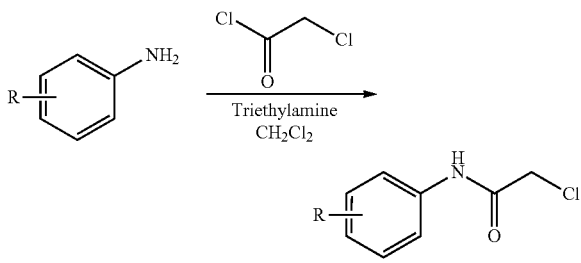

The procedure is as follows. To a stirring solution of substituted aniline (10 mmol), triethylamine (12 mmol), and anhydrous $CH_2Cl_2$ (10 mL) at 0° C. and under an atmosphere of argon is added chloroacetylchloride (12 mmol) dropwise. Upon complete addition of chloroacetyl chloride, the solution is allowed to warm to room temperature and stirred overnight. Solvent is removed under reduced pressure, and water (50 mL) is added to the remaining residue. The resulting precipitate is then filtered, recrystalized from diethyl ether, and used without further purification.

We will also prepare MCKK-17 analogues with modifications in both Site A and Site B. We expect that the changes to the diamino group (Site A) and phenacyl group (Site B) are additive. To test this hypothesis, we will prepare a series of analogues that incorporate both a replacement of the diamino group and a replacement of the phenacyl group.

We will also evaluate selected analogues for off-target affinity. Compounds will be first tested for radioligand binding to mu and delta opioid receptors, as well as examined for off-target binding to other central nervous system binding sites. Functional validation of off-target effects may be followed up in cell lines expressing the appropriate receptor. Selected analogues may also be evaluated in the BioPrint Full battery of assays at CEREP (Seattle, Wash.). The BioPrint profile is mainly based on target diversity and includes 105 binding assays (non-peptide, peptide and nuclear receptors, ion channels and amine transporters), 34 enzyme assays (including 10 kinases, 10 proteases and 5 PDEs), as well as 20 ADME-Tox assays (solubility, absorption, LMS and CYP-mediated drug-drug interaction). More than 70% are human targets. The 159 assays of this profile represent a rationalized panel from a larger assay collection in the database, selected for highest information content. Criteria for compounds to undergo further testing (behavioral assessment of antinociceptive efficacy) will be affinity for MOR and DOR greater than or equal to 500 nM and greater than 100-fold selectivity over other targets.

Enhanced molecular dynamic simulations to characterize ligand-specific conformations of the KOP receptor may be carried out using a computational strategy the Filizola lab has recently tested on prototypic GPCRs that bind to diffusible ligands, either in protomeric (Provasi et al., 2011) or dimeric forms (Fribourg et al., 2011). The rationale for carrying out these simulations is that the molecular determinants responsible for ligand potency or bias agonism may not reside in the binding pocket or its immediate vicinity, but rather involve long-range conformational changes, which may be difficult to capture by standard molecular dynamics approaches. Briefly, the computational strategy recently developed enables sampling of the conformational transition of a GPCR system from inactive to active conformations within an explicit membrane bilayer, using statistically independent adiabatic biased molecular dynamics (ABMD) simulations (Marchi et al., 1999) and, as a reaction coordinate, the mean square deviation from the TM backbone atoms of the target conformation. To obtain information about the relative stability of the states populated by the receptor system along the pre-calculated ABMD paths, the metadynamics path variable method (Branduardi et al., 2007) is applied using as reaction coordinates two variables that describe the position of the coordinate system (X) along, and the distance from, the pre-assigned ABMD paths (s(X) and z(X), respectively; see equations in (Provasi et al., 2011)). Thus, we will first carry out several different statistically-independent ABMD runs (Marchi et al., 1999) in a pre-equilibrated, explicit palmitoyl-oleoyl-phosphatidyl-choline (POPC): 10% cholesterol-water environment to simulate the conformational transition between ligand-free inactive and activated KOP receptor models built by homology modeling using the inactive KOP receptor crystal structure (PDB: 4DJH (Wu et al., 2012)) and the active beta2-adrenergic receptor crystal structure (PDB: 3SN6 (Rasmussen et al, 2011)) as templates for the transmembrane domain, and the Rosetta algorithm (Wang et al., 2007) for the missing loops. The system will be coupled to temperature and pressure baths using Nosé-Hoover and Parrinello-Rahman algorithms. A harmonic bias potential will be applied to the coordinate system whenever the thermal fluctuations tend to increase the value of root mean square deviation with respect to the target, active structure. To validate the strategy in its application to the KOP receptor system, the energetically favorable receptor complexes formed by the bias and unbiased ligands assessed in preliminary studies will be simulated using the metadynamics path variable method (Branduardi et al., 2007) to characterize the most energetically favorable receptor conformation for each of these ligands along the ABMD-derived receptor activation pathways (see Provasi et al., 2011 for details of the simulation procedure). The well-tempered metadynamics algorithm in its direct formulation (Barducci et al., 2008) will be used to reconstruct the free-energy of the KOP receptor as a function of the aforementioned path variables s(X) and z(X). The expected outcome of these simulations is that the identified G protein-biased ligands stabilize conformations of the KOP receptor that are distinguishable from those that are stabilized by non-biased ligands. Thus, specific hypotheses of sequence alterations that may either affect ligand-binding or function mediated by the KOP receptor will be assessed experimentally. If validated, the predicted KOP receptor molecular models stabilized by biased agonists can be used in further virtual screening applications which might help limiting the search for novel therapeutics to biased ligands only.

Example 5

Synthesis of a MCKK-17S Analogue

Compound (103), an analogue of MCKK-17S, was made according to Scheme 3 below.

Scheme 3

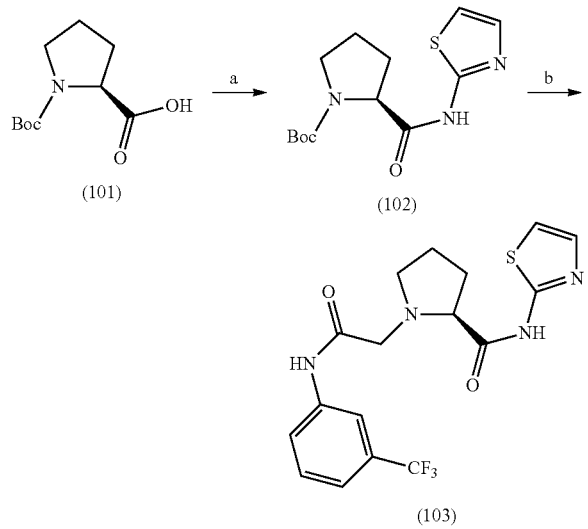

(101)
(102)
(103)

Reagents and Conditions: (a) i) 1,1'-Carbonyldiimidazole, DCM, 1 hr ii) 2-aminothiophene, 16 hrs (b) i) TFA/DCM 1:2, 2 hrs, Concentrate, Ethereal HCl iii) K$_2$CO$_3$, NaI, 2-chloro-N-(3-(trifluoromethyl)phenyl)acetamide, DMF, 65° C., 16 hrs (S)-tert-butyl 2-(thiazol-2-ylcarbamoyl)pyrrolidine-1-carboxylate (compound (102))

A mixture of N-(tert-butoxycarbonyl)-L-proline (compound (101)) (2.3 mmol) and 1,1'-carbonyldiimidazole (2.9 mmol) in anhydrous CH$_2$Cl$_2$ (20 mL) was stirred at room temperature under an argon atmosphere. After 1 hour, 2-aminothiophene (2.3 mmol) was added to the solution and the resulting mixture was stirred overnight. H$_2$O (30 mL) was added to the mixture, and the mixture was extracted with CH$_2$Cl$_2$ (3×20 mL). The combined organic portion was then dried (Na$_2$SO$_4$) and the solvent under reduced pressure to afford a crude residue that was purified by FCC (eluent: EtOAc/Hex), (1:1) to yield 501 mg of a fluffy white solid (72.3%): $^1$H NMR (400 MHz, DMSO) δ 12.27 (s, 1H), 7.48 (d, J=3.6, 1 H), 7.22 (d, J=3.6, 1 H), 3.48-3.38 (m, 1H), 2.54-2.47 (m, 2H), 2.21 (dd, J=10.3, 14.8, 1H), 1.97-1.73 (m, 3H), 1.31 (d, J=67.9, 9H). $^{13}$C NMR (126 MHz, CDCl3) δ 169.82, 158.16, 156.39, 137.60, 113.53, 81.26, 60.88, 59.94, 47.34, 31.04, 27.71, 24.61, 23.97. HRESIMS (m/z); [M+H] (calculated for C$_{13}$H$_{20}$N$_3$O$_3$S, 298.1225). found 298.1218.

(S)-1-(2-(3-fluorophenylamino)-2-oxoethyl)-N-(thiazol-2-yl)pyrrolidine-2-carboxamide (compound (103))

A solution of compound (102) (0.363 mmol) in a mixture of TFA/CH$_2$Cl$_2$ (1:2, 10 mL/mmol) was stirred for 2 hours at room temperature. The solvent was then removed under reduced pressure to give a light yellow oil to which was added HCl in Et$_2$O (20 mL). The resulting white precipitate was then filtered, and dried under reduced pressure to afford a white solid. To the remaining solid was added 2-chloro-N-(3-(trifluoromethyl)phenyl)acetamide (0.399 mmol), K$_2$CO$_3$ (1.815 mmol), and a catalytic amount of NaI, and DMF (6 mL) was stirred at 65° C. overnight. The reaction was cooled to room temperature then poured into H$_2$O (60 mL) and the mixture extracted with EtOAc (3×15 mL). The combined organic portion was then washed with brine (25 mL) and dried (Na$_2$SO$_4$). The solvent was then removed under reduced pressure and the resulting residue was purified by flash column chromatography (eluent: EtOAc/CH$_2$Cl$_2$, 7:13) to afford a clear oil that was crystallized from Et$_2$O as a white solid (72 mg, 49.7%). $^1$H NMR (500 MHz, Chloroform-d) δ 11.48 (s, 1H), 9.46 (s, 1H), 7.91-7.87 (m, 2H), 7.46-7.40 (m, 2H), 7.34 (dq, J=7.0, 1.0 Hz, 1H), 7.02 (d, J=3.6 Hz, 1H), 3.67 (dd, J=9.5, 4.6 Hz, 1H), 3.60-3.45 (m, 2H), 3.45-3.36 (m, 1H), 2.76 (td, J=8.9, 7.5 Hz, 1H), 2.43-2.31 (m, 1H), 2.16-2.08 (m, 1H), 1.99 (tdd, J=8.5, 6.2, 4.9 Hz, 2H). $^{13}$C NMR (126 MHz, CDCl$_3$) δ 172.62, 169.16, 158.79, 138.27, 136.78, 131.32 (q, $^2J_{CF}$=32.23), 129.42, 123.90 (q, $^1J_{CF}$=272.47), 122.90, 120.69 (q, $^3J_{CF}$=3.52), 116.54 (q, $^3J_{CF}$=4.00), 114.20, 67.87, 59.53, 55.21, 31.54, 24.94. HRESIMS (m/z); [M+Na] (calc for C$_{17}$H$_{17}$F$_3$N$_4$O$_2$SNa, 421.0917). found 421.0922; HPLC t$_r$=4.154 min

DOCUMENTS (2010) Annual report on the state of the drugs problem in Europe. in *The European Monitoring Centre for Drugs and Drug Addiction (EMCDDA)*, Office of the European Union, Lisbon (2010) *Results from the 2009 National Survey on Drug Use and Health: Summary of National Findings*, Office of Applied Studies, Rockville, Md.

Barducci A, Bussi G, Parrinello M (2008) Well-tempered metadynamics: a smoothly converging and tunable free-energy method. Phys Rev Lett 100: 020603.

Branduardi D, Gervasio F L, Parrinello M (2007) From A to B in free energy space. J Chem Phys 126: 054103.

Bruchas M R, Chavkin C (2010) Kinase cascades and ligand-directed signaling at the kappa opioid receptor. Psychopharmacology (Berl) 210: 137-147.

Carlsson, J., Yoo, L, Gao, Z. G., Irwin, J. J., Shoichet, B. K., and Jacobson, K. A. (2010) *J Med Chem* 53, 3748-3755

Chavkin C (2011) The therapeutic potential of kappa-opioids for treatment of pain and addiction. Neuropsychopharmacology 36: 369-370.

Chen, Y., Mestek, A., Liu, J., Hurley, J. A., and Yu, L. (1993) *Mol Pharmacol* 44, 8-12

Darden T, York D, Pederson L (1993) Particle mesh Ewald: an N log(N) method for Ewald sums in large systems. J Chem Phys 98: 10089-10092.

DeLander G E, Portoghese P S, Takemori A E (1984) Role of spinal mu opioid receptors in the development of morphine tolerance and dependence. J Pharmacol Exp Ther 231: 91-96.

Evans, C. J., Keith, D. E., Jr., Morrison, H., Magendzo, K., and Edwards, R. H. (1992) *Science* 258, 1952-1955

Fields H L (2007) Understanding how opioids contribute to reward and analgesia. Reg Anesth Pain Med 32: 242-246.

Filizola M, Devi L A (2012) Structural biology: How opioid drugs bind to receptors. Nature 485: 314-317.

Filizola, M., and Devi, L. A. (2012b) Grand opening of structure-guided design for novel opioids. *Trends in Pharmacological Sciences* in press Fribourg M, Moreno J L, Holloway T, Provasi D, Baki L, Mahajan R, Park G, Adney S K, Hatcher C, Eltit J M, Ruta J D, Albizu L, Li Z, Umali A, Shim J, Fabiato A, MacKerell A D, Jr., Brezina V, Sealfon S C, Filizola M, Gonzalez-Maeso J, Logothetis D E (2011) Decoding the signaling of a GPCR heteromeric complex reveals a unifying mechanism of action of antipsychotic drugs. Cell 147: 1011-1023.

Gales, C., Van Durm, J. J., Schaak, S., Pontier, S., Percherancier, Y., Audet, M., Paris, H., and Bouvier, M. (2006) *Nat Struct Mol Biol* 13, 778-786

Granier S, Manglik A, Kruse A C, Kobilka T S, Thian F S, Weis W I, Kobilka B K (2012) Structure of the delta-opioid receptor bound to naltrindole. Nature 485: 400-404.

Gu S J, Lee J K, Pae A N, Chung H J, Rhim H, Han S Y, Min S J, Cho Y S (2010) Synthesis and biological evaluation of 1,4-diazepane derivatives as T-type calcium channel blockers. Bioorg Med Chem Lett 20: 2705-2708.

Guo, W., Urizar, E., Kralikova, M., Mobarec, J. C., Shi, L., Filizola, M., and Javitch, J. A. (2008) *Embo J* 27, 2293-2304

Henry, D. J., Grandy, D. K., Lester, H. A., Davidson, N., and Chavkin, C. (1995) *Mol Pharmacol* 47, 551-557

Hess B, Bekker H, Berendsen H J C, Fraaije J G E M (1997) LINCS: A linear constraint solver for molecular simulations. Journal of Computational Chemistry 18: 1463-1472.

Irwin J J, Shoichet B K (2005) ZINC-a free database of commercially available compounds for virtual screening. J Chem Inf Model 45: 177-182.

Jiang, L. I., Collins, J., Davis, R., Lin, K. M., DeCamp, D., Roach, T., Hsueh, R., Rebres, R. A., Ross, E. M., Taussig, R., Fraser, I., and Sternweis, P. C. (2007) *J Biol Chem* 282, 10576-10584

Kandt C, Ash W L, Tieleman D P (2007) Setting up and running molecular dynamics simulations of membrane proteins. Methods 41: 475-488.

Kieffer, B. L., Befort, K., Gaveriaux-Ruff, C., and Hirth, C. G. (1992) *Proc Natl Acad Sci USA* 89, 12048-12052

Klewe, I. V., Nielsen, S. M., Tarpo, L., Urizar, E., Dipace, C., Javitch, J. A., Gether, U., Egebjerg, J., and Christensen, K. V. (2008) *Neuropharmacology* 54, 1215-1222

Kuntz, I. D., Blaney, J. M., Oatley, S. J., Langridge, R., and Ferrin, T. E. (1982) *J. Mol. Biol.* 161, 269-288

Land B B, Bruchas M R, Schattauer S, Giardino W J, Aita M, Messinger D, Hnasko T S, Palmiter R D, Chavkin C (2009) Activation of the kappa opioid receptor in the dorsal raphe nucleus mediates the aversive effects of stress and reinstates drug seeking. Proc Natl Acad Sci USA 106: 19168-19173.

Lorber, D. M., and Shoichet, B. K. (1998) *Protein Sci.* 7, 938-950

Lorber, D. M., and Shoichet, B. K. (2005) *Curr. Top. Med. Chem.* 5, 739-749

Luo Q L, Li J Y, Liu Z Y, Chen L L, Li J, Ye Q Z, Nan F J (2005) Inhibitors of type I MetAPs containing pyridine-2-carboxylic acid thiazol-2-ylamide. Part 1: SAR studies on the determination of the key scaffold. Bioorg Med Chem Lett 15: 635-638.

Ma L, Xie C, Ma Y, Liu J, Xiang M, Ye X, Zheng H, Chen Z, Xu Q, Chen T, Chen J, Yang J, Qiu N, Wang G, Liang X, Peng A, Yang S, Wei Y, Chen L (2011) Synthesis and biological evaluation of novel 5-benzylidenethiazolidine-2,4-dione derivatives for the treatment of inflammatory diseases. J Med Chem 54: 2060-2068.

Mackerell A D, Jr., Feig M, Brooks C L, 3rd (2004) Extending the treatment of backbone energetics in protein force fields: limitations of gas-phase quantum mechanics in reproducing protein conformational distributions in molecular dynamics simulations. J Comput Chem 25: 1400-1415.

Mackerell Jr. A D, Bashford D, Bellot M, Dunbrack R L, Evanseck J D, Field M J, Fischer S, Gao J, Guo H, Ha S, Joseph-McCarthy D, Kuchnir L, Kuczera K, Lau T K, Mattos C, Michnick S, Ngo T, Nguyen D T, Prodhom B, Reiher W E, Roux B, Schlenkrich B, Smith J, Stote R, Straub J, Watanabe M, Wiorkiewicz-Kuczera J, Karplus M (1998) All-atom empirical potential for molecular modeling and dynamics studies of proteins. J Phys Chem B 102: 3586-3616.

Manglik A, Kruse A C, Kobilka T S, Thian F S, Mathiesen J M, Sunahara R K, Pardo L, Weis W I, Kobilka B K, Granier S (2012) Crystal structure of the mu-opioid receptor bound to a morphinan antagonist. Nature 485: 321-326.

Marchi M, Ballone P (1999) Adiabatic bias molecular dynamics: a method to navigate the conformational space of complex molecular systems. J Chem Phys 110: 3697-3702.

McCurdy, C. R., and Prisinzano, T. E. (2010) Opioid receptor ligands. in *Burger's Medicinal Chemistry, Drug Discovery, and Development, Seventh edition* (Abraham, D. J., and Rotella, D. R. eds.), John Wiley & Sons, Inc. pp 569-735

Minami, M., Toya, T., Katao, Y., Maekawa, K., Nakamura, S., Onogi, T., Kaneko, S., and Satoh, M. (1993) *FEBS Lett* 329, 291-295

Miyamoto S, Kollman P A (1992) SETTLE: ananalytical version of the SHAKE and RATTLE algorithm for rigid water models. J Comput Chem 13: 952-962.

Molinari P, Vezzi V, Sbraccia M, Gro C, Riitano D, Ambrosio C, Casella I, Costa T (2010) Morphine-like opiates selectively antagonize receptor-arrestin interactions. J Biol Chem 285: 12522-12535.

Mysinger, M. M., and Shoichet, B. K. (2010) *J Chem Inf Model* 50, 1561-1573

Nagase H, Fujii H (2011) Opioids in preclinical and clinical trials. Top Curr Chem 299: 29-62.

Negri A, Li J, Naini S, Coller B S, Filizola M (2012) Structure-based virtual screening of small-molecule antagonists of platelet integrin alphaIIbbeta3 that do not prime the receptor to bind ligand. J Comput Aided Mol Des.

Negri A, Rives M L, Gaspers M J, Prisinzano T E, Javitch J A, Filizola M (2012) Virtual Screening against the Kappa-Opioid Receptor X-ray Structure Leads to the Discovery of a Novel Selective Agonist Chemotype for this Receptor. submitted.

Negri, A., Li, J., Naini, S., Coller, B. S., and Filizola, M. (2012) *J Comput Aided Mol Des*

Provasi D, Artacho M C, Negri A, Mobarec J C, Filizola M (2011) Ligand-induced modulation of the free-energy landscape of G protein-coupled receptors explored by adaptive biasing techniques. PLoS Comput Biol 7: e1002193.

Rasmussen S G, DeVree B T, Zou Y, Kruse A C, Chung K Y, Kobilka T S, Thian F S, Chae P S, Pardon E, Calinski D, Mathiesen J M, Shah S T, Lyons J A, Caffrey M, Gellman S H, Steyaert J, Skiniotis G, Weis W I, Sunahara R K, Kobilka B K (2011) Crystal structure of the beta2 adrenergic receptor-Gs protein complex. Nature 477: 549-555.

Rives M L, Rossillo M, Liu-Chen L Y, Javitch J A (2012) 6'-Guanidinonaltrindole (6'-GNTI) is a G protein-biased kappa-opioid receptor agonist that inhibits arrestin recruitment. J Biol Chem 287: 27050-27054.

Rogers, D., Brown, R. D., and Hahn, M. (2005) J Biomol Screen 10, 682-686

Rohl C A, Strauss C E, Chivian D, Baker D (2004) Modeling structurally variable regions in homologous proteins with rosetta. Proteins 55: 656-677.

Rozenfeld R, Devi L A (2010) Receptor heteromerization and drug discovery. Trends Pharmacol Sci 31: 124-130.

Sauliere, A., Bellot, M., Paris, H., Denis, C., Finana, F., Hansen, J. T., Altie, M. F., Seguelas, M. H., Pathak, A., Hansen, J. L., Senard, J. M., and Gales, C. (2012) *Nat Chem Biol* 8, 622-630

Tallent, M., Dichter, M. A. Bell, G. L, and Reisine, T. (1994) *Neuroscience* 63, 1033-1040

Taussig, R., Iniguez-Lluhi, J. A., and Gilman, A. G. (1993) *Science* 261, 218-221

Thompson, A. A., Liu, W., Chun, E., Katritch, V., Wu, H., Vardy, E., Huang, X. P., Trapella, C., Guerrini, R., Calo, G., Roth, B. L., Cherezov, V., and Stevens, R. C. (2012) *Nature* 485, 395-399

Van Der Spoel D, Lindahl E, Hess B, Groenhof G, Mark A E, Berendsen H J (2005) GROMACS: fast, flexible, and free. J Comput Chem 26: 1701-1718.

van Rijn R M, Whistler J L, Waldhoer M (2010) Opioid-receptor-heteromer-specific trafficking and pharmacology. Curr Opin Pharmacol 10: 73-79.

Vanderah T W (2010) Delta and kappa opioid receptors as suitable drug targets for pain. Clin J Pain 26 Suppl 10: S10-15.

Waldhoer M, Fong J, Jones R M, Lunzer M M, Sharma S K, Kostenis E, Portoghese P S, Whistler J L (2005) A heterodimer-selective agonist shows in vivo relevance of G protein-coupled receptor dimers. Proc Natl Acad Sci USA 102: 9050-9055.

Wang C, Bradley P, Baker D (2007) Protein-protein docking with backbone flexibility. J Mol Biol 373: 503-519.

Wang Y H, Sun J F, Tao Y M, Chi Z Q, Liu J G (2010) The role of kappa-opioid receptor activation in mediating antinociception and addiction. Acta Pharmacol Sin 31: 1065-1070.

Wawer, M., and Bajorath, J. (2010) *J Chem Inf Model* 50, 1395-1409

Weiner, S. J., Kollman, P. A., Case, D. A., Singh, U. C., Ghio, C., Alagona, G., Profeta, S., and Weiner, P. A. (1984) *J. Am. Chem. Soc.* 106, 765-784

Wu, H., Wacker, D., Mileni, M., Katritch, V., Han, G. W., Vardy, E. Liu, W., Thompson, A. A Huang, X. P., Carroll, F. I Mascarella, S. W., Westkaemper, R. B., Mosier, P. D., Roth, B. L., Cherezov, V., and Stevens, R. C. (2012) *Nature* 485, 327-332

Yu C, Qiu J, Zheng F, Zhong W (2011) Highly efficient bifunctional organocatalysts for the asymmetric Michael addition of ketones to nitroolefins. Tetrahedron Lett 52: 3298-3302.

Zhu J, Choi W S, McCoy J G, Negri A, Naini S, Li J, Shen M, Huang W, Bougie D, Rasmussen M, Aster R, Thomas C J, Filizola M, Springer T A, Coller B S (2012) Structure-guided design of a high-affinity platelet integrin alphaIIbbeta3 receptor antagonist that disrupts Mg(2)(+) binding to the MIDAS. Sci Transl Med 4: 125ra132.

Zhu J, Negri A, Provasi D, Filizola M, Coller B S, Springer T A (2010) Closed headpiece of integrin alphaIIbbeta3 and its complex with an alphaIIbbeta3-specific antagonist that does not induce opening. Blood 116: 5050-5059.

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

What is claimed is:

1. A compound of formula I:

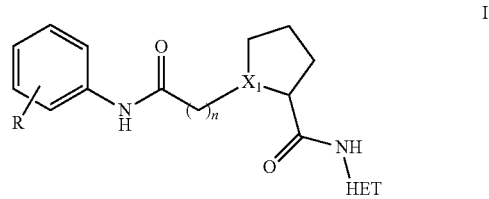

wherein $X_1$ is N;

n is an integer between 1 and 10;

HET is a heteroaromatic ring; and

R is a —$C_{1-4}$alkylhalo; or crystalline forms, hydrates, or salts thereof.

2. A compound of formula II:

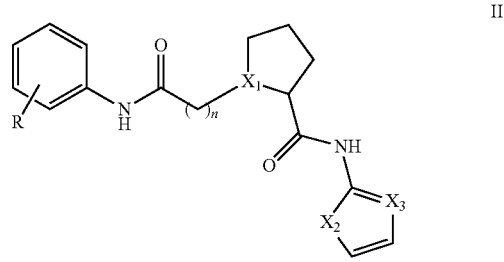

wherein $X_1$ and $X_3$ are N;

$X_2$ is selected from the group consisting of N, O, and S;

n is an integer between 1 and 10; and

R is a —$C_{1-4}$alkylhalo; or crystalline forms, hydrates, or salts thereof.

3. A compound of formula V:

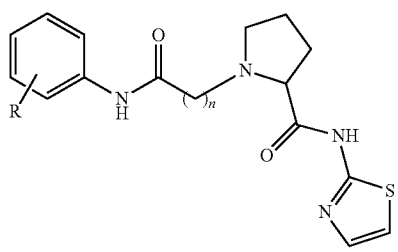

wherein
n is selected from an integer between 1 and 10; and
R is a —$C_{1-4}$alkylhalo; or
crystalline forms, hydrates, or salts thereof.

4. A pharmaceutical composition comprising a compound according to claim 1 and a pharmaceutically acceptable carrier.

5. A method for treating or ameliorating the effects of a condition in a subject in need thereof comprising administering to the subject an effective amount of a compound according to claim 1, wherein the condition is selected from the group consisting of pain, coughing, depression, and itching.

6. The method according to claim 5, wherein the subject is a human.

7. A method for treating or ameliorating the effects of a condition in a subject in need thereof comprising administering to the subject an effective amount of a pharmaceutical composition according to claim 4, wherein the condition is selected from the group consisting of pain, coughing, depression, and itching.

8. The method according to claim 7, wherein the subject is a human.

9. A method for treating pain in a subject comprising administering to the subject an effective amount of a non-addictive pharmaceutical composition comprising a pharmaceutically acceptable carrier and a compound of formula I:

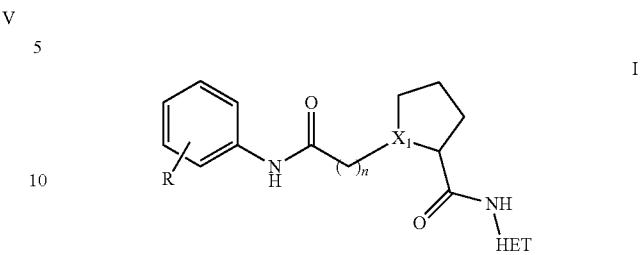

wherein
$X_1$ is N;
n is an integer between 1 and 10;
HET is a heteroaromatic ring; and
R is a —$C_{1-4}$alkylhalo; or
crystalline forms, hydrates, or salts thereof;
further wherein the compound is biased toward G protein activation over arrestin.

10. A compound of the structure:

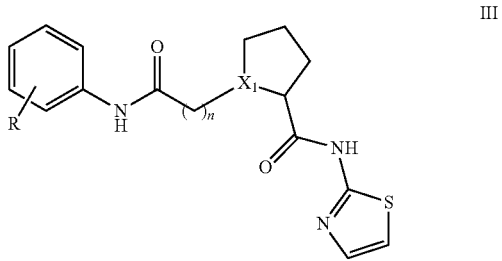

or crystalline forms, hydrates, or salts thereof.

11. A pharmaceutical composition comprising the compound according to claim 10 and a pharmaceutically acceptable carrier.

* * * * *